United States Patent
Lemaux et al.

(10) Patent No.: US 7,102,056 B1
(45) Date of Patent: Sep. 5, 2006

(54) COMPOSITIONS AND METHODS FOR PLANT TRANSFORMATION AND REGENERATION

(75) Inventors: Peggy G. Lemaux, Moraga, CA (US); Myeong-Je Cho, Alameda, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/552,252

(22) Filed: Apr. 18, 2000

Related U.S. Application Data

(63) Continuation-in-part of application No. 08/845,939, filed on Apr. 29, 1997, now Pat. No. 6,235,529.

(51) Int. Cl.
*A01H 1/00* (2006.01)
*A01H 5/00* (2006.01)
*C12N 15/82* (2006.01)
*C12N 5/02* (2006.01)
*C12N 15/11* (2006.01)

(52) U.S. Cl. .................. 800/278; 800/288; 800/293; 800/320; 435/412; 435/424; 435/430; 435/430.1; 435/431; 536/23.1

(58) Field of Classification Search ............. 435/430.1, 435/410, 420, 430, 431, 468, 419; 800/278, 800/320, 295, 298, 320.1, 320.2, 320.3, 293
See application file for complete search history.

(56) References Cited

U.S. PATENT DOCUMENTS

| | | | |
|---|---|---|---|
| 4,699,644 A | | 10/1987 | Brandt et al. |
| 5,164,310 A | | 11/1992 | Smith et al. |
| 5,281,529 A | | 1/1994 | Zhong et al. |
| 5,320,961 A | | 6/1994 | Zhong et al. |
| 5,350,688 A | | 9/1994 | Matsuno et al. |
| 5,403,736 A | | 4/1995 | Tanimoto |
| 5,405,765 A | * | 4/1995 | Vasil et al. ............... 435/172.3 |
| 5,565,355 A | | 10/1996 | Smith |
| 5,589,617 A | | 12/1996 | Nehra et al. |
| 5,610,042 A | | 3/1997 | Chang et al. |
| 5,641,664 A | | 6/1997 | D'Halluin et al. |
| 6,235,529 B1 | * | 5/2001 | Lemaux et al. ........... 435/439.1 |

FOREIGN PATENT DOCUMENTS

| EP | 0558676 | 9/1993 |
|---|---|---|
| JP | 04027466 | 1/1989 |
| JP | 07255304 | 3/1994 |
| JP | 07212183 | 8/1995 |
| WO | WO92/20809 | 11/1992 |
| WO | WO94/13822 | 6/1994 |
| WO | WO96/04392 | 2/1996 |

OTHER PUBLICATIONS (Bhojwani, et al., in Plant Tissue Culture, Elsevier, Amsterdam, 1983, pp. 25–41,see Table 3.1 and 3.2 p. 29).*
Wan and Lemaux, Plant Physiology (1994) 104: 37–48.*
Purnhauser, Central Research Communication, 1991, vol. 19: 419–424.
Gless et al. (1998), "Transgenic Oat Plants Obtained at High Efficiency by Microprojectile Bombardment of Leaf Base Segments," J. Plant Physiol., 152:151–157.
Napoli et al. (1990), "Introduction of a Chimeric Chalcone Synthase Gene into Petunia Results in Reversible Co–Suppression of Homlogous Genes in trans," The Plant Cell, 2:279–289.
Potrykus (1991), "Gene Transfer to Plants: Assessment of Published Approaches and Results," Annu. Rev. Plant Physiol. Plant Mol. Biol., 42:205–225.
Somers et al. (1992), "Fertile, Transgenic Oat Plants," Biotechnology, 10:1589–1594.
Torbet et al. (1995), "Use of paromomycin as a selective agent for oat transformation," Plant Cell Reports, 14:635–640.
Wan et al. (1995), "Type I callus as a bombardment target for generating fertile transgenic maize (*Zea mays* L.)", Planta, 196:7–14.
Zaghmout & Torello (1992), "Plant Regeneration from Callus and Protoplasts of Perennial Ryegrass (*Lolium perenne* L.)," J. Plant Physiol., 140:101–105.
Zhong et al. (1996), "The Competence of Maize Shoot Meristems for Integrative Transformation and Inherited Expression of Transgenes," Plant Physiol., 110:1097–1107.
Holm et al., (1994) "Regeneration of fertile barley plants from mechanically isolated protoplasts of the fertilized egg cell," Plant Cell, 6:531–543, Abstract Only.
Jain et al., (1995), "An improved procedure for plant regeneration from indica and japonica rice protoplasts," Plant Cell Reports, 14:515–519, Abstract Only.
Baille et al., 1992, "Field evaluation of barley (*Hordeum vulgare* L.) genotypes derived from tissue culture," Can. J. Plant Sci., 72:725–733.
Bhaskaran et al., 1990, "Regeneration in Cereal Tissue Culture: A Review," Crop Sci., 30:1328–1337.
Bregitzer et al, 1992, "Plant Regeration and Callus Type in Barley: Effects of Genotype and Culture Medium," Crop Sci., 32:1108–1112.

(Continued)

Primary Examiner—Phuong T. Bui
Assistant Examiner—Georgia L. Helmer
(74) Attorney, Agent, or Firm—Morrison & Foerster LLP

(57) ABSTRACT

Improved compositions and methods for transformation and regeneration of plants from embryogenic callus are disclosed that include, for example: use of an intermediate-incubation medium after callus induction to increase the competence of the transformed cells for regeneration; dim light conditions during early phases of selection; use of green callus tissue as a target for microprojectile bombardment; and media with optimized levels of phytohormones and copper concentrations.

22 Claims, 1 Drawing Sheet

OTHER PUBLICATIONS

Bregitzer et al, 1995), "Plant regeneration from barley callus: Effects of 2, 4–dichlorophenoxyacetic acid and phynylacetic acid," Plant Cell Tiss. Org. Cult., 43:229–235.

Christensen et al., 1996, "Ubiquitin promoter–based vectors for high–level expression of selectable and/or screenable marker genes in monocotyledonous plants," Transgenic Res., 5:1–6.

Dahleen, 1995, "Improved plant regeneration from barley callus cultures by increased copper levels," Plant Cell Tiss. Org. Cult., 43:267–269.

De Block et al., 1987, "Engineering herbicide resistance in plants by expression of a detoxifying enzyme," EMBO J., 6:2513–2518.

Fletcher, 1969, "Retardation of Leaf Senescence by Benzyladenine in Intact Bean Plants," Planta, 89:1–8.

Fromm et al., 1986, "Stable transformation of maize after gene transfer by electroporation," Nature, 319:791–793.

Fromm et al., 1989, "An Octopine Synthase Enhancer Element Directs Tissue–Specific Expression and Binds ASF–1, a Factor from Tobacco Nuclear Extracts," Plant Cell, 1:977–984.

Funatsuki et al., 1995, "Fertile transgenic barley generated by direct DNA transfer to protoplasts," Theor. Appl. Genet., 91:707–712.

Ghaemi et al., 1994, "The effects if silver nitrate, colchicines, cupric sulfate and genotype on the production of embryoids from anthers of teraploid wheat (*Triticum turgidum*)," Plant Cell Tiss. Org. Cult., 36:355–359.

Goldstein et al., 1986, "Tissue culture and plant regeneration from immature embryo explants of Barley, *Hordeum vulgare*," Theor, Appl. Genet., 71:631–636.

Gordon–Kamm et al., 1990, "Transformation of Maize Cells and Regeneration of Fertile Transgenic Plants," Plant Cell, 2:603–618.

Griffin et al., 1995, "High–frequency plant regeneration from seed–derived callus cultures of Kentucky bluegrass (*Poa pratensis* L.)," Plant Cell Rep., 14:721–724.

Hagio et al., 1995, "Production of fertile transgenic barley (*Hordeum vulgare* L.) plant using the hygromycin–resistance marker," Plant Cell Rep., 14:329–334.

Hanzel et al., 1985, "Genotype and Media Effects on Callus Formation and Regeneration in Barley," Crop Sci., 25:27–31.

Holtorf et al., 1995, "Two routes of chlorophyllide synthesis that are differentially regulated by light in barley (*Hordeum vulgare* L.)," Proc. Natl. Acad. Sci. USA, 92:3254–3258.

Jahne et al., 1991, "Regeneration of fertile plants from protoplasts derived from embryogenic cell suspensions of barley (*Hordeum vulgare* L.)," Plant Cell Rep., 10:1–6.

Jahne et al., 1994, "Regeneration of transgenic, microspore-derived, fertile barley," Theor. Appl Genet., 89:525–533.

Kasha et al., 1991, "Haploids in Cereal Improvement: Anther and Microspore Culture," In: Gene Manipulation in Plant Improvement II, Gustafson (ed.), Plenum Press: New York, pp. 213–235.

Kott et al., 1984, "Initiation and morphological development of somatic embryoids from barley cell cultures," Can. J. Bot., 62:1245–1249.

Lemaux et al., 1996, Bombardment–Mediated Transformation Methods for Barley, Bio–Rad US/EG Bulletin 2007.

Luhrs et al., 1987, "Plant regeneration in vitro from embryogenic cultures of spring– and winter–type barley (*Hordeum vulgare* L.) varieties," Theor. Appl. Genet., 75:16–25./.

Murakami et al., 1986, "The bialophos biosynthetic genes of *Streptomyces hygroscopicus:* Molecular cloning and characterization of the gene cluster," Mol. Gen. Genet., 205:42–50.

Salmenkallio–Marttila et al., 1995, "Transgenic barley (*Hordeum vulgare* L) by electroporation of protoplasts," Plant Cell Rep., 15:301–304.

Thompson et al., 1987, "Characterization of the herbicide–resistance gene bar from *Streptomyces hygroscopicus*," EMBO J., 6:2519–2523.

Wan et al., 1994, "Generation of Large Numbers of Independently Transformed Fertile Barley Plants," Plant Physiol. 104:37–48.

Wan et al., 1994, "Biolistic Transformation of Microspore–Derived and Immature Zygotic Embryos and Regeneration of Fertile Transgenic Barley Plants," In: Gene Transfer to Plants, eds. Potrykus and Spangenberg, Springer Verlag, pp. 139–146.

Zhang et al., 1996, "Production of Multiple Shoots from Shoof Apical Meristems of Oat (*Avena sativa* L.)," J. Plant Physiol, 148:667–671.

Zhong et al., 1991, "Plant regeneration via somatic embryogenesis in creeping bentgrass (*Agrostis palustris* Huds.)," Plant Cell Rep., 10:453–456.

Zhong et al., 1992, "In–vitro morphogenesis of corn (*Zea mays* L.)," Planta, 187:483–489.

* cited by examiner

COMPOSITIONS AND METHODS FOR PLANT TRANSFORMATION AND REGENERATION

CROSS-REFERENCE TO RELATED APPLICATIONS

This application is a continuation-in-part of U.S. application Ser. No. 08/845,939 (filed on Apr. 29, 1997, now issued as U.S. Pat. No. 6,235,529, which is hereby incorporated herein in its entirety by reference.

FIELD OF THE INVENTION

This invention relates to compositions and methods for the in vitro culture, transformation, and regeneration of plants.

BACKGROUND OF THE INVENTION

Genetic improvement of various crop species by genetic engineering has sometimes been hindered because techniques for in vitro culture, transformation, and regeneration of model cultivars are less effective with recalcitrant commercial cultivars.

Barley (*Hordeum vulgare* L.) is one of the world's most important cereal crops, closely following wheat, rice and maize in total production. Barley is used worldwide for feed, food, and malting purposes.

The ability to genetically engineer barley to improve its performance and pest-resistance or to enhance alternative uses is of great importance. The practical utility of stable transformation technologies is largely dependent on the availability of efficient methods for generating large numbers of fertile green plants from tissue culture materials. Procedures have been described for generating highly embryogenic barley callus and regenerating green plants (Dale and Dambrogio, 1979; Handel et al., 1985; Thomas and Scott, 1985; Goldenstein and Kronstadt, 1986; Lürz and Lörz, 1987; Wan and Lemaux, 1994; Hagio et al., 1995; Dahleen, 1996). However, presently available procedures for producing embryogenic callus and regenerating green plants have been of limited utility when used in transformation procedures for commercially important barley genotypes. These procedures have been hampered by a gradual loss of the embryogenic capacity and regenerability of callus tissue and an increase in albino (chlorophyll-deficient) plants during the prolonged periods needed to select transformed tissue. For example, of the independently transformed callus lines generated by one transformation procedure for the barley genotype Golden Promise, only 51% of transformed lines give rise to green plants and some of these lines regenerated only a small number of green plants (Wan and Lemaux, 1994; Lemaux et al., 1996). When the same procedure was applied to the commercial barley genotypes Moravian III and Galena, none of the resulting transformed lines gave rise to green plants.

There is a need, therefore, for efficient methods for transformation and regeneration that can be used with a wide variety of barley genotypes, including commercially important genotypes.

SUMMARY OF THE INVENTION

We have developed improved methods and compositions for plant transformation and regeneration. The examples below detail the application of these methods and compositions to various barley genotypes, including commercially important genotypes that have proven difficult or impossible to transform and regenerate by previously available methods. These improved methods, when applied to barley, result in a significantly higher regeneration frequency, reduce somaclonal variation, and improve the incidence of fertile, green transformed plants. The methods of the present invention are not limited to barley, however, but can be used for transformation and regeneration of other plant species including, but not limited to, oat, wheat, maize, rice, sorghum, rye, sugarcane, orchardgrass, tall fescue, red fescue, creeping bentgrass and Kentucky bluegrass.

One aspect of the present invention encompasses methods for producing a transformed plant that comprise introducing a nucleic acid into green regenerative tissue which is also referred to as green callus tissue. More specifically, such methods comprise the steps of:

(1) introducing a nucleic acid into a cell of green regenerative tissue to produce a transformed plant cell;
(2) culturing the transformed plant cell under dim light conditions on an intermediate-incubation medium (IIM) comprising an auxin and a cytokinin, thereby promoting proliferation and formation of a transformed structure that is competent to regenerate; and
(3) culturing the transformed structure on a regeneration medium (RM) to produce the transformed plant.

Selection for transformed cells can begin immediately after introduction of DNA into a cell. Alternatively, selection can begin later to provide sufficient time for initial cell proliferation in the absence of the selective agent. Once initiated, selection is generally maintained during the incubation on IIM and, depending on the selective agent, can also be maintained during the regeneration step.

Another aspect of the present invention encompasses methods for the preparing green regenerative tissues. The methods involve incubating plant tissue under dim light conditions on a growth medium for a sufficient time to produce green regenerative tissue. Preferably the growth medium comprises comprises auxin at a concentration of about 0.1 mg/L to about 5 mg/L, cytokinin at a concentration of from 0.01 mg/L to about 2 mg/L, copper at a concentration of about 0.1 µM to about 50 µM, and a carbon source. Generally, the plant tissue is callus tissue, particularly callus derived from an immature embryo, or a germinating mature embryo or mature seed. Such callus can be produced by incubating immature embryos on a callus-induction medium (CIM), or by germinating seeds in culture on a CIM, excising the shoots and roots and incubating the remaining portion of the germinating seed under dim light conditions and selecting nodular, compact structures that form on the germinating seed.

The green regenerative tissues find use as transformation targets. The green regenerative tissues also find use in methods for regenerating transformed or non-transformed plants. Plants can be regenerated by incubating the green regenerative tissues on a regeneration medium.

The present invention encompasses optimized plant culture media and the use of such media for plant cell and tissue culture. Such optimized media include phytohormones and copper (e.g., cupric sulfate), which improve callus quality during initiation, promote the regenerability of the tissue, and reduce the incidence of albinism during the period of callus maintenance and regeneration. The media also includes conventional plant nutrients and can also include a carbon source such as maltose (which is better than sucrose for initiation of some species, including barley, wheat, and rice).

In preferred embodiments, the CIM includes an auxin (e.g., 2,4-dichlorophenoxyacetic acid, NAA, dicamba, picloram, IAA and 2,4,5-T), for example at a concentration of about 0.1 mg/L to about 5.0 mg/L, preferably about 1.0 mg/L to about 2.5 mg/L. The CIM can also include a cytokinin (e.g., 6-benzylaminopurine, zeatin, and kinetin), e.g., at a concentration of about 0.01 mg/L to about 0.5 mg/L for initial callus induction and about 0.1 mg/L to about 2.0 mg/L for maintenance of callus and green tissues.

In preferred embodiments, the IIM contains an auxin, e.g., at a concentration of about 0.1 mg/L to about 5.0 mg/L, preferably about 0.5 mg/L to about 2.5 mg/L, and a cytokinin, e.g., at a concentration of about 0.1 mg/L to about 5.0 mg/L, preferably about 0.1 mg/L to about 2.0 mg/L.

The CIM and IIM also preferably include copper, e.g., a concentration of about 0.1 $\mu$M to about 50 $\mu$M.

Another aspect of the present invention encompasses the use of dim light conditions. Dim light conditions allow callus to become green and reduce the incidence of regeneration of fertile green plants, and may improve the regenerability of the callus tissue. Dim light conditions also permit one to screen for green portions of the callus (for barley, for example; yellow-green portions for wheat), which are more likely to be regenerable. Green callus is useful as a target plant tissue for transformation, e.g., by microprojectile bombardment or infection by *Agrobacterium*. Callus grown in dim light on a CIM develops or maintains regenerative structures and can be maintained in this state for at least ten months for Golden Promise, Galena, and Harrington, and at least four to six months for Morex, for example.

Another aspect of the present invention is the use of microprojectile bombardment for plant transformation, wherein the bombardment is performed below 1300 psi, e.g., at 450–900 psi. Lowering the rupture pressure and hence the speed of the microprojectiles lessens damage to the target tissue and results in less stress to the transformed cells.

Another aspect of the present invention encompasses transformed plants and plant culture media as described herein.

The foregoing and other aspects of the invention will become more apparent from the following detailed description.

DETAILED DESCRIPTION OF THE PREFERRED EMBODIMENTS

Figure 1A:
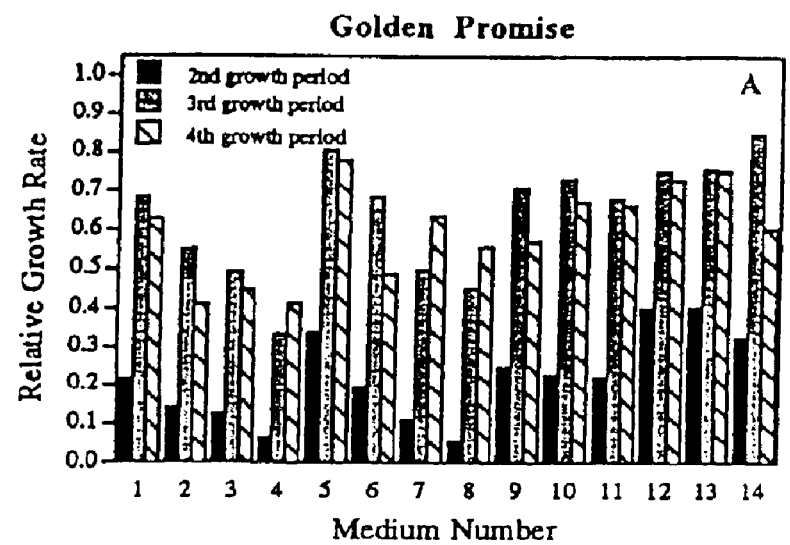
FIG. 1A shows the relative growth rate (g/g fresh weight/day) of callus of the barley genotype Golden Promise grown on fourteen different media. (The auxin and cytokinin concentrations of the media are given in Table 1.)

We have developed improved methods for plant transformation and regeneration and compositions useful for such methods. Although these methods are generally applicable to barley varieties, including recalcitrant genotypes, they are also applicable to other plant species as well.

Definitions and Methods

Unless otherwise noted, terms are to be understood according to conventional usage by those of ordinary skill in the relevant art. In addition to the definitions of terms provided below, definitions of common terms in molecular biology may also be found in Rieger et al., 1991; and Lewin, 1994.

Plant Transformation and Regeneration

"Transformed"; "Transgenic". A cell, tissue, organ, or organism into which a foreign nucleic acid, such as a recombinant vector, has been introduced is considered "transformed" or "transgenic," as is progeny thereof in which the foreign nucleic acid is present.

"Foreign" nucleic acids are nucleic acids that would not normally be present in the host cell, particularly nucleic acids that have been modified by recombinant DNA techniques. The term "foreign" nucleic acids also includes host genes that are placed under the control of a new promoter or terminator sequence, for example, by conventional techniques.

Transformation by particle bombardment. Particle bombardment has been employed for transformation of a number of plant species, including barley (see, e.g., Wan and Lemaux, 1994, and BioRad Technical Bulletin 2007) and corn (see, e.g., Gordon-Kamm et al., 1990). Successful transformation by particle bombardment requires that the target cells are actively dividing, accessible to microprojectiles, culturable in vitro, and totipotent, i.e., capable of regeneration to produce mature fertile plants.

Target tissues for microprojectile bombardment include immature embryos, young embryogenic callus from immature embryos, microspores, microspore-derived embryos, and apical meristem tissue. We have also found that green callus tissues are useful targets for bombardment, as discussed below.

Previously, bombardment of barley tissue such as immature zygotic embryos or young callus tissue was generally carried out at 1100 psi. We have found that a rupture pressure under 1100 psi, preferably less that 1000 psi, more preferably about 600 to 900 psi, resulted in a higher callus-induction frequency and a higher frequency of regenerative structures in Galena, for example, possibly due to reduced damage to the target tissue (although Golden Promise was unaffected in its frequency).

Green tissues as a target for particle bombardment. Barley callus tissue that is not exposed to light is moved through selection as rapidly as possible, since longer culture times result in lower regenerability and a higher incidence of albinism (Lemaux et al., 1996). We have discovered that green barley callus tissue can be maintained for more than 10 months (e.g., Golden Promise, Galena, Harrington, and Salome) on an IIM (discussed in detail below) and can subsequently regenerate at high frequency when transferred to a regeneration medium. The use of green tissues as a target for transformation by microprojectile bombardment permits long-term culture of barley, reducing the need to maintain high-quality donor plants throughout the year. It may also reduce the need to backcross barley transformants, since the green callus tissue is more highly differentiated than tissue that has not been exposed to light and may have a lower frequency of induced mutation and be less likely to exhibit somaclonal variation. Moreover, the incidence of albinism is significantly reduced compared to dark-grown tissue.

Other plant transformation methods. Any conventional method may be employed to transform plants, i.e., to introduce foreign DNA into a plant cell. The generation of stable transformants and fertile transgenic plants has been achieved, for example, in a wide variety of dicotyledonous plants and in such cereals as rice, maize, wheat, and oat by a variety of methods.

In addition to particle bombardment, conventional methods for plant cell transformation include, but are not limited to: (1) *Agrobacterium*-mediated transformation, (2)

microinjection, (3) polyethylene glycol (PEG) procedures, (4) liposome-mediated DNA uptake, (5) electroporation, and (6) vortexing with silica fibers.

Regeneration of Transformed Plant Cells. Transformed plant tissues are cultured on a regeneration medium to cause differentiation of the tissue to produce a fertile transgenic plant.

It is preferable that callus-induction and plant-regeneration be accomplished in three stages, each involving transformed cells or tissues on a medium supporting the biological events desired at each stage: callus induction, intermediate incubation, and regeneration.

"Callus-induction medium" (CIM) preferably promotes a fast growth rate without allowing substantial differentiation of the plant tissue into organized structures. A transformed cell arising from introduction of foreign DNA into a cell is incubated on CIM for a time sufficient for the cell to proliferate to form sufficient callus tissue to ensure that a sufficient number of progeny cells are produced from a single transformed cell to form numerous somatic embryos that will give rise to numerous transformed plants when regenerated. For that reason, CIM preferably includes an auxin (e.g., about 0.5 mg/L to about 5.0 mg/L of 2,4-dichlorophenoxyacetic acid [2,4-D] or dicamba) to promote rapid cell division. Cytokinin levels are preferably kept low for most genotypes for initial callus induction, particularly for recalcitrant genotypes (such as the barley genotypes Galena, Morex, or Harrington), because high cytokinin levels decrease the initial growth rate of the callus (high cytokinins also interfere with selection using bialaphos, although not when hygromycin or G418 is used). However, a cytokinin improves callus quality and regenerability and may reduce the incidence of albinism (i.e., induce the growth of more green regenerative tissues). Therefore, low levels of a cytokinin may be included in the CIM, e.g., 6-benzylaminopurine [BAP], zeatin, kinetin, etc., preferably BAP or kinetin, at levels of about 0.01 mg/L to about 1.0 mg/L for initial callus induction, about 0.1 mg/L to about 2.0 mg/L for callus maintenance. The optimal level of cytokinin depends on the genotype. CIM also preferably contains copper (about 0.1 µM to about 50 µM).

Callus tissue is divided into smaller pieces (e.g., for barley, pieces of about 3 to 5 mm are preferred) and subcultured, i.e., transferred to fresh medium, at regular intervals to promote optimal growth rates. For barley, the tissue is subcultured at an interval of about 2–3 weeks if a low level (about 0.01 mg/L) of BAP is used and about 3–4 weeks if a higher level of BAP is used (about 0.1 mg/L to about 0.5 mg/L).

Preferably, the tissues are initially cultured without selection. In Example 4 below, for example, selection was not applied immediately after bombardment in order to allow for the proliferation of transformed cells in the absence of dead or dying cells resulting from wounding or selection (about 1–2 weeks if immature embryos are used as a target source and 3–4 weeks if green tissues are used). After this period, selection is applied to select for transformed cells. Selection can be accomplished by adding a selection agent to the culture medium for which the foreign DNA in transformed cells confers resistance (assuming that a selectable marker is included on the foreign DNA). Putative transformants are identified by their faster growth on the selective medium relative to nontransformed tissue. Screenable markers (e.g., green fluorescent protein) can also be used to identify transformed tissue.

Transformed tissues preferably are maintained initially on CIM in the dark (e.g., for about 34 weeks on CIM as in Example 3), then cultured under dim light conditions (for barley, approximately 10 to 30 µE). The use of dim light conditions has been found to reduce or eliminate the regeneration of albino barley plants (as observed in Wan and Lemaux, 1994).

For barley, embryogenic structures appear as fast-growing shiny, slightly brown-colored, nodular, compact structures. Under dim light these structures often appear as multiple meristem-like structures with small green shoots. By contrast, nontransformed tissues generally lack nodular structures and appear watery, loose and friable, or round and slow-growing. After embryogenic structures are observed in the putatively transformed tissue, the tissue is transferred to an "intermediate-incubation medium" (IIM). Incubation of the tissue of an IIM permits continued rapid growth, albeit at a slower pace than CIM. Incubation on an IIM improves the likelihood of the formation of regenerative structures and competence for regeneration by promoting the transition of the developmental pathway of a plant tissue from an embryogenic route to an organogenic route.

IIM suppresses the extension of shoots and can be used to maintain and proliferate green sectors or green vegetative structures for long periods of time until they have reached sizes and numbers appropriate for regeneration (with barley, green regenerative tissues of certain genotypes can be maintained for more than ten months on DBC2 medium (the composition of which is given below), at least about eight months for Golden Promise, Galena and Harrington, and at least about four to six months for Morex, for example).

IIM preferably includes an auxin (about 0.5 mg/L to about 2.5 mg/L 2,4-D or dicamba) for continued cell proliferation. IIM preferably also includes high cytokinin concentrations (e.g., about 0.1 mg/L to about 2.0 mg/L BAP) and high copper concentrations (e.g., about 0.1 µM to about 50 µM, preferably about 5 to about 30 µM. The higher cytokinin concentration reduces the rate of cell division but promotes progress to competence for regeneration and might reduce the incidence of albinism.

Copper concentrations in the IIM are preferably at least as high as levels in MS medium (0.1 µM, Murashige and Skoog, 1962), preferably at least 5-fold higher, more preferably at least 10-fold, more preferably at least 20-fold, most preferably at least 50-fold higher. Optimal copper levels vary with the genotype and species. Higher copper levels promote improved callus quality and regenerability without reducing callus-induction frequency or the initial callus growth rate. High copper levels may have less effect or no effect when included in regeneration medium.

The term "copper" is used herein to include any well-known nutritional source of copper for plant culture media, e.g., cupric sulfate.

The effects of copper and BAP on the regenerability of transformed barley tissues appear to be more than additive, i.e., there appears to be a synergistic effect when the IIM includes both high levels of copper and high levels of BAP.

It is desirable to generate large numbers of plants from a single independently transformed callus line due to transcriptional and translational inactivation phenomena and somaclonal variation. In commercial cereals, for example, the number of transformants resulting from conventional transformation protocols has proven limiting in efforts to employ genetic engineering to achieve crop improvement. Incubation of transformed callus on an IIM prior to transfer to a regeneration medium maximizes the frequency at which individual transformation events give rise to transformed plant lines. The use of an intermediate incubation step increased the regeneration frequency for Golden Promise up to at least 65 percent and resulted in an increase in the number of transformed plants produced per callus piece of up to 11.4-fold.

Transformed tissue can be transferred from IIM to rooting or regeneration medium when embryogenic structures are observed (for barley, after about 3 or 4 rounds of subculturing or after approximately 9–16 weeks post-bombardment depending on the genotype and growth rate). The selection period should be longer when BAP is used in the CIM and IIM (about 3–4 months for Golden Promise and about 4–6 months for Galena).

"Regeneration medium" (RM) promotes differentiation of totipotent plant tissues into shoots, roots, and other organized structures and eventually into plantlets that can be transferred to soil. It is often preferable to employ a shooting medium to promote shoot regeneration from embryogenic structures and a separate rooting medium to promote root formation. Depending upon the genotype, different levels of an auxin (e.g., 2,4-D) and a cytokinin (e.g., BAP) provide optimal results. For many barley genotypes RM contains BAP (about 0–8 mg/L) without auxin. However regeneration of Morex is improved by addition of auxin (2,4-D) to the RM. Conventional shooting and rooting media are considered regeneration media.

Any well-known regeneration medium may be used for the practice of the methods of the present invention. For barley, FHG medium (Hunter, 1988, and described in Kasha et al., 1990) is preferred.

As used herein, "plant culture medium" refers to any medium used in the art for supporting viability and growth of a plant cell or tissue, or for growth of whole plant specimens. Such media commonly include defined components including, but not limited to: macronutrient compounds providing nutritional sources of nitrogen, phosphorus, potassium, sulfur, calcium, magnesium, and iron; micronutrients, such as boron, molybdenum, manganese, cobalt, zinc, copper, chlorine, and iodine; carbohydrates (preferably maltose for barley, although sucrose may be better for some species); vitamins; phytohormones; selection agents (for transformed cells or tissues, e.g., antibiotics or herbicides); and gelling agents (e.g., agr, Bactoagar, agarose, Phytagel, Gelrite, etc.); and may include undefined components, including, but not limited to: coconut milk, casein hydrolysate, yeast extract, and activated charcoal. The medium may be either solid or liquid, although solid medium is preferred.

Any conventional plant culture medium can be used as a basis for the formulation of CIM, IIM, and RM when appropriately supplemented. In addition to the media discussed in the Examples below (e.g., MS medium and FHG medium), a number of such basal plant culture media are commercially available from Sigma (St. Louis, Mo.) and other vendors in a dry (powdered) form for reconstitution with water, for example.

Any well-known auxin or cytokinin may be used in the practice of the invention. Auxins include, but are not limited to, 2,4-D, dicamba, picloram, IAA and 2,4,5-T, and NAA. Cytoknins include, but are not limited to, BAP, kinetin, zeatin, zeatin riboside, and $N^6$-(2-isopentenyl) adenine (2iP). A particular genotype or species may respond optimally to a specific phytohormone, as noted in the Examples below.

Albinism. Albinism is a common problem in barley tissue culture (Kott and Kasha, 1984; Kasha et al., 1990; Jahne et al., 1991). Albinism is influenced by a number of factors, including genetic background (Foroughi-Wehr et al., 1982), physiological state of the donor plants (Goldenstein and Kronstadt, 1986), exposure to bialaphos (Wan and Lemaux, 1994), length of time in culture (Bregitzer et al., 1995), and culture conditions (Kao et al., 1991).

Wan and Lemaux (1994) reported that, of 91 transgenic callus lines generated by particle bombardment of various target tissues, 36 lines yielded green plants and 41 yielded only albino plants. Lemaux et al., (1996) reported that, of 73 transgenic callus lines generated by particle bombardment, 37 lines yielded green plants and 20 yielded only albino plants.

The improved methods discussed herein significantly reduce the incidence of albinism below levels reported previously. Preferably, the percentage of putative transformation events that regenerate to produce green transformed barley plants (and not albino plants), i.e., the number of transformation events yielding green plants divided by the total number of transformation events yielding green and albino plants ×100 percent, is at least about 60 percent, preferably at least about 75 percent, and most preferably at least about 90 percent.

The methods described herein also reduce problems associated with induced heritable mutation and somaclonal variation that can result from long-term maintenance of plant tissue in culture.

"Plant". The term "plant" encompasses transformed plants, progeny of such transformed plants, and parts of plants, including reproductive units of a plant, fruit, flowers, seeds, etc. The transformation methods and compositions of the present invention, is applicable to various barley genotypes (e.g., Morex, Harrington, Crystal, Stander, Moravian III, Galena, Salome, Steptoe, Klages, Baronesse, etc.) as well as to other species of monocotyledonous plants (e.g., wheat, corn, rice, etc.), or dicotyledonous plants (e.g., tomato, potato, soybean, cotton, tobacco, etc.).

A "reproductive unit" of a plant is any totipotent part or tissue of the plant from which one can obtain progeny of the plant, including, for example, seeds, cuttings, tubers, buds, bulbs, somatic embryos, microspores, cultured cells (e.g., callus or suspension cultures), etc.

Nucleic Acids

"Isolated". An "isolated nucleic acid is one that has been substantially separated or purified away from other nucleic acid sequences in the cell of the organism in which the nucleic acid naturally occurs, i.e., other chromosomal and extrachromosomal DNA and RNA. The term also embraces recombinant nucleic acids and chemically synthesized nucleic acids.

"Operably Linked". Nucleic acids can be expressed in plants or plant cells under the control of an operably linked promoter that is capable of driving expression in a cell of a particular plant. A first nucleic-acid sequence is "operably" linked with a second nucleic-acid sequence when the first nucleic-acid sequence is placed in a functional relationship with the second nucleic-acid sequence. For instance, a promoter is operably linked to a coding sequence if the promoter affects the transcription or expression of the coding sequence. Generally, operably linked DNA sequences are contiguous and, where necessary, to join two protein coding regions to produce a hybrid protein.

"Recombinant". A "recombinant" nucleic acid is made by an artificial combination of two otherwise separated segments of sequence, e.g., by chemical synthesis or by the manipulation of isolated segments of nucleic acids by conventional genetic engineering techniques.

Vectors, Transformation, Host cells. Nucleic acids can be incorporated into recombinant nucleic acid constructs, typically DNA constructs, capable of being introduced into and replicating in a host cell. Such a construct preferably is a vector that includes sequences that are capable of transcription and translation of a polypeptide-encoding sequence in a given host cell (and may include a replication system, although direct DNA introduction methods conventionally used for monocot transformation do not require this).

For the practice of the present invention, conventional compositions and methods for preparing and using vectors and host cells are employed, as discussed, inter alia, in Sambrook et al., 1989, or Ausubel et al., 1992.

A number of vectors suitable for stable transformation of plant cells or for the establishment of transgenic plants have been described in, e.g., Pouwels et al., 1987, Weissbach and Weissbach, 1989, and Gelvin et al., 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Examples of constitutive plant promoters useful for expressing genes in plant cells include, but are not limited to, the cauliflower mosaic virus (CaMV) 35S promoter, maize ubiquitin (Ubi-1) promoter, rice actin (Act) promoter, nopaline synthase promoter, and the octopine synthase promoter. A variety of plant gene promoters that are regulated in response to environmental, hormonal, chemical, and/or developmental signals also can be used for expression of foreign genes in plant cells, including promoters regulated by heat (e.g., heat shock promoters), light (e.g., pea rbcS-3A or maize rbcS promoters or chlorophyll a/b-binding protein promoter); phytohormones, such as abscisic acid; wounding (e.g., wunI); anaerobiosis (e.g., Adh); and chemicals such as methyl jasminate, salicylic acid, or safeners. It may also be advantageous to employ well-known organ-specific promoters such as endosperm-, embryo-, root-, phloem-, or trichome-specific promoters, for example.

Plant expression vectors optionally include RNA processing signals, e.g., introns, which may be positioned upstream or downstream of a polypeptide-encoding sequence in the transgene. In addition, the expression vectors may also include additional regulatory sequences from the 3'-untranslated region of plant genes, e.g., a 3' terminator region to increase mRNA stability of the mRNA, such as the PI-II terminator region of potato or the octopine or nopaline synthase 3' terminator regions.

Such vectors also generally include one or more dominant selectable marker genes, including genes encoding antibiotic resistance (e.g., resistance to hygromycin, kanamycin, bleomycin, G418, streptomycin, paromomycin, or spectinomycin) and herbicide-resistance genes (e.g., resistance to phosphinothricin or glyphosate) to facilitate manipulation in bacterial systems and to select for transformed plant cells.

Screenable markers are also used for plant cell transformation, including color markers such as genes encoding β-glucuronidase (gus) or anthocyanin production, or fluorescent markers such as genes encoding luciferase or green fluorescence protein (GFP).

The invention will be better understood by reference to the following Examples, which are intended to merely illustrate the best mode now known for practicing the invention. The scope of the invention is not to be considered limited thereto.

EXAMPLES

Example 1

Improvement of Callus Quality and Regenerability in Barley Genotypes Golden Promise and Galena Materials and Methods Plant Material Donor plants for immature embryos were grown in soil under controlled conditions in growth chambers as described (Wan and Lemaux, 1994; Lemaux et al., 1996).

As noted in other Examples below, plants were grown in a greenhouse (immature embryos grown in the growth chambers are preferred for green tissue culture). The greenhouse had supplementary lighting providing a 14-h photoperiod with temperatures of 15 to 18° C. Supplemental 1000-watt metal-halide lights were engaged when the light level in the greenhouse was less than 1000 µE/ms. Roof shades covered the roof when outside light levels rose above 7000 µE/ms.

Spring cultivars of barley (*Hordeum vulgare* L.) Golden Promise and Galena were used as donor plants. Galena seed was obtained from B. Treat, Coors Brewing Company, Golden, Colo. Golden Promise seed was obtained from P. Bregitzer, USDA-ARS Small Grains Germplasm Center, Aberdeen, Id.

Media

Callus-induction medium (CIM) is MS medium (Murashige and Skoog, 1962) supplemented with 30 g/L maltose, 1.0 mg/L thiamine-HCl, 0.25 g/L myo-inositol, 1.0 g/L casein hydrolysate, 0.69 g/L proline, and solidified with 3.5 g/L Phytagel (Sigma, St. Louis, Mo.). CIM was supplemented with fourteen different combinations of two auxins (dicamba and 2,4-dichlorophenoxyacetic acid [2,4-D]) and two cytokinins (6-benzylaminopurine [BAP] and zeatin) as shown in Table 1, and the supplemental medium was tested for callus induction, callus quality, growth rate, and regenerability.

Regeneration medium (RM) is FHG medium (Hunter, 1988; Kasha et al., 1990), a modified MS medium with lower $NH_4NO$, and high glutamine, supplemented with 2 mg/L BAP and solidified with 3.0 g/L Phytagel. The composition of FHG medium is 165 mg/L $NH_4NO_3$, 1.90 g/L $KNO_3$, 440 mg/L $CaCl_2.2H_2O$, 370 mg/L $MgSO_4.7H_2O$, 170 mg/L $KH_2PO_4$, 16.9 mg/L $MnSO_4.H_2O$, 8.6 mg/L $ZnSO_4.7H_2O$, 6.2 mg/L $H_3BO_3$, 0.83 mg/L KI, 0.25 mg/L $Na_2MoO_4.2H_2O$, 25 µg/L $CuSO_4.5H_2O$, 25 µg/L $CoCl_2.7H_2O$, 0.4 mg/L thiamine-HCl, 100 mg/L inositol, 730 mg/L glutamine, 62 g/L maltose, 27.8 mg/L $FeSO_4.7H_2O$, 33.5 mg/L $Na_2EDTA$, 1.0 mg/L BAP, 3 g/L Phytagel, pH 5.6.

Callus Induction and Scoring

Immature embryos (about 1.5–2.5 mm in size) were taken from spikes approximately three months in age that were surface-sterilized in 20% (v/v) bleach (5.25% sodium hypochlorite) for 7 min. washed 5 min with sterile water three times, bisected longitudinally, and placed on CIM. Ten half-embryos were tested on CIM supplemented with each of the fourteen phytohormone combinations; each treatment had three replicates. (Whole embryos can also be used.) Callus-induction frequency was measured by counting numbers of half embryos undergoing callus induction under a light microscope 2 to 3 weeks after initial culturing.

Two embryo sizes were tested: small (0.5–1.5 mm) and large (1.5–2.0 mm). Golden Promise is good in callus induction with both small- and large-sized embryos, but callus induction is very poor with small-sized embryos of Galena.

Callus Growth Rate

For determining callus growth rates, ten half embryos were placed scutellum-side down on a Petri dish containing each medium; each treatment had three replicates. Every 2 to 3 weeks, callus pieces were weighed and the growth rate was determined by weighing the plate containing the callus pieces before transfer ($W_1$) and after transfer of all tissue ($W_2$). The relative growth of the callus was calculated as the change in weight (W) of the callus ($W=W_1-W_2$), divided by the weight of the tissues originally plated ($W_0$) and the number of culture days (g/g fresh weight/day). From the third transfer, three of the highest-quality pieces, rather than all calli from each embryo, were transferred onto fresh medium. All calli that were not transferred were removed from the plate to obtain $W_2$.

Callus Quality

Callus quality (morphology and color) was assessed microscopically 2 to 3 weeks after initial callus induction. For morphology, a score of ++++ (highest quality) was given to shiny, compact, nodular callus; a score of + (lowest quality) was given to soft, friable callus. Color was judged from slightly brown-colored callus (++++) to white (+).

Regeneration

To test regeneration, ten pieces of highest-quality callus (8 to 11 mg per piece) from each treatment were transferred to RM in three replicates at varying times during the culture period. Dishes were placed at 24±1° C. under fluorescent lights (45 to 55 mE, 16 h light/8 h dark). The number of shoots per callus piece was counted about 22–25 days after transfer. (One or more leaves arising from the same base of green tissue was considered as one shoot.)

Results

Induction Frequency, Relative Growth Rate, and Qualitative Appearance of Callus

To examine the effects of different concentrations and types of auxins and cytokinins on callus-induction frequency, quality, and relative growth rate, 14 different media were tested (Table 1, left two columns). On most media, callus-induction frequencies were not statistically different for Golden Promise and Galena; dicamba and 2,4-D alone and dicamba with zeatin at all concentrations resulted in nearly 100% induction frequencies for both genotypes. Golden Promise had a significantly higher callus-induction frequency than Galena on 3 of the 14 media tested: dicamba+0.1 mg/L BAP, dicamba+0.5 mg/L BAP, and 2,4-D+0.5 mg/L BAP. Galena had a significantly higher callus-induction frequency than Golden Promise on only one medium, 2,4-D+0.01 mg/L zeatin. With Galena, higher levels of BAP in combination with 2,4-D, or, more significantly, in combination with dicamba, led to lower callus-induction frequencies.

Callus induction from Golden Promise embryos occurred over most of the surface area of the scutellum, while Galena callus was produced from a much smaller area of the embryo.

Color assessments of the two genotypes on the same medium were identical. However, in general, callus morphology of Golden Promise was better than that of Galena on nearly all media tested (Table 1). Certain trends in morphology were seen for both genotypes.

First, culturing on medium containing BAP in combination with either 2,4-D or dicamba produced a better callus morphology than culturing on medium containing zeatin with either 2,4-D or dicamba (Table 1). Second, callus color in both genotypes was dramatically affected by the type of cytokinin (Table 1). Increasing BAP levels (with either auxin) led to the formation of more slightly brown-colored callus, whereas zeatin at all levels (with either auxin) led to the formation of poor quality, white callus (Table 1). Third, medium containing higher concentrations of BAP (0.1 to 0.5 mg/L with 2,4-D) appeared to support the production of higher quality callus (morphology and color) than did the lower concentration of BAP (0.01 mg/L) with both genotypes (Table 1).

In the first growth period, determination of the growth rate was complicated by the rapid increase in fresh weight of the starting material due to imbibition of the embryo. By the third transfer, the relative growth rate increased rapidly, reaching its maximum (FIG. 1). Growth rates dropped significantly after the fourth growth period. For both genotypes, growth rates on media containing BAP were generally slower than in the absence of BAP or in the presence of zeatin. Golden Promise appeared to grow faster than Galena on media containing dicamba plus BAP and 2,4-D+/−BAP. Both genotypes grew faster on medium containing 2,4-D plus BAP than on medium containing dicamba plus BAP (except for Galena at 0.5 mg/L BAP). There appeared to be little variation between genotypes in growth rate on medium containing 2,4-D or dicamba in combination with zeatin. The use of low concentrations of zeatin (0.01 or 0.1 mg/L) in combination with dicamba or 2,4-D did not appear to inhibit the callus growth rate of Golden Promise relative to growth on dicamba or 2,4-D alone, and the combination of low concentrations of zeatin with 2,4-D seemed to increase the callus growth rate of Galena up to the fourth growth period relative to 2,4-D alone (FIG. 1).

Plant Regeneration

Calli of Golden Promise and Galena grown on the fourteen different media were tested for their ability to regenerate plants. In general, Golden Promise produced a higher number of green calli (NC) and green shoots (NS) per 10 initial callus pieces than did Galena at most time points on most media (compare Tables 2 and 3). In addition, Galena callus appeared to lose regenerability at a faster rate than Golden Promise except on callus-induction media containing BAP in combination with 2,4-D, in which case Galena responded more favorably than Golden Promise at all levels of BAP.

For Golden Promise (Table 2), through the fifth transfer all treatments produced comparable numbers of green calli, while 2,4-D plus 0.01 and 0.5 mg/L BAP appeared to yield the highest numbers of shoots. In most cases the number of shoots and green calli decreased dramatically after either the fifth or seventh transfers. One of the most dramatic losses was at the seventh transfer with the use of dicamba alone, where no green calli were observed. Few media supported the regeneration of plants at the ninth transfer. Only dicamba and 2,4-D plus 0.1 mg/L BAP and 2,4-D plus 0.5 mg/L zeatin supported long-term shoot regenerability in Golden Promise.

For Galena (Table 3), on medium containing either (1) dicamba or 2,4-D with zeatin or (2) dicamba in combination with BAP, the ability to generate green shoots was lost more rapidly than with Golden Promise. The only media supporting long-term maintenance of greening and regeneration of plants ($7^{th}$ transfer and beyond) was 2,4D plus BAP at all levels. Media containing 0.1 mg/L BAP appeared optimal at the latest time point and supported a faster callus growth rate than dicamba plus a comparable level of BAP (FIG. 1).

For both genotypes, medium containing BAP in combination with 2,4,-D (and to a lesser extent dicamba) supported the development of multiple shoots from the shiny, compact callus tissues (Tables 1–3), while few or no shoots developed on a medium containing 2,4-D alone.

Discussion

In these experiments, medium composition and phytohormone types and levels were important factors in determining tissue culture responses. Certain generalizations can be made regarding the effects of different cytokinins on the properties of proliferated callus. Although medium containing zeatin appeared to support faster growth rates, medium containing zeatin (plus 2,4-D or dicamba) also produced lower quality (soft, light-colored) callus compared to medium containing BAP (plus 2,4-D or dicamba) (Table 1).

The detrimental effects of zeatin can also be seen by comparing the regenerative potential of calli from both genotypes grown on medium including either BAP or zeatin. Calli grown on medium containing zeatin (from 0.01 to 0.5 mg/L) were less regenerative than calli grown on medium containing BAP and regenerated on the same RM (Tables 2 and 3). This finding is in contrast to that of Lörz and Lörz (*Theor, Appl. Genet.*, 75:16–25, 1987), who showed that, in combination with IAA, zeatin and zeatin riboside (0.05 mg/L increased the frequency of regeneration. Other cytokinins, such as BAP, kinetin, and 2iP, were shown to cause callus browning and necrosis of somatic embryos. Media containing IAA and zeatin has also been shown to improve regenerability of immature embroy-derived callus of *Hordeum spontaneum* and *H. bulbosum* (Breimann, *Plant Cell Rep.*, 4:161–163, 1985). The fact that we did not observe a positive effect of zeatin on the tissue culture response of Golden Promise and Galena may result from the particular barley genotypes, the different auxins (dicamba and 2,4-D) we employed, or other modifications in our culturing procedures.

In contrast to zeatin, the addition of BAP to 2,4-D-containing medium decreased the growth of the soft, friable callus and increased the frequency of embryogenic, shiny, compact and slightly brown-colored callus that was more highly regenerative (Table 1). In many cases, calli grown on media containing low concentrations of BAP (0.01 or 0.1 mg/L) in combination with 2,4-D yielded the largest numbers of regenerated shoots for a particular genotype; with Galena, 2,4-D+BAP prolonged the regeneration period for green plants. The auxin 2,4-D is most commonly used for embryogenic callus formation in cereal crops, but the addition of cytokinin to 2,4-D can be significant, depending on plant species and genotypes (reviewed by Bhaskaran and Smith, *Crop Sci.*, 30:1328–1336, 1990). Recently, multiple shoots were differentiated from excised shoot apical meristems in maize (Zhong et al., *Planta*, 187:483–489, 1992) and oat (Zhang et al., *J. Plant Physiol.*, 148: 667–671, 1996) cultured on BAP and 2,4-D. This effect of BAP on shoot regeneration is also consistent with previous observations on Kentucky bluegrass (Griffin and Dibble, *Plant Cell Rep.*, 14:721–724, 1995) and creeping bentgrass (Zhong et al., *Plant Cell Rep.*, 10:453–456, 1991), where higher frequencies of shoot regeneration from seed-derived callus were achieved when auxin (dicamba or 2,4-D) and BAP were substituted for auxin alone.

In our study the positive effect of BAP in combination with 2,4-D was also reflected in callus quality (Table 1). Shiny, compact and slightly brown-colored callus produced green plants. Compact, light-colored callus was regenerative but generally produced albino plants. Soft, friable callus was not regenerative. For both Golden Promise and Galena, the addition of BAP (in combination with either 2,4-D or dicamba) decreased the growth of the soft, friable, white callus and increased the proportion of compact, slightly brown-colored regenerative callus relative to no cytokinin or comparable concentrations of zeatin (Table 1).

Golden Promise calli grown on medium containing 0.01 mg/L BAP in combination with 2,4-D regenerated almost the largest (fourth/seventh transfers) or equivalent (fifth) numbers of green shoots relative to the other media (Table 2). Calli grown on medium containing 0.1 mg/L BAP with 2,4-D produced fewer (and shorter) green shoots than media with 0.01 mg/L at all but the third and ninth transfers (Table 2). For Galena, growth on medium containing 2,4-D with 0.1 mg/L of BAP produced callus that yielded the most green plants at all transfer times except the third (Table 3). When calli with small, green, compact shoots were transferred for the second time from medium containing 2,4-D and 0.1 mg/L BAP onto fresh regeneration medium, more tissue containing multiple shoots was seen than when 0.01 mg/L BAP was used. It is possible that the BAP-containing medium caused the callus tissue to proliferate for prolonged periods in the regenerable state.

The negative effects of the length of time in culture on regenerative potential is also documented in this study. On all media, immature embryos of Golden Promise produced fast-growing, embryogenic callus that gave rise to green plants at high frequencies for periods up to two months (fifth transfer) after initial callus induction (Table 1 and 2; FIG. 1). After the fifth transfer, Golden Promise calli began to lose regenerative potential (Table 2). Galena lost regenerability much more rapidly than Golden Promise on all media tested, except for media containing 2,4-D plus BAP (Table 3), with regenerability declining on most media after the fourth transfer. Therefore, long periods of culturing in the dark led to lower total numbers of regenerated green plants from both Golden Promise and Galena (Tables 2 and 3), with the losses in Galena being more marked.

Culture time also appeared to affect albinism. There was a small number of green calli in Galena cultures relative to Golden Promise at later time points (seventh, ninth) on most media (Tables 2 and 3). Some albino plants were produced from Golden Promise at later transfer times. However, when cultured on the same medium for the same length of time, Galena produced larger numbers of albino plants. The propensity of Galena toward albinism is also supported by data collected during regeneration tests of 1-month-old Golden Promise and Galena calli grown on 2,4-D (2.5 mg/L) in combination with BAP r=(o.1 mg/L). From this material, 70 to 80% of the GP cells became green under dim light conditions (10 to 20 µE), whereas less than 20% of the cells from a comparably aged Galena culture had greening potential.

Thus, the length of time in culture and genotypic differences have dramatic effects on albinism and hence on the ability to regenerate green plants.

Embryo size is another important factor affecting callus-induction frequencies. Optimal embryo size varies with genotype. Using embryo sizes larger than 2.5 mm from both genotypes resulted in low callus-induction frequencies. Galena embryos from 0.5 to 1.2 mm in size had very low callus-induction frequencies (<20%) while Golden Promise embryos of the same size had a frequency of over 90%. The highest callus-induction frequencies with Golden Promise were associated with calli from 0.5 to 2.0 mm in size, while the optimal size for Galena was 1.5 to 2.0 mm. The effect of size on callus-induction frequency is likely due to the effects of the exogenously applied hormones on the developmental cascades that are triggered in a particular sized, immature embryo and the developmental flexibility of the particular genotype.

The frequency of induction, quality, and regenerability of callus in barley are influenced by a variety of factors, such as media composition (Bregitzer, 1992; Dahleen, 1995; Handel et al., 1985; Lörz and Lörz, 1987), phytohormones (Hagio et al., 1995; Ziauddin and Kasha, 1990; Lörz and Lörz, 1987), length of time in culture (Lörz and Lörz, 1987; Bregitzer et al., 1995), embryo size (Baillie et al., 1993; Ziauddin and Kasha, 1990; Dale and Dambrogio, 1979), and genotype (Dahleen, 1996; Baillie et al., 1993; Bregitzer, 1992; Lörz and Lörz, 1987; Goldenstein and Kronstadt, 1986; Handel et al., 1985). We have confirmed and expanded these observations to the transformable barley cultivar Golden Promise and recalcitrant commercial barley variety, Galena.

Using a previously published transformation protocol that employed a medium containing 2.5 mg/L dicamba and no cytokinin (Wan and Lemaux, 1994), we obtained large numbers of transformed callus lines with Galena, but all lines yielded only albino plants. We have identified optimal combinations and levels of auxin and cytokinin for production of the highest quality, regenerative callus of Golden Promise and Galena during prolonged tissue culture periods. For both genotypes, 2,4-D in combination with BAP (between about 0.01 and about 0.1 mg/L) was found to be optimal for prolonging regenerability and producing the highest numbers of green calli and shoots. These phytohormone conditions can be adjusted for optimal results with other barley genotypes and for other plant species as well.

TABLE 1

Callus-induction Frequency and Qualitative Appearance of Golden Promise and Galena

| | Auxin Conc. | Cytokinin Conc. | Callus Induction Frequency (%)[a] | | Callus Morphology[d] | | Callus Color[e] | |
|---|---|---|---|---|---|---|---|---|
| | (mg/L) | (mg/L) | GP[b] | GAL[c] | GP | GAL | GP | GAL |
| | Dicamba | BAP | | | | | | |
| (1) | 2.5 | 0 | 100 ± 0 | 100 ± 0 | +++(+) | + | ++ | + |
| (2) | 2.5 | 0.01 | 96.3 ± 5.2 | 92.6 ± 5.2 | +++ | +(+) | ++ | ++ |
| (3) | 2.5 | 0.1 | 88.9 ± 0 | 71.3 ± 12.4 | +++ | ++ | ++ | ++ |
| (4) | 2.5 | 0.5 | 92.6 ± 5.2 | 54.2 ± 5.9 | +++ | +++ | +++ | +++ |
| | 2,4-D | BAP | | | | | | |
| (5) | 2.5 | 0 | 92.6 ± 5.2 | 100 ± 0 | +++ | +(+) | ++ | ++ |
| (6) | 2.5 | 0.01 | 100 ± 0 | 96.3 ± 5.2 | +++(+) | ++ | +++ | +++ |
| (7) | 2.5 | 0.1 | 84.3 ± 6.6 | 84.3 ± 6.6 | ++++ | +++ | ++++ | ++++ |
| (8) | 2.5 | 0.5 | 92.6 ± 5.2 | 75.0 ± 0 | ++++ | +++ | ++++ | ++++ |
| | Dicamba | Zeatin | | | | | | |
| (9) | 2.5 | 0.01 | 100 ± 0 | 96.3 ± 5.2 | ++ | + | + | + |
| (10) | 2.5 | 0.1 | 100 ± 0 | 100 ± 0 | +++ | ++ | + | + |
| (11) | 2.5 | 0.5 | 100 ± 0 | 100 ± 0 | ++ | + | + | + |
| | 2,4-D | Zeatin | | | | | | |
| (12) | 2.5 | 0.01 | 79.6 ± 6.6 | 100 ± 0 | ++ | + | + | + |
| (13) | 2.5 | 0.1 | 88.0 ± 10.2 | 88.9 ± 0 | +(+) | +(+) | + | + |
| (14) | 2.5 | 0.5 | 100 ± 0 | 100 ± 0 | ++ | + | + | + |

[a]Values represent means ± standard deviation of three replicates for each treatment.
[b]GP represents Golden Promise.
[c]GAL represents Galena.
[d]Morphology includes the degree of compactness and shine, from ++++, being the most compact and shiny callus to +, being the least compact and shiny callus.
[e]Color is from slight brown (++++) to white (+).

TABLE 2

Regeneration of Golden Promise Calli Grown on CIM with Different Combinations of Auxins and Cytokinins

| Auxin Conc. | Cytokinin conc. | 3rd Transfer | | 4th Transfer | | 5th Transfer | | 7th Transfer | | 9th Transfer | |
|---|---|---|---|---|---|---|---|---|---|---|---|
| (mg/L) | (mg/L) | NS[a] | NC[b] | NS | NC | NS | NC | NS | NC | NS | NC |
| Dicamba | BAP | | | | | | | | | | |
| 2.5 | 0 | 189 | 10 | 134 | 10 | 122 | 7 | 0 | 0 | 0 | 0 |
| 2.5 | 0.01 | 186 | 10 | 190 | 10 | 163 | 10 | 5 | 1 | 0 | 0 |
| 2.5 | 0.1 | 134 | 10 | 90 | 10 | 138 | 10 | 68 | 7 | 5 | 2 |
| 2.5 | 0.5 | 88 | 10 | 100 | 10 | 62 | 10 | 25 | 4 | 0 | 1 |
| 2,4-D | BAP | | | | | | | | | | |
| 2.5 | 0 | 140 | 10 | 140 | 9 | 91 | 6 | 37 | 4 | 0 | 0 |
| 2.5 | 0.01 | 146 | 10 | 175 | 10 | 216 | 10 | 51 | 9 | 0 | 0 |
| 2.5 | 0.1 | 213 | 10 | 120 | 9 | 85 | 7 | 17 | 4 | 7 | 7 |
| 2.5 | 0.5 | 139 | 10 | 127 | 10 | 219 | 10 | 22 | 6 | 0 | 0 |

TABLE 2-continued

Regeneration of Golden Promise Calli Grown on
CIM with Different Combinations of Auxins and Cytokinins

| Auxin Conc. (mg/L) | Cytokinin conc. (mg/L) | 3rd Transfer NS[a] | 3rd Transfer NC[b] | 4th Transfer NS | 4th Transfer NC | 5th Transfer NS | 5th Transfer NC | 7th Transfer NS | 7th Transfer NC | 9th Transfer NS | 9th Transfer NC |
|---|---|---|---|---|---|---|---|---|---|---|---|
| Dicamba | Zeatin | | | | | | | | | | |
| 2.5 | 0.01 | 204 | 10 | 138 | 10 | 87 | 6 | 44 | 3 | 0 | 0 |
| 2.5 | 0.1 | 186 | 9 | 120 | 10 | 94 | 8 | 0 | 1 | 0 | 0 |
| 2.5 | 0.5 | 114 | 10 | 89 | 10 | 139 | 8 | 34 | 7 | 0 | 0 |
| 2,4-D | Zeatin | | | | | | | | | | |
| 2.5 | 0.01 | 165 | 10 | 125 | 10 | 90 | 8 | 81 | 7 | 0 | 0 |
| 2.5 | 0.1 | 87 | 10 | 121 | 8 | 88 | 6 | 41 | 4 | 0 | 0 |
| 2.5 | 0.5 | 105 | 10 | 141 | 10 | 56 | 7 | 52 | 6 | 2 | 3 |

[a]NS = number of green shoots from 10 initial calli.
[b]NC = number of green calli from 10 initial calli.

TABLE 3

Regeneration of
Galena Calli Grown on CIM with Different Combinations of Auxins and Cytokinins

| Auxin Conc. (mg/L) | Cytokinin conc. (mg/L) | 3rd Transfer NS[a] | 3rd Transfer NC[b] | 4th Transfer NS | 4th Transfer NC | 5th Transfer NS | 5th Transfer NC | 7th Transfer NS | 7th Transfer NC | 9th Transfer NS | 9th Transfer NC |
|---|---|---|---|---|---|---|---|---|---|---|---|
| Dicamba | BAP | | | | | | | | | | |
| 2.5 | 0 | 60 | 7 | 63 | 9 | 15 | 2 | 0 | 0 | 0 | 0 |
| 2.5 | 0.01 | 54 | 7 | 52 | 9 | 0 | 0 | 0 | 0 | 0 | 0 |
| 2.5 | 0.1 | 22 | 9 | 31 | 10 | 1 | 2 | 0 | 0 | 0 | 0 |
| 2.5 | 0.5 | 22 | 8 | 19 | 4 | 43 | 7 | 0 | 6 | 0 | 0 |
| 2,4-D | BAP | | | | | | | | | | |
| 2.5 | 0 | 2 | 1 | 4 | 1 | 27 | 7 | 0 | 0 | 0 | 0 |
| 2.5 | 0.01 | 46 | 8 | 22 | 7 | 24 | 6 | 11 | 1 | 13 | 1 |
| 2.5 | 0.1 | 18 | 10 | 105 | 9 | 65 | 7 | 24 | 2 | 26 | 4 |
| 2.5 | 0.5 | 30 | 6 | 57 | 10 | 39 | 5 | 13 | 5 | 6 | 6 |
| Dicamba | Zeatin | | | | | | | | | | |
| 2.5 | 0.01 | 36 | 9 | 68 | 8 | 0 | 10 | 0 | 0 | 0 | 0 |
| 2.5 | 0.1 | 39 | 7 | 12 | 3 | 0 | 10 | 0 | 0 | 0 | 0 |
| 2.5 | 0.5 | 7 | 7 | 5 | 2 | 0 | 10 | 0 | 0 | 0 | 0 |
| 2,4-D | Zeatin | | | | | | | | | | |
| 2.5 | 0.01 | 19 | 3 | 42 | 5 | 28 | 5 | 0 | 0 | 0 | 0 |
| 2.5 | 0.1 | 36 | 5 | 25 | 5 | 0 | 10 | 0 | 0 | 1 | 0 |
| 2.5 | 0.5 | 6 | 2 | 4 | 2 | 4 | 8 | 0 | 0 | 0 | 0 |

[a]NS is the number of green shoots from 10 initial calli.
[b]NC is the number of green calli from 10 initial calli.

Example 2

High-Frequency Plant Regeneration from Transgenic and Nontransgenic Callus Tissues of Barley Materials and Methods Callus Induction and Maintenance Callus induction was performed as described above using CIM with 2.5 mg/L of 2,4-D or dicamba (no cytokinin). After incubation for three weeks at 24±1° C. in the dark, callus was cut into small pieces (about 3 to 4 mm), then maintained on the same medium with subculturing at three-week intervals.

Plasmids

Plasmid ppGlbGus-6 (Liu, 1994) contains the uidA (gus) reporter gene under the control of the maize embryo-specific globulin (Glb1) promoter (containing 1.38 kb upstream of the transcription start site) and terminated by the Agrobacterium tumefaciens nopaline synthase 3' polyadenylation signal (nos). Plasmid pdG1bGUS-6 was constructed by (1) digesting ppGlblGUS with EcoRI to obtain a 2.54-kb fragment containing 0.37-kb of the globulin promoter, uidA reporter gene and nos terminator, and (2) ligating the 2.54-kb fragment into the vector pUC19. Plasmid pAHC20 contains the bar gene from Streptomyces hygroscopicus under the control of the maize ubiquitin Ubi1 promoter and first intron (Christensen and Quail, 1996) and followed by the 3'-untranslated region and nos.

Microprojectile Bombardment and Transformation

Barley transformation via microparticle bombardment was carried out as described (Wan and Lemaux, 1994).

Regeneration Via an Intermediate-Incubation Step

Ten pieces of two-month-old nontransgenic calli grown on CIM supplemented with either 2,4-D or dicamba in the dark were transferred to RM either directly or following incubation on an IIM.

Two different IIM were used, DBC2 and DBC3. DBC2 medium is CIM containing 2.5 mg/L 2,4-D, 0.1 mg/L BAP, and 5.0 µM copper (cupric sulfate). DBC3 medium is CIM containing 1.0 mg/L 2,4-D, 0.5 mg/L BAP, and 5.0 µM copper. After growing calli on these media for 3–4 weeks under dim light conditions (20 to 30 µE; 16 h light/8 h dark), the numbers of calli producing green sectors or green regenerative structures were counted. Green sectors and small green regenerative structures were then transferred to fresh RM and grown under higher light intensity (45–55 µE). After 3–4 weeks, the numbers of green shoots per callus piece were counted. For regeneration of transgenic callus lines, seven to ten pieces of transgenic calli were either transferred directly to each medium (containing 4–5 mg/L bialaphos) or transferred after an incubation on an IIM, then grown under the same conditions as described above for nontransgenic calli. Each treatment included four replicates of the regeneration test for nontransgenic calli but one replicate for transgenic calli.

Results

Transgenic calli and nontransgenic calli grown on the CIM with and without bialaphos, respectively, were transferred onto RM either directly or after incubation on an IIM. There was no significant difference among treatments in numbers of nontransgenic and transgenic calli of Golden Promise producing green sectors 34 weeks after transfer (Tables 4 and 6). Multiple green shoots were induced from both transgenic and nontransgenic calli when either DBC2 or DBC3 was used as an IIM. Incubation on an IIM resulted in multiple green structures from 2,4-D and BAP and even more structures from the treatment including elevated levels of copper. Calli on either DBC2 or DBC3 formed multiple green shoots from the meristem-like structures; no albino plants were observed. Most of the green sectors that arose directly on RM without an intermediate incubation step regenerated fewer than two shoots per green sector, while green sectors grown on an IIM produced 2–5 shoots per green sector (Table 4). CIM containing 2,4-D was better in green-shoot regeneration than callus from medium containing dicamba (Table 4). The frequency of shoot regeneration was increased 5.6-fold to 6.4-fold for nontransgenic calli initiated and maintained on BCI-DM (barley callus-induction medium [Wan and Lemaux, 1994] containing 2.5 mg/L dicamba) with the use of an intermediate-incubation step (Table 4). Calli grown on BCI-2,4-D (barley callus induction medium [Wan and Lemaux, 1994] containing 2.5 mg/L 2,4-D) displayed a shoot regeneration frequency that was increased approximately 2.3-fold to 3.4-fold in response to the intermediate-incubation step. However, plantlets regenerated directly on RM grew faster than plantlets grown with an intermediate-incubation step.

Five independent transgenic lines at the fourth to sixth round of selection were tested for green shoot regeneration with or without an intermediate-incubation step (Table 6). The transgenic lines were obtained on selection medium (BCI-DM plus 5 mg/L bialaphos) then transferred onto FHG (+4 mg/L bialaphos) with or without an intermediate step. After 34 weeks, numbers of green spots were counted and regenerative tissues were transferred onto fresh FHG medium (+4 mg/L bialaphos). After an additional three weeks, numbers of green shoots were counted. The regenerability of green shoots varied depending upon the transgenic line; however, the frequency of green shoot regeneration from transgenic calli cultured with an intermediate-incubation step increased 2.8- to 11.4-fold (Table 6). Only line GPG1bGUS-13 line did not produce any green plants, even with an intermediate-incubation step.

Discussion

In this study, two different media, DBC2 and DBC3, were used for an intermediate-incubation step to improve the regenerability of transgenic and nontransgenic callus tissues of Golden Promise. No significant difference was detected among treatments in terms of numbers of transgenic and nontransgenic calli producing green sectors (Tables 4 and 6). However, transfer of tissue onto DBC2 or DBC3 induced the formation of multiple green structures, ultimately resulting in a greater number of plants from each piece.

Calli grown on callus-induction medium containing auxin alone (either 2,4-D or dicamba) produce green sectors or green structures from only small areas of each callus culture. In many cases, these green sectors do not generate plantlets on RM, possibly due to insufficient numbers of cells being generated on RM to give rise to entire plantlets. If an intermediate incubation step is used, the number of green sectors or structures that generate plantlets is increased. The use of 2,4-D in combination with BAP in the intermediate step might improve regeneration by allowing proliferation of green, totipotent cells capable of producing plants.

Nontransgenic barley callus grown on callus-induction medium containing 2,4-D or dicamba alone and transgenic callus selected on CIM containing dicamba and bialaphos produce multiple shoot meristem-like structures when subsequently transferred to intermediate incubation medium containing BAP, 2,4-D, and copper (50×) under dim light conditions (Tables 4 and 6). These meristem-like structures subsequently produce multiple shoots. In contrast, medium containing BAP alone produces only one or a few shoots per green sector. Thus, an IIM containing an appropriate auxin, BAP, and copper to treat callus promotes the production of multiple green meristem-like structures and resultant plantlets.

No significant difference in regenerability between DBC2 and DBC3 (Tables 4 and 6) is observed; rather, the callus structure itself determined the outcome. In general, DBC2 medium is more appropriate for callus with smaller-sized green sectors than DBC3 medium. DBC2 medium inhibits the growth of shoots, but green sectors or green structures can be maintained and proliferated on this medium for a long period of time until they have achieved a size appropriate for regeneration. Green tissues of Golden Promise, Galena, Harrington, and Salome, for example, can be maintained for more than 10 months (more than 4–6 months for Morex). These tissues produce multiple green shoots with a range of 9–17 shoots per piece of green tissue 4–6 mm in size. When germinating tissues were broken into 3–4 pieces after 3–4 weeks on RM and transferred to fresh medium, an even greater number of shoots were produced from the small embryogenic structures in which no shoots had yet formed.

Although the use of the intermediate-incubation step increased regenerability, there were still transformation events which were not regenerable. For example, the GPG1bGUS-13 transgenic line did not produce any green plants, possibly due to either transformation of a single original nonregenerable cell or to the early loss of regenerability during culturing of the callus. The use of an intermediate-incubation step as early as possible during the regeneration procedure also reduced the incidence of albinism. By applying this intermediate-incubation step at earlier selection stages, we obtained green, transgenic plants from a recalcitrant commercial cultivar called Galena, a result that was unachievable using published procedures.

Compared to earlier methods (Wan and Lemaux, 1994), the use of an intermediate-incubation step increased the frequency of shoot regeneration about 2.3-fold to about 11.4-fold for the nontransgenic and transgenic calli of Golden Promise and improved the culturability and regenerability of other recalcitrant commercially important genotypes, such as the North American malting cultivars Harrington and Morex (see Table 5).

TABLE 4

Regeneration of Nontransgenic Callus Tissues of Golden Promise

| Maintenance Medium | Intermediate Step | Regeneration Medium | Calli w/ green spots per Calli tested | Green shoots per callus piece |
|---|---|---|---|---|
| BCI-DM | FHG | FHG | 4.8 ± 3.6/10 | 0.35 ± 0.13 (100%) |
|  | DBC2 | FHG | 5.5 ± 3.0/10 | 1.95 ± 0.26 (557%) |
|  | DBC3 | FHG | 7.3 ± 1.0/10 | 2.23 ± 0.29 (637%) |
| BCI-2,4-D | FHG | FHG | 7.5 ± 1.7/10 | 1.15 ± 0.30 (100%) |
|  | DBC2 | FHG | 7.8 ± 2.1/10 | 3.88 ± 1.36 (337%) |
|  | DBC3 | FHG | 8.5 ± 0.6/10 | 2.6 ± 0.52 (229%) |

TABLE 5

Regeneration of Nontransgenic Callus Tissues of Morex

| Maintenance Medium | Intermed. Step | Regener. Medium | Calli with Green Spots/ Calli Tested | Shoots/ Callus Piece Green | Shoots/ Callus Piece Albino |
|---|---|---|---|---|---|
| BCI-2,4-D | FHG | FHG | 3.3/7 | 0 | 0 |
|  | DBC2 | FHG | 3.7/7 | 0.29 | 0.24 |

TABLE 6

Regeneration of Transgenic Callus Tissues of Golden Promise

| Transgenic Line | Intermediate Step | Regeneration Medium | No. of calli w/green spots /No. of calli tested | No. of green shoots per callus |
|---|---|---|---|---|
| GPGlbGUS-6 | FHG | FHG | 6/10 | 0.1 (100%) |
|  | DBC2[a] | FHG | 6/10 | 0.7 (700%) |
|  | DBC3[b] | FHG | 7/10 | 0.4 (400%) |
| GPGlbGUS-7 | FHG | FHG | 6/7 | 0.43 (100%) |
|  | DBC2 | FHG | 6/7 | 1.57 (365%) |
|  | DBC3 | FHG | 4/7 | 3.29 (765%) |
| GPGLbGUS-13 | FHG | FHG | 0/10 | 0.0 (0%) |
|  | DBC2 | FHG | 0/10 | 0.0 (0%) |
|  | DBC3 | FHG | 0/10 | 0.0 (0%) |
| GPdGGUS-5 | FHG | FHG | 10/10 | 1.0 (100%) |
|  | DBC2 | FHG | 10/10 | 4.9 (490%) |
|  | DBC3 | FHG | 9/10 | 11.4 (1140%) |
| GPdGGUS-8 | FHG | FHG | 6/7 | 0.57 (100%) |
|  | DBC2 | FHG | 5/7 | 2.14 (375%) |
|  | DBC3 | FHG | 3/7 | 1.57 (275%) |

[a]DBC2 is CIM containing 2.5 mg/L 2,4-D, 0.1 mg/L BAP, 5.0 μM copper, plus 4 mg/L bialaphos.
[b]DBC3 is CIM containing 1.0 mg/L 2,4-D, 0.5 mg/L BAP, 5.0 μM copper, plus 4 mg/L bialaphos).

Example 3

Reduction of Genotype Limitation and Albinism: Transformation of Barley Phenotype Golden Promise and the Recalcitrant Barley Genotype Galena Materials and Methods Plant Material Donor plants for immature embryos were grown in soil under controlled conditions in growth chambers as described (Wan and Lemaux, 1994; Lemaux et al., 1996) or in the greenhouse, as noted (immature embryos grown in the growth chambers are preferred for green tissue culture, although it is not necessary to use greenhouse-grown plant material).

The greenhouse had supplementary lighting providing a 14-h photoperiod with temperatures of 15 to 18° C. Supplemental 1000-watt metal-halide lights were engaged when the light level in the greenhouse was less than 1000 μE/ms. Roof shades covered the roof when outside light levels rose above 7000 μE/ms.

Callus Induction and Green Embryogenic Tissue Production

Immature zygotic embryos about 1.5 to 2.5 mm in size were dissected and isolated intact under a stereo dissecting microscope from seeds that were surface-sterilized for 10 min in 20% (v/v) bleach (5.25% sodium hypochlorite) followed by three washes in sterile water. The embryos were placed scutellum-side down on CIM.

Six different CIMs were used to test callus-induction frequencies and callus quality. The CIMs had, respectively, different concentrations of: 2,4-D (1.0 and 2.5 mg/L), BAP (0.01, 0.1 and 0.5 mg/L), and cupric sulfate ($CuSO_4$; 0.1 and 5.0 μM) as shown in Table 7.

DBC1 medium, which is CIM with 2.5 mg/L 2,4-D, 0.01 mg/L BAP, and 5.0 μM $CuSO_4$, was used for the initial callus-induction period with Golden Promise. DBC2 medium was used for the initial callus-induction period with Galena and Salome.

Five to seven days after callus initiation, germinating shoots and roots were removed from the callusing scutellum by manual excision. After 3–4 weeks' initial incubation in the dark at 24±1° C., embryogenic callus from the scutellum was cut into small pieces (about 3–4 mm), transferred to fresh DBC2 medium (Golden Promise and Galena), and grown under dim light conditions (approximately 10 to 20 μE, 16 h-light). After an additional three weeks (at the second transfer), green callusing sectors were selected, broken into two to three pieces (each about 3–4 mm in size) and transferred to fresh DBC2 medium.

Green regenerative tissues from Golden Promise and Salome were maintained on DBC2 medium, subculturing at three to four-week intervals.

DBC3 medium was used from the second transfer for Galena and subculturing took place at three- to four-week intervals.

Plant Regeneration

Seven pieces of four-month-old green regenerative tissue (about 4–6 mm) were plated on solid RM and exposed to a light intensity of approximately 30 to 50 μE. After 25 days, the numbers of green tissues that produced shoots and the numbers of shoots per piece of green tissue were counted. A single base of green tissue with more than one leaf was considered as one shoot.

Regenerated shoots were transferred to rooting medium (CI medium without hormones) in Magenta® boxes (Magenta Corporation, Chicago, Ill.). When the shoot reached the top of the box (approximately 3–4 weeks), plantlets were transferred to 6-inch pots containing Supersoil™ (R. McClellan, S. San Francisco, Calif.), gradually acclimatized, and grown to maturity in the greenhouse.

Plasmid

Plasmid pAHC25 includes the uidA (gus) reporter gene and a selectable gene, bar, each under control of the maize ubiquitin Ubi1 promoter and intron 1 and terminated by nos (Christensen and Quail, 1996).

DNA Particle Bombardment

Intact barley embryos were surface-sterilized, placed scutellum-side down, and grown on CIM, either supplemented with 2.5 mg/L 2,4-D and 5.0 µM $CuSO_4$ (DC medium) or supplemented with 2.5 mg/L 2,4-D and 0.1 µM $CuSO_4$ (D medium).

One day after excision of Galena embryos at 24±1° C. in the dark, the embryos were transferred scutellum-side up for osmotic pretreatment on CIM containing no maltose but including 0.2 M mannitol and 0.2 M sorbitol. Four hours after treatment with the osmoticum, the embryos were bombarded as described (Lemaux et al., 1996). Briefly, this involved the coating of 1 µm gold particles (Analytical Scientific Instruments, Alameda, Calif.) with plasmid DNA followed by bombardment using a PDS-1000 He biolistic device (Bio-Rad, Inc., Hercules, Calif.) at 900 psi. 16–18 hours after bombardment, the embryos were placed scutellum-side down on DC medium (no bialaphos) and grown at 24±1° C. in the dark for 10–14 days.

Selection and Regeneration of Transformed Tissue

Following an initial 10- to 14-day culturing period, each callusing embryo was broken into two or three pieces (approximately 4–5 mm each), depending on callus size, transferred to DBC2 medium supplemented with 4 mg/L bialaphos, and incubated in the dark. Two weeks after the second transfer (first-round selection), callus was transferred to new DBC2 medium containing 4 mg/L bialaphos, and 7 to 14 days later, calli were moved to dim light conditions (about 10 µE, 16 h-light). Through the fourth transfer, calli were maintained on the same medium. At the fifth transfer, calli were moved to DBC3 medium supplemented with 4 mg/L bialaphos. Cultures were subcultured at two-week intervals on DBC3 medium with 4 mg/L bialaphos until formation of green structures occurred, at which time they were plated on solid RM containing 3 mg/L bialaphos for regeneration and exposed to higher intensity light (approximately 30–50 µE). After 3–4 weeks on RM, regenerated shoots were transferred to Magenta® boxes containing rooting medium (CI medium containing 0.1 µM copper without hormones) supplemented with 2–3 mg/L bialaphos. When the shoots reached the top of the box, plantlets were treated as described above.

Histochemical GUS Assay

GUS activity was assayed histochemically as described (Jefferson et al., 1987).

PCR Assay

Polymerase chain reaction (PCR) analysis was carried out using genomic DNA extracted from calli or leaves. Two sets of primers were used for confirming the presence of the bar gene, Bar5F and Bar1 R (Lemaux et al., 1996). Another set of primers was used for confirming the presence of the gus gene, uidA1 and uidA2R (Cho et al., 1996). Amplifications were performed in a 25 µL reaction volume containing 10×PCR buffer, 25 mM $MgCl_2$, 2.5 mM dNTPs, 20 µM each primer, with 0.25 µL Taq DNA polymerase (Promega). Cycling was controlled by a thermal cycler programmed with the following conditions: 1 min denaturation step at 94° C.; 10 cycles at: 94° C. for 45 sec, 60° C. for 0.1–0.5 min/cycle, 72° C. for 1 min; and 26 cycles at: 94° C. for 45 sec, 55° C. for 1 min, 72° C. for 1 min. For the final cycle, the duration of the extension step was 7 min at 72° C. 25 µL of the PCR product with loading dye was electrophoresed on a 0.8% agarose gel with ethidium bromide and detected by UV light.

DNA Hybridization Analysis

Genomic DNA isolated from leaf tissue of a nontransformed control plant and $T_0$ and $T_1$ plants of transgenic lines was digested with XbaI and either SacI or PstI. Digested with XbaI and SacI releases an intact 1.8 kb uidA (gus) fragment; digestion with XbaI and PstI releases an intact 0.6 kb bar fragment. For gel electrophoresis, each lane was loaded with 10 µg of each digest. After Southern transfer, the resulting blot was hybridized with a $^{32}P$-labeled uidA or bar probe.

Results

Initial Callus Induction and Growth

The initial callus-induction frequency was determined using CIM of different compositions. Ten immature embryos from the barley genotypes Golden Promise and Galena were transferred to each CIM. Each CIM contained the following levels of hormones and copper: D, 2.5 mg/L 2,4-D and 0.1 µM $CuSO_4$; DC, 2.5 mg/L 2,4-D and 5.0 µM $CuSO_4$; DB, 2.5 mg/L 2,4-D, 0.1 mg/L BAP, 0.1 µM $CuSO_4$; DBC1, 2.5 mg/L 2,4-D, 0.01 mg/L BAP and 5.0 µM $CuSO_4$; DBC2, 2.5 mg/L 2,4-D, 0.1 mg/L BAP and 5.0 µM $CuSO_4$; DBC3, 1.0 mg/L 2,4-D, 0.5 mg/L BAP and 5.0 µM $CuSO_4$. Callus quality was assessed microscopically and scored on a scale with ++++ designating highest quality and +designating lowest quality. Values were measured three weeks after initial callus induction and represent means of three replicates for each treatment. Golden Promise had a high frequency of callus induction regardless of the CIM composition (>87%, Table 7). Galena had a high-frequency of callus induction (>90%) on CIM without BAP. Tissue quality was poor on CIM containing BAP three weeks after induction but improved after two to three transfers on this medium. Only a fraction of scutellar tissues on Galena immature embryos formed callus, while most of the scutellar surface on Golden Promise immature embryos formed high-quality callus.

Galena had a similar or slightly higher initial callus growth rate compared to Golden Promise when grown on D medium (CIM containing 2,4-D alone) or DC medium (CIM containing 2,4-D and elevated levels of copper) (Table 7). Increasing the level of copper to 5.0 µM (50×) did not change the callus-induction frequency or the initial callus growth rate in either genotype, but callus quality improved, especially in Golden Promise. Compared to Galena, Golden Promise immature embryos produced callus with a larger number of distinct embryogenic structures.

The addition of BAP to the CIM reduced the callus-induction frequency and inhibited callus growth for both genotypes but produced higher quality callus that was shiny, compact, and contained highly regenerative structures with multiple shoot meristems (Table 7). Galena required a higher level of BAP (0.1 mg/L) than Golden Promise (0.01 mg/L BAP) to obtain callus of high quality (Table 7). The higher level of copper (50×) in combination with BAP resulted in more regenerative structures from callus having a slightly brownish color. When DBC3 medium, which contains a higher level of BAP (0.5 mg/L) and a lower level of 2,4-D (1.0 mg/L), was used for initial callus induction, a high rate of embryo germination and production of poor quality callus with a slow growth rate occurred (Table 7).

Production and Maintenance of Green Regenerative Tissues

Green embryogenic structures were observed 5–20 days after exposure of 3–4 week-old callus to dim light. A higher percentage of green sectors was produced by Golden Promise callus than Galena callus tissue. Once a callus having the appropriate morphology under dim light conditions was identified (green, shiny, nodular, compact), the sectors could be easily separated from the remaining callus and maintained on either DBC2 or DBC3 medium. Approximately 6–8 weeks post-initiation on DBC2 medium, Golden Promise tissue contained a few green shoots with multiple shoot meristem-like structures, but most tissues were green, shiny, nodular and compact. For Galena, however, DBC3 medium was optimal for maintaining green regenerative tissues. On DBC3 medium, Golden Promise tissues were softer and produced multiple shoot meristems; germination of some shoots was induced in response to a higher level of BAP. Galena tissues produced multiple shoot meristems and were more compact on DBC3 medium than Golden Promise tissues.

Thus, Galena requires a higher level of BAP (0.5 mg/L) than Golden Promise (0.1 mg/L) for callus induction and maintenance of high-quality green regenerative tissues. It should be noted that in these experiments, the callus-induction media used do not contain a high level of copper. Callus morphology was very good with 0.1 mg/L BAP, but the growth rate was very slow. When 50× copper was added, it seemed to speed up the growth rate. A higher level of BAP in callus-induction medium containing 50× copper was needed for optimal growth of tissues compared with callus-induction medium containing 1× copper.

Fertile Plant Regeneration from Green Regenerative Tissues

Seven pieces of green embryogenic tissues 4 to 6 mm in size from each genotype were transferred to RM (FHG medium), and after 25 days the number of regenerated shoots were counted. Each piece yielded multiple green shoots. After 2–3 weeks on RM, green structures (4–6 mm in size) from both genotypes produced approximately 9–17 green shoots per piece on either RM (Table 8) or hormone-free rooting medium. When germinating tissues were broken into pieces after 34 weeks in culture on RM and transferred to fresh medium, an even larger number of shoots were produced from the small green structures. All four-month-old green structures tested for regeneration produced multiple green shoots; no albino plants were observed (Table 8). Regenerated shoots were transferred to rooting medium in Magenta® boxes and rooted plants were transferred to soil and grown to maturity in the greenhouse.

Transformation of Galena

The in vitro culture system described above results in multiple green shoots from immature embryo-derived callus, thus providing the basis for successful transformation of the recalcitrant commercial genotype, Galena.

For transformation, the scutella of immature embryos of Galena were bombarded with subsequent culturing of the embryos on DC medium in the absence of selection. From the second transfer on, calli were maintained on selection medium; in the middle of the third round of transfer, calli were moved to dim light. Media containing higher levels of BAP, lower levels of 2,4-D, and 50× copper (DBC3 medium) were used for selection and maintenance from the fifth transfer on. In general, bialaphos-resistant calli with green sectors were observed at the fourth to fifth transfer. Calli with green sectors were maintained and proliferated until the green sectors formed fully developed regenerative structures. In most cases, when green sectors developed in fast-growing callus, fully developed green regenerative structures could be obtained.

For Galena, embryo size was very important for callus induction. Embryos smaller than about 1.2 mm resulted in very poor callus induction (less than 20 percent). Immature embryos about 1.5 mm to 2.0 mm in size had the highest callus induction frequency (>90 percent).

This method of generating green structures that yield multiple green shoots was used to improve the regenerability of transgenic calli selected on CIM containing either dicamba or 2,4-D. Green sectors were regenerated under selection and the plantlets were transferred to soil approximately three weeks after transfer to rooting medium. Using this transformation protocol, we obtained six independent Galena lines transformed with pAHC25. Three lines produced green sectors, were regenerable, and produced multiple green shoots. $T_0$ and $T_1$ plants contained DNA sequences that hybridized to bar and uidA and functionally expressed the uidA (GUS) reporter gene and the herbicide resistance gene bar as judged by resistance to Basta™.

Discussion

We have developed a very efficient, reproducible system for producing highly regenerative callus that gives rise to multiple green shoots over long periods of time (Table 8), eliminating the problem of albinism. This system can be successfully used to transform and regenerate previously recalcitrant genotypes.

First, we have optimized phytohormone treatment during callus initiation and proliferation. Immature embryos from Galena required higher levels of BAP than Golden Promise in order to produce high quality, green, regenerative tissue, perhaps due to differences between the two genotypes in endogenous levels of phytohormones. The addition of BAP to CIM containing 2,4-D decreased the growth rate of the immature embryo-derived callus from both genotypes but improved its quality and regenerability (Table 7). It is possible that the lack of albinism in this study was at least partially attributable to the use of BAP.

Recently, in vitro culture systems utilizing 2,4-D and BAP were developed for the differentiation of multiple shoots from excised shoot apical meristems from maize (Zhong et al., 1992) and oat (Zhang et al., 1996). We found that the sectors of regenerative barley calli of Golden Promise and Galena that were grown on CIM containing 2,4-D or dicamba produced multiple shoot meristem-like structures when subsequently transferred to an intermediate-incubation medium containing 2,4-D and BAP under dim light conditions. The use of 2,4-D in combination with BAP provided more prolonged regenerability and was more applicable to other genotypes than dicamba in combination with BAP.

Other changes in culture conditions significantly improved in vitro manipulation. Compared to D medium, DC medium, which includes increased levels of copper (5.0 μM, a 50-fold increase from MS medium), improved callus quality (Table 7) without changing callus-induction frequencies or the initial callus growth rate. This provided higher quality material from the initial step of selection that led to increased regenerability in transformed tissues. In addition, the use of DBC2 medium at the second transfer of Galena resulted in higher quality tissue that produced multiple shoot meristem-like structures.

These results were consistent with studies indicating that 50 μM copper (500×) is optimal for regenerability of the barley variety Hector, while 5.0 μM is optimal for regener ability for the barley variety Excel (Dahleen, 1996). Similar results were reported for wheat, wherein regeneration was reportedly higher on medium containing 10 μM CuSO$_4$ (100×) than on MS (0.1 μM Cu$^{2+}$) (Purnhauser, 1991). In yet another study, an increased copper level resulted in more somatic embryoids from anthers of tetraploid wheat (Ghaemi et al., 1994).

The exposure of tissue to light early in the selection process also likely reduced the incidence of albinism, perhaps by inducing chlorophyll biosynthetic enzymes (Holtorf et al., 1995). The presence of green, regenerative sectors assures that green plants will be generated, thus decreasing or eliminating the regeneration of albino plants as observed in Wan and Lemaux (1994).

Shiny, compact, slightly brown-colored calli with highly regenerative structures were obtained 2–3 weeks after incubating embryos in the dark on CIM. For both genotypes, the calli were transferred to fresh medium containing BAP, 2,4-D and copper, and green embryogenic structures were formed 5–14 days after exposure to dim light. All four-month-old regenerative structures of both Golden Promise and Galena regenerated multiple green shoots (approximately 11–17 green shoots per callus piece, Table 8) and no albino plants. By contrast, four-month-old callus of Golden Promise and Galena maintained on CIM containing either mg/L 2,4-D or dicamba alone did not produce green shoots (Example 1); even two-month-old callus of Golden Promise maintained on CIM containing 2,4-D or dicamba alone produced only 0.35 and 1.15 green shoots per callus piece, respectively (Example 2). These regenerative structures could be maintained on 2,4-D, BAP and copper for more than ten months in this state and could be regenerated to give multiple fertile green plants with both genotypes. The morphology of the green tissues generated by our protocol was similar to that of the multiple green meristematic domes differentiated from shoot apical meristems following culture on 2,4-D and BAP, but was more compact, possibly due to the inherent differences in the tissue source or to the use of higher concentrations of 2,4-D.

It has been reported that callus quality and callus-induction frequency depends on the selection of appropriately sized embryos and optimization of the physiological state of the donor plant (Dale and Dambrogio, 1979; Goldenstein and Kronstadt, 1986; Lürz and Lörz, 1987; Wan and Lemaux, 1994). However, the green regenerative tissues produced using our protocol can be obtained from a wider range of embryo sizes and from plants grown in either the growth chamber or the greenhouse; once green tissues are generated from any source, they can be proliferated as described. Small embryo size (<1.0 mm) was better in callus induction for Golden Promise, Morex, and Salome, but Galena required a larger size (1.5 to 2.0 mm) of embryos for a higher callus-induction frequency.

Many barley genotypes have a very low callus-induction frequency (Lürz and Lörz, 1987; Dahleen, 1996) and the appearance of albino plants and low regenerability occurs within 2.5 months after callus induction (Bregitzer et al., 1995). These traits limit the applicability of barley-transformation procedures for many modern commercial genotypes.

Previous efforts to transform the commercial varieties Moravian III and Galena produced large numbers of independently transformed lines, but yielded only albino plants upon regeneration. Changing the level of selection (to 1 mg/L bialaphos) or shortening the time of selection (from >5 rounds to 3 rounds) led to the regeneration of green plants that were found to be nontransformed.

The methods disclosed herein obviate the problems of albinism encountered with prolonged culture periods; in this study Galena and Golden Promise could be regenerated to give fertile green plants for more than 10 months. In addition, the use of either DBC2 or DBC3 in an intermediate step in regeneration greatly improves the frequency of shoot regeneration of transgenic and nontransgenic callus from Golden Promise initiated on 2,4-D or dicamba (Example 2).

Changes in particle bombardment, selection and culturing conditions, among others, also contributed to our transformation success with the previously recalcitrant genotype, Galena. Bombardments were previously carried out at 1100 psi, resulting in a reduction in callus-induction frequency in Galena, although Golden Promise was unaffected in its frequency. It is possible that lowering the rupture pressure and hence the speed of the microprojectiles lessened damage to the target tissue. In addition, selection of Galena was initiated two weeks post-bombardment rather than one day post-bombardment (Wan and Lemaux, 1994) in order to promote better callus induction and to allow for vigorous cell divisions of transformed cells without the adverse effects of the dead or dying cells in close proximity resulting from selection. Also, callusing embryos were broken into large pieces (4–5 mm) to avoid potential negative effects of wounding on transformed cells.

The approaches detailed herein can be used successfully to transform other recalcitrant commercial genotypes, such as the North American barley cultivars, Harrington, a two-row variety, and Morex, a six-row variety. Using these methods, Harrington and Morex produce green regenerative structures that yield multiple shoot meristems.

In addition, the ability to maintain green regenerative structures for long periods of time in culture permits the use of these structures as target tissues for transformation of cultivars prone to albinism, thus eliminating the need for maintaining donor plants and decreasing problems with albinism and poor regenerability, as well as reducing the induced mutation frequency and the resultant somaclonal variation.

TABLE 7

Callus-Induction Frequency, Initial Callus Growth Rate and Callus Morphology of Golden Promise (GP) and Galena on Different Callus-Induction Media

| Genotype | Callus-Induction Medium | Initial Callus-Induction Frequency (%) | Growth Rate (mg/day/embryo) | Callus Morphology |
| --- | --- | --- | --- | --- |
| GP | D | 100 | 12.8 | ++ |
|  | DC | 100 | 10.6 | ++++ |
|  | DB | 97 | 7.0 | +++(+) |
|  | DBC1 | 100 | 11.5 | +++++ |
|  | DBC2 | 100 | 9.1 | +++(+) |
|  | DBC3 | 87 | 6.5 | ++ |
| Galena | D | 97 | 15.0 | + |
|  | DC | 90 | 13.6 | +(+) |
|  | DB | 67 | 5.7 | ++(+) |
|  | DBC1 | 80 | 8.3 | ++ |
|  | DBC2 | 47 | 5.8 | +++ |
|  | DBC3 | 47 | 3.1 | ++ |

TABLE 8

Number of Shoots Regenerated from Green Embryogenic Tissues of Golden Promise and Galena

| Genotypes | Medium for Maintenance | # Regenerated Shoots/ Green Tissue[c] | |
|---|---|---|---|
| | | Green | Albino |
| Golden Promise | DBC2[a] | 17.0 | 0 |
| Galena | DBC2 | 13.0 | 0 |
| Galena | DBC3[b] | 14.4 | 0 |

[a]DBC2 = CIM containing 2.5 mg/L 2,4-D, 0.1 mg/L BAP and 5.0 μM CuSO$_4$
[b]DBC3 = CIM containing 1.0 mg/L 2,4-D, 0.5 mg/L BAP and 5.0 μM CuSO$_4$
[c]Values represent mean of three replicates for each treatment.

Example 4

Use of Green Regenerative Tissues of Barley as Transformation Targets

Materials and Methods

Plasmids

Plasmids pAHC20 and pAHC25 are described above. pAHC15 contains the GUS reporter gene expression cassette of pAHC25 (Christensen and Quail, 1996).

pUbiINPTII-1 was constructed by inserting the neomycin phosphotransferase (NPTII) coding sequence from pCaM-VNEO (Fromm et al., 1986) into the BamHI site of pAHC17 which contains the maize ubiquitin Ubi1 promoter, Ubi1 intron 1, and the nos 3' terminator (Christensen and Quail, 1996).

Preparation of Green Regenerative Tissues for DNA Particle Bombardment

Immature zygotic embryos were surface-sterilized, placed scutellum-side down on DBC2 medium, and incubated at 24±1° C. Regenerative tissues were maintained for 3-4 weeks, then cut into small pieces (about 3 to 5 mm), transferred to fresh DBC2 medium, and grown under dim light conditions. After an additional three weeks, green callusing sectors were broken into pieces (about 3 to 5 mm) and transferred to fresh DBC2 medium. Green regenerative tissues were maintained on DBC2 medium with subculturing at 3- to 4-week intervals. CIM containing 2.5 mg/L 2,4-D, 0.1 mg/L BAP and 5.0 μM CuSO$_4$ (i.e., DBC2 medium) was used for the induction of green regenerative tissues from the other genotypes.

For bombardment, green tissues (about 3 to 5 mm, four-months old) of Golden Promise and Galena were placed in the dark at 24±1° C. for one day, then transferred to DBC2 medium containing 0.2 M mannitol and 0.2 M sorbitol. Four hours after treatment with the osmoticum, green tissues were bombarded as described (Lemaux et al., 1996) with gold particles (Analytical Scientific Instruments, Alameda, Calif.) coated with pAHC25, a mixture of pAHC20 and pAHC15, or a mixture of pUbiINPTII-1 and pAHC15 at 900 or 1100 psi. At 16–18 hours after bombardment, the green tissues were transferred to DBC2 medium without osmoticum and grown at 24±1° C. under dim light conditions (about 10 μE, 16 h-light).

Selection and Regeneration of Transformed Tissue

Following an initial 3- to 4-week culturing period on nonselective medium, each piece of green tissue was broken into 1 to 2 pieces (about 4 mm to 5 mm, depending on size of original tissue piece) and transferred to DBC2 medium (Golden Promise or Galena) or DBC3 (Galena) medium supplemented with 4 to 6 mg/L bialaphos for bar selection or 40 to 50 mg/L geneticin (G418) for nptII selection. Green tissues were selected on DBC2 or DBC3 medium and 4 mm to 5 mm tissues subcultured at 3- to 4-week intervals. Putative green tissue transformants, identified by their fast-growth character on the selective medium, were transferred to Magenta® boxes containing rooting medium that was supplemented either with 4 mg/L bialaphos for bar selection or without selective agent for regeneration of nptII transformants. When shoots reached the top of the box, plantlets were transferred to 6-inch pots containing Supersoil (R. McClellan, S. San Francisco, Calif.), gradually acclimatized, and grown to maturity in the greenhouse.

Results and Discussion

Various targets have been used for barley transformation, including immature zygotic embryos (Wan and Lemaux, 1994; Hagio et al., 1995), young callus (Wan and Lemaux, 1994), microspore-derived embryos (Wan and Lemaux, 1994), microspores (Jähne et al., 1994) and protoplasts (Funatsuki et al., 1995; Salmenkallio-Marttila et al., 1995). Immature zygotic embryos are currently the most widely used and reliable target tissue for barley transformation. However, immature embryos from most commercially important barley genotypes have low callus-induction response rates (Lürz and Lörz, 1987; Dahleen, 1996). Moreover, in vitro-derived tissue culture material is limited in its ability to yield green plants for prolonged periods (Bregitzer et al., 1995). Prolonged culturing periods and/or selection stress required during the transformation process result in a large proportion of albino (chlorophyll-deficient) plants (Foroughi-Wehr et al., 1982; *Wan and Lemaux,* 1994; Bregitzer et al., 1995). In addition, the use of immature embryos and microspores as target tissues requires the year-round maintenance of donor plants grown under defined growth conditions.

We have established a reproducible barley transformation system based on microprojectile bombardment of green tissues that utilizes an in vitro culture system for the production of multiple green shoots from callus derived from immature scutellar tissue. Selection commenced 3 to 4 weeks after bombardment to allow transformed cells to proliferate in the absence of dead or dying cells resulting from selection or wounding. From the second transfer, selection was started using DBC2 medium or DBC3 medium that was supplemented either with bialaphos for bar selection or G418 (geneticin) for nptII selection. Putative transformants identified after 3 to 4 rounds of selection were transferred to rooting medium supplemented with bialaphos.

Using this transformation protocol we have obtained one confirmed Golden Promise line transformed with pAHC20 plus pAHC15 following selection with bialaphos, plus one putative transformed Galena line with pUbiINPTII-1 plus pAHC15 after G418 selection. Both lines were regenerable, producing green shoots and plants. Transformation was confirmed by PCR analysis.

This protocol greatly reduces problems with albinism and poor regeneration observed previously (Wan and Lemaux, 1994; Foroughi-Wehr et al., 1982; Bregitzer et al., 1995; Koprek et al., 1996; etc.) and can also be applied to other recalcitrant barley cultivars such as Harrington and Morex.

Example 5

Callus Morphology of Wheat on Different Callus Induction Media

The tissue culture protocols described above for use with barley are also useful for a variety of other plant species, including various monocot species.

For example, we have shown that the wheat variety Bobwhite also shows improved initial callus induction and callus morphology when tested on CIM containing high levels of copper and BAP. In experiments conducted as in Example 1 above (except as noted), immature whole embryos (1–2 mm) of Bobwhite were tested on six different CIMs, each including MS medium supplemented with 30 g/L maltose, 0.5 mg/L thiamine-HCl, 150 mg/L asparagine, and solidified with 2.5 g/L Phytagel [pH 5.85]), and supplemented with copper and phytohormones as follows:

(1) WD: 2.0 mg/L 2,4-D and 0.1 μM $CuSO_4$.
(2) WDC: 2.0 mg/L 2,4-D and 5.0 μM $CuSO_4$.
(3) WDB: 2.0 mg/L 2,4-D, 0.1 mg/L BAP, and 0.1 μM $CuSO_4$.
(4) WDBC1: 2.0 mg/L 2,4-D, 0.01 mg/L BAP, and 5.0 μM $CuSO_4$.
(5) WDBC2: 2.0 mg/L 2,4-D, 0.1 mg/L BAP, and 5.0 μM $CuSO_4$.
(6) WDBC3: 2.0 mg/L 2,4-D, 0.5 mg/L BAP, and 5.0 μM $CuSO_4$.

The shoot apex was removed seven days after callus induction. The morphology of the callus induced on the media is shown in Table 9.

TABLE 9

Callus Morphology of Bobwhite Wheat on Different Callus-Induction Media

| Callus-Induction Medium | Callus Morphology[a] |
|---|---|
| WD | ++ |
| WDC | ++(+) |
| WDB | +++ |
| WDBC1 | +++ |
| WDBC2 | ++++ |
| WDBC3 | +++++ |

[a]Morphology ranges from + (watery, least compact, no regenerative meristem-like structures, white) to +++++ (least watery, most compact, multiple meristem-like structures).

Example 6

Expression of Green Fluorescent Protein and its Inheritance in Transgenic Barley (*Hordeum vulgare* l.) Plants In this example, successful transformation of barley using sgfp(S65T) gene linked to either rice action promoter or barley endosperm-specific D-hordein promoter is demonstrated. Its expression and inheritance in transgenic barley plants is described.

Materials and methods

Plant Materials

A two-rowed spring cultivar of barley, Golden Promise, was grown in growth chambers as described previously (Wan and Lemaux 1994; Lemaux et al., 1996).

Plasmids

Plasmids, pAHC20, pAct1IsGFP-1 and pDhsGFP-1, were used for transformation. pAHC20 (Christensen and Quail, 1996) contains bar under control of the maize ubiquitin Ubi1 promoter and intron (Ubi1/Ubi1I) and nos. pAct1IsGFP-1 (FIG. 1A) contains the synthetic green fluorescent [sgfp (S65T)] gene driven by the rice actin1 promoter (Act1) and its intron (Act1I) and terminated by nos. pDhsGFP-1 (FIG. 1B) contains sgfp(S65T) controlled by the barley endosperm-specific D-hordein promoter and terminated by nos.

Stable Barley Transformations

Stable transgenic lines of barley expressing the rice actin promoter-sgfp(S65T) and D-hordein-sgfp(S65T) genes were obtained using modifications of a published protocol (Wan and Lemaux 1994; Lemaux et al., 1996). Gold particles (1.0 μm) were coated with 25 μg of an equimolar ratio of a mixture of pAHC20 (Christensen and Quail 1996) and either pAct1IsGFP-1 or pDhsGFP-1, and used in bombardment experiments. Bombarded, osmotically treated immature embryos (IEs) were selected on DC medium (Cho et al., 1998) with 5 mg/L bialaphos. Transgenic calli were transferred for an intermediate culturing step, between the callus-induction (DC medium) and regeneration (FHG, Hunter 1988; *Wan Lemaux* 1994) steps, onto DBC2 medium (Cho et al., 1998) comprising 2.5 mg/L 2,4-D, 0.1 mg/L BAP, 5.0 μM $CuSO_4$ and 5 mg/L bialaphos. This intermediate culturing step was carried out under dim light conditions (approximately 10 to 30 μE, 16 h-light) for 1 to 2 months. Regenerated shoots were transferred to Magenta boxes containing rooting medium (callus-induction medium without phytohormones) comprising 3 mg/L bialaphos. When shoots reached the top of the box, plantlets were transferred to soil and grown to maturity in the greenhouse.

Cytological Analysis

Cytological analysis of transgenic barley plants was performed as previously described (Cho et al., 1999; Choi et al., 1999) using healthy root tips collected from young plants grown in the greenhouse.

GFP Expression Detection by Fluorescence Microscopy

GFP expression was monitored at higher magnification using a Nikon Microphot-5A fluorescent microscope equipped with a Nikon B-2A filter block containing a 450–490 excitation filter and a BA520 emission barrier filter.

Herbicide Application

To determine herbicide sensitivity of $T_0$ plants and their progeny, a section of leaf blade at the 4- to 5-leaf stage was painted using a cotton swab with a 0.25% solution (v/v) of Basta™ solution plus 0.1% Tween 20. Plants were scored 1 week after herbicide application.

Figure 1B:
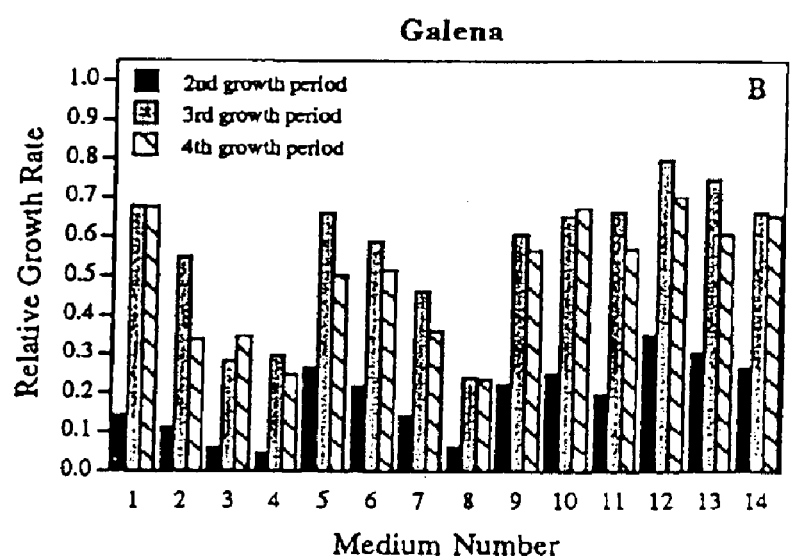
FIG. 1B shows the relative growth rate (g/g fresh weight/day) of callus of the barley genotype Galen (B) grown on fourteen different media. (The auxin and cytokinin concentrations of the media are given in Table 1.)

Genomic DNA Isolation, Polymerase Chain Reaction (PCR) and DNA Blot Hybridization To test for the presence of sgfp(S65T) in genomic DNA of putatively transformed lines, 500 ng of genomic DNA was amplified by PCR using either of two primer sets, Act1int1 (5'-TCGTCAGGCTTAGATGTG-3') (SEQ ID NO: 1) plus sGFP4R (5'-agaggtaccTTACTTGTACAGCTCGTC-3') (SEQ ID NO: 2) for pAct1IsGFP-1 transformants and sGFP3 (5'-ccctctagaCCATGGTGAGCAA GGGCGAG-3') (SEQ ID NO: 3) plus sGFP4R for pDhsGFP-1 transformants. The presence of bar was tested using the primer set, BAR5 F (5'-CATCGAGACAAGCACGGTCAACTTC-3') (SEQ ID NO: 4) plus BAR1R (5'-ATATCCGAGCGCCTCGTGCATGCG-3') (SEQ ID NO: 5) (Lemaux et al., 1996). Amplifications were performed in a 25-μl reaction with Taq DNA polymerase according to a protocol described by Cho et al., (1998). For DNA hybridization analysis, 10 μg of total genomic DNA from leaf tissue of each line was digested with SacI, separated on a 1.0% agarose gel, transferred to Zeta-Probe GT membrane and hybridized with a radiolabeled sgfp(S65T)-specific probe following the manufacturer's instructions. Digestion with SacI yielded a 1.54-kb fragment containing 0.47-kb actin1 intron, 0.72-kb sgfp(S65T) and 0.35-kb nos from pAct1IsGFP-1 (FIG. 1A). The sgfp(S65T)-containing 0.72-kb NcoI-NotI fragment from pAct1IsGFP-1 was purified using a QIAEX gel extraction kit and labeled with $\alpha$-$^{32}$P-dCTP using random primers.

Results

GFP Expression in Transgenic Barley Tissues

The sgfp(S65T) gene, driven by either rice actin promoter [pAct1IsGFP-1] or barley endosperm-specific D-hordein promoter [pDhsGFP-1], was introduced into barley IEs by microprojectile bombardment. Transient expression driven by the rice actin promoter resulted in large numbers of GFP-expressing foci in IEs while that driven by the D-hordein promoter led to very small, weak or undetectable GFP expression in IEs.

Different tissues from stably transformed callus, $T_0$ plants and their progeny were tested for GFP activity. GFP driven by the rice actin promoter was strongly expressed in callus, pollen, ovary, stigma, root, immature embryo and endosperm tissues. GFP expression in leaf tissues was obscured by chlorophyll fluorescence. Strong GFP expression was seen in endosperm tissues derived from transgenic lines having D-hordein-sgfp(S65T) construct; GFP expression was not visibly detected in other parts of the plant.

Cytological Analysis of Transgenic Plants

Chromosome numbers were counted in root meristems of 26 independently transformed $T_0$ barley plants. Out of 26 transgenic lines examined, 11 lines (GPActIGFP-1, -6, -10, -16, -23, -41, -44, GPDhsGFP-10, -11, -12, and -14) had the normal diploid chromosome complement (2n=2x=14), while the remaining 15 lines (GPActIGFP-4, -7, -8, -9, -22, -37, -39, 40, -42, -43, GPDhGFP-1, -2, -3, -4, and -5) were tetraploid (2n=4x=28) (Table 1).

PCR and DNA Blot Hybridization Analysis of Transgenic Plants

In order to determine the presence of introduced gene(s) in putatively transformed $T_0$ plant leaves, PCR analysis was performed. Table 10 shows the results of PCR amplification from genomic DNA using 3 different sets of primers for the sgfp(S65T) and bar genes. All 26 transgenic lines, which were identified as PAT (phosphinothricin acetyltransferase)-expressing transformants after bialaphos selection, showed the 0.34-kb internal bar fragments after PCR amplification. Fifteen of 17 lines produced a 0.86-kb PCR-amplified fragment, representing sgfp(S65T) plus part of the actin1 intron of pAct1IsGFP-1, using the primer set, Act1int1 and sGFP4R. Of the 15 PCR-positive lines, one line (GPActIGFP-8) was negative for GFP expression. Seven out of 9 lines produced a 0.72-kb PCR-amplified fragment for the pDhsGFP-1 plasmid using the primer set, sGFP3 and sGFP4R.

A DNA blot hybridization of genomic DNA from transgenic barley lines transformed with pAct1IsGFP-1 was conducted (data not shown). Genomic DNA from 7 of 8 transformed lines produced the expected 1.54-kb actin intron-sgfp(S65T)-nos fusion fragment after digestion with SacI. The remaining transgenic line (GPActIGFP-8) had fragments larger than the expected size. Copy numbers of the sgfp(S65T) gene ranged from 2 to 7 copies per genome.

Analysis of $T_0$ Plants and their Progeny for PAT Expression

Enzyme activity of PAT in $T_0$ plants was tested by painting leaves with Basta. Leaf tissue from $T_0$ plants of all 26 independent lines exhibited PAT expression driven by the maize ubiquitin promoter as evidenced by Basta resistance of challenged tissue (Tables 10 and 11). However, only 17 out of 26 lines exhibited Basta-resistance in $T_1$ progeny; of the remaining 9 lines five lost PAT expression and another four lines were sterile. Eleven out of 17 Basta-positive lines had a 3:1 segregation pattern for expression of PAT in $T_1$ progeny (GPActIGFP-8, -10, -22, -39, -40, -44, GPDhGFP-1, -2, -3, -4, and -14). The remaining 5 lines (GPActIGFP-4, -9, -23, -37, 42) had a higher than 3:1 segregation pattern and one line (GPDhsGFP-10) had a lower than 3:1 segregation ratio.

TABLE 10

Expression and inheritance of sgfp(S65T) and bar in transgenic barley plants

| Plasmid used for bombardment | Transgenic lines | Ploidy | GFP expression in callus | PCR gfp | PCR bar | $T_0$ GFP | $T_0$ Basta painting | $T_1$ Basta painting (+/−) | $T_1$ GFP (+/−) | $T_2$ GFP (+/−) | $T_1$ seed set (%) |
|---|---|---|---|---|---|---|---|---|---|---|---|
| pAct1IsGFP-1 + pAHC20 | GPActIGFP-1 | diploid | + | + | + | + | + | 0/9 | 0/8 | | 4.5 |
| | GPActIGFP-1-7 | | | | | | | | | 0/17 | |
| | GPActIGFP-1-8 | | | | | | | | | 0/33 | |
| | GPActIGFP-4 | tetraploid | + | + | + | + | + | 42/1 | 20/0 | | 57.8 |
| | GPActIGFP-4-1 | | | | | | | | | 68/0 | |
| | GPActIGFP-4-2 | | | | | | | | | 63/0 | |
| | GPActIGFP-4-3 | | | | | | | | | 52/3 | |
| | GPActIGFP-4-7 | | | | | | | | | 32/0 | |
| | GPActIGFP-4-8 | | | | | | | | | 3/0 | |
| | GPActIGFP-4-9 | | | | | | | | | 40/2 | |
| | GPActIGFP-6 | diploid | + | + | + | − | + | 0/17 | 0/16 | | 15.2 |
| | GPActIGFP-6-1 | | | | | | | | | 0/24 | |
| | GPActIGFP-7* | tetraploid | + | + | + | + | + | | | | 0 |
| | GPActIGFP-8 | tetraploid | − | + | + | − | + | 0/18 | 9/1† | | 50.0 |
| | GPActIGFP-9 | tetraploid | + | + | + | + | + | 22/1 | 22/0 | | 24.5 |
| | GPActIGFP-9-1 | | | | | | | | | 22/16 | |
| | GPActIGFP-9-2 | | | | | | | | | 16/2 | |
| | GPActIGFP-9-3 | | | | | | | | | 0/62 | |
| | GPActIGFP-9-4 | | | | | | | | | 21/0 | |
| | GPActIGFP-9-5 | | | | | | | | | 11/0 | |
| | GPActIGFP-10 | diploid | − | − | + | − | + | 0/19 | 18/4† | | 72.7 |
| | GPActIGFP-10-1 | | | | | | | | | 0/13 | |
| | GPActIGFP-16 | diploid | + | + | + | − | + | 0/26 | 0/15 | | 39.4 |
| | GPActIGFP-16-1 | | | | | | | | | 0/21 | |

TABLE 10-continued

Expression and inheritance of sgfp(S65T) and bar in transgenic barley plants

| Plasmid used for bombardment | Transgenic lines | Ploidy | GFP expression in callus | PCR gfp | PCR bar | GFP | Basta painting | T₀ GFP (+/−) | T₁ Basta painting (+/−) | T₂ GFP (+/−) | T₁ seed set (%) |
|---|---|---|---|---|---|---|---|---|---|---|---|
| | GPActIGFP-22 | tetraploid | − | − | + | − | + | 0/12 | 15/1† | | 47.9 |
| | GPActIGFP-22-1 | | | | | | | | | 0/15 | |
| | GPActIGFP-23 | diploid | + | + | + | − | + | 0/44 | 22/0 | | 33.3 |
| | GPActIGFP-23-1 | | | | | | | | | 0/13 | |
| | GPActIGFP-37 | tetraploid | + | + | + | + | + | 39/5 | 24/2 | | 47.8 |
| | GPActIGFP-37-1 | | | | | | | | | 43/2 | |
| | GPActIGFP-37-2 | | | | | | | | | 51/4 | |
| | GPActIGFP-37-3 | | | | | | | | | 59/0 | |
| | GPActIGFP-37-4 | | | | | | | | | 21/2 | |
| | GPActIGFP-37-6 | | | | | | | | | 50/2 | |
| | GPActIGFP-37-7 | | | | | | | | | 0/45 | |
| | GPActIGFP-37-9 | | | | | | | | | 24/5 | |
| | GPActIGFP-39 | tetraploid | + | + | + | + | + | 35/2 | 3/0† | | 12.5 |
| | GPActIGFP-39-1 | | | | | | | | | 16/2 | |
| | GPActIGFP-39-2 | | | | | | | | | 46/16 | |
| | GPActIGFP-40 | tetraploid | + | + | + | + | + | 38/3 | 24/6† | | 47.5 |
| | GPActIGFP-40-1 | | | | | | | | | 20/10 | |
| | GPActIGFP-40-4 | | | | | | | | | 4/0 | |
| | GPActIGFP-40-8 | | | | | | | | | 6/2 | |
| | GPActIGFP-40-9 | | | | | | | | | 48/1 | |
| | GPActIGFP-40-14 | | | | | | | | | 0/25 | |
| | GPActIGFP-40-15 | | | | | | | | | 24/7 | |
| | GPActIGFP-41* | diploid | + | + | + | + | + | | | | 0 |
| | GPActIGFP-42 | tetraploid | + | + | + | + | + | 25/1 | 16/0 | | 46.7 |
| | GPActIGFP-42-1 | | | | | | | | | 57/5 | |
| | GPActIGFP-42-2 | | | | | | | | | 33/0 | |
| | GPActIGFP-42-3 | | | | | | | | | 65/0 | |
| | GPActIGFP-42-4 | | | | | | | | | 22/4 | |
| | GPActIGFP-42-6 | | | | | | | | | 50/0 | |
| | GPActIGFP-43* | tetraploid | + | + | + | + | + | | | | 0 |
| | GPActIGFP-44 | diploid | + | + | + | − | + | 0/22 | 19/6† | | 21.9 |
| | GPActIGFP-44-1 | | | | | | | | | 0/35 | |
| pDhsGFP-1 + pAHC20 | GPDhGFP-1* | tetraploid | − | + | + | − | + | 17/3† | 6/1† | | 18.9 |
| | GPDhGFP-1-1 | | | | | | | | | 37/20 | |
| | GPDhGFP-1-3 | | | | | | | | | 0/13 | |
| | GPDhGFP-1-4 | | | | | | | | | 5/0 | |
| | GPDhGFP-2 | tetraploid | − | + | + | − | + | 34/1 | 11/3† | | 34.2 |
| | GPDhGFP-2-1 | | | | | | | | | 0/16 | |
| | GPDhGFP-2-2 | | | | | | | | | 43/4 | |
| | GPDhGFP-3 | tetraploid | − | + | + | − | + | 24/6† | 3/0† | | 38.9 |
| | GPDhGFP-3-1 | | | | | | | | | 4/0 | |
| | GPDhGFP-3-2 | | | | | | | | | 10/0 | |
| | GPDhGFP-3-3 | | | | | | | | | 16/2 | |
| | GPDhGFP-4 | tetraploid | − | | | | | 35/7† | 11/0† | | 15.0 |
| | GPDhGFP-4-1 | | | + | + | − | + | | | 0/20 | |
| | GPDhGFP-4-2 | | | | | | | | | 0/35 | |
| | GPDhGFP-4-3 | | | | | | | | | 27/0 | |
| | GPDhGFP-5* | tetraploid | − | + | + | − | + | | | | 0 |
| | GPDhGFP-10 | diploid | − | + | + | − | + | 35/30 | 13/19 | | 64.1 |
| | GPDhGFP-10-1 | | | | | | | | | 0/55 | |
| | GPDhGFP-10-2 | | | | | | | | | 13/9 | |
| | GPDhGFP-10-3 | | | | | | | | | 0/37 | |
| | GPDhGFP-10-4 | | | | | | | | | 27/33 | |
| | GPDhGFP-10-5 | | | | | | | | | 0/33 | |
| | GPDhGFP-11 | diploid | − | − | + | − | + | 0/33 | 0/8 | | 38.8 |
| | GPDhGFP-11-2 | | | | | | | | | 0/19 | |
| | GPDhGFP-11-3 | | | | | | | | | 0/34 | |
| | GPDhGFP-12 | diploid | − | + | + | − | + | 78/12 | 0/15 | | 70.2 |
| | GPDhGFP-12-1 | | | | | | | | | 36/20 | |
| | GPDhGFP-12-2 | | | | | | | | | 0/29 | |
| | GPDhGFP-12-3 | | | | | | | | | 51/8 | |
| | GPDhGFP-12-4 | | | | | | | | | 33/7 | |
| | GPDhGFP-12-5 | | | | | | | | | 10/0 | |

TABLE 10-continued

Expression and inheritance of sgfp(S65T) and bar in transgenic barley plants

| Plasmid used for bombardment | Transgenic lines | Ploidy | GFP expression in callus | T₀ PCR gfp | T₀ PCR bar | T₀ GFP | T₀ Basta painting (+/−) | T₁ Basta painting (+/−) | T₁ GFP (+/−) | T₂ GFP (+/−) | T₁ seed set (%) |
|---|---|---|---|---|---|---|---|---|---|---|---|
| | GPDhGFP-14 | diploid | − | + | + | − | + | 69/6 | 18/4† | | 63.9 |
| | GPDhGFP-14-1 | | | | | | | | | 50/0 | |
| | GPDhGFP-14-2 | | | | | | | | | 53/0 | |
| | GPDhGFP-14-3 | | | | | | | | | 39/15 | |
| | GPDhGFP-14-4 | | | | | | | | | 0/13 | |

*sterile.
†Analyses using the $\chi^2$-test indicate that the segregation ratios of T₁ progeny for GFP and PAT were not significantly different from 3:1 (at $\alpha = 0.05$).

TABLE 11

Summary of inheritance of transgene expression in transgenic barley plants

| Plasmids used for bombardment | No. of gfp-positive lines* | No. of GFP-expressing lines Callus | T₀ plant | T₁ seed | T₂ seed | No. of bar-positive lines* | No. of PAT-expressing lines Callus | T₀ plant | T₁ plant |
|---|---|---|---|---|---|---|---|---|---|
| pActIIsGFP-1 + pAHC20 | 15 | 14 | 10 | 6(3)† | 6(3) | 17 | 17 | 17 | 11(3) |
| pDhsGFP-1 + pAHC20 | 7 | 0 | 0 | 6(1) | 6(1) | 9 | 9 | 9 | 6(1) |

†Values are the numbers of GFP- or PAT-expressing lines and values in parentheses are the numbers of sterile transgenic lines that are not included in total numbers of transgenic lines.
*gfp- and bar-positive lines were identified by PCR and/or DNA blot hybridization analyses.

Analysis of T₀ Plants and their Progeny for GFP Expression

GFP activity in root and endosperm tissues was tested by fluorescence microscopy. GFP expression, driven by the rice actin promoter, was observed in 14 out of 17 independent bialaphos-resistant transgenic callus lines (Tables 10 and 11), giving a 82% coexpression efficiency. However, expression was gradually lost in T₀ and T₁ plants. Out of the 14 independent GFP-expressing callus lines tested, T₂ progeny from only 6 (GPActIGFP-4, -9, -37, -39, -40 and -42) were positive for GFP expression; four GFP-expressing lines (GPActIGFP-6, -16, -23, -44) lost GFP expression during plant regeneration from calli (Tables 10 and 11), one line (GPActIGFP-1) lost GFP expression in the transition from T₀ to T₁ generations and three lines (GPActIGFP-7, -41 and 43) were sterile. Seventy percent (7/10) of the GFP-expressing T₀ lines were fertile with a range of 5 to 58% seed set (Table 10). All six GFP-positive lines had a segregation pattern, close to 15:1 for expression of GFP in T₁ progeny. Homozygous plants from 4 independent lines (GPActIGFP-4, -9, -37 and -42) were obtained.

Expression of GFP driven by the endosperm-specific D-hordein promoter was more stable in its inheritance pattern in T₁ progeny than actin-driven GFP; all 7 sgfp (S65T)-positive independent lines tested expressed GFP and expression was stably transmitted to T₂ progeny of all 7 lines (GPDhGFP-1, -2, -3, 4, -10, -12 and -14) (Tables 1 and 2). To date, 3 homozygous lines were obtained (GPDhGFP-3, -4 and -14). Eighty-six percent (6/7) of the GFP-expressing T₀ lines were fertile with a range of 15 to 70% seed set (Table 1). Three (GPDhGFP-1, -3 and -4) out of 7 GFP-expressing lines had a 3:1 segregation pattern for GFP expression in T₁ progeny. Of the remaining 4 lines, 3 lines (GPDhGFP-2, -12 and -14) had higher than a 3:1 segregation for GFP expression and another line (GPDhGFP-10) had lower than a 3:1 segregation ratio.

Example 7

Development of Transformation Systems for Monocotyledonous Crop Species

In this example, the development of efficient transformation systems for monocot crop species to facilitate efficient and effective new cultivar development is described. The practical applications of the transformation systems and molecular principles and strategies for production of foreign proteins in barley and wheat seeds are described. Although the work has focused on cereals and grasses, many of the principles and strategies will have broad application for dicotyledonous crops.

Results and Discussion

Development of Novel Transformation Systems for Recalcitrant, Commercial Barley Cultivars The utility of genetic engineering approaches is dependent upon being able to generate large numbers of independently transformed, fertile, green plants that maintain the important characteristics of the starting germplasm. The first demonstrations of stable transformation of barley that resulted in fertile, stably transformed barley plants was in 1994 (Wan and Lemaux 1994). These studies utilized a two-rowed malting cultivar Golden Promise that was amenable to in vitro culture but is currently not commercially important; the DNA introduction method was microparticle bombardment. Primary explants that required little or no preculturing prior to bombardment were utilized, i.e. immature embryos (IEs) and 7- to 9-day-old callus. These explants were utilized in barley because of the rapid loss of regenerability and increased albinism that occurs in in vitro cultured tissue.

Using a standard embryogenic callus induction method, Wan and Lemaux (1994) developed a reproducible transformation method with Golden Promise that gave an "effective transformation frequency" (ETF=# fertile, regenerable independent lines/total # explants) of approximately 4%. The direct use of this method with commercially important cultivars, however, was problematic. Frequencies of callus induction were often low; target tissues negatively impacted by bombardment; and regenerability of in vitro-cultured tissue lost quickly during selection. The barley germplasm that forms the foundation for North American breeding programs, many in six-rowed backgrounds, is different from Golden Promise in virtually every aspect important to commercial production and utilization. Therefore, utilization of Golden Promise as a source of transgene-derived traits will require considerable extra effort. It would necessitate multiple cycles of backcrossing and selection to identify plants that are identical to the commercials variety with the exception of the new value-added trait since the selected allelic combinations that are critical to commercial success of these varieties would have to be preserved.

Application of the published transformation method (Wan and Lemaux 1994; Lemaux et al., 1996) to commercially important North American varieties, e.g. Galena, Harrington, Moravian III and Morex, resulted in the identification of independently transformed callus lines, which were either nonregenerable or yielded only albino plants (Wan, Y., Cho, M.-J. and Jiang, W., unpublished results). Changing the level of selection agent or shortening the time of selection led to the regeneration of green plants, but none were transformed (Wan, Y. and Lemaux, P. G., unpublished results).

One insight into a potential mitigator of genotype-dependence came from a report in which the effects of DNA bombardment parameters were examined relative to their effects on the callus-induction frequency of certain target tissues. Damage by microparticles to IEs of Galena, a two-rowed recalcitrant commercial cultivar, was found to be significantly more than to IEs of Golden Promise, as judged by scanning electron microscopic analysis (Koprek et al., 1999). Koprek et al., (1996) also showed that the callus response of five recalcitrant cultivars was severely reduced by bombardment at pressures around 1100 psi with the Bio-Rad machine; of Golden Promise was unaffected. These results suggest that IEs from different cultivars have differing capacities to withstand microparticle bombardment and this parameter must be optimized to achieve success.

Another hurdle to successful transformation of commercial varieties had to do with the numbers of totipotent cells found in the cultures. The percentage of totipotent cells in recalcitrant cultivars such as Galena, Harrington and Morex was even lower than that in an amenable cultivar, Golden Promise. In general, callus-maintenance media containing auxin and no cytokinin has been used for the long-term tissue culture periods needed during transformation. In barley this led to the generation of tissues with low regenerability (Jiang et al., 1998). The use of media, comprising an auxin, 2,4-D, and a low level of a cytokinin, BAP, and higher levels of copper for callus initiation, stimulated the formation and maintenance of highly regenerative, green tissues with long-term regenerability characteristics (Cho et al., 1998b). The use of this method of initiating and maintaining callus on the medium described above caused the small number of totipotent cells in the scutellum to proliferate, and, by transferring these tissues to a medium with higher ratios of cytokinin to auxin, it was possible to convert the tissue from an embryogenic state to a state more closely resembling a shoot meristem culture (Cho et al., 1998b; Lemaux et al., 1999). This tissue, termed green regenerative tissue, could give rise to multiple shoots over long periods. The judicious use of media with differing auxin to cytokinin ratios improved callus quality and significantly enhanced duration of regenerability of tissues of the barley varieties, Galena (Jiang et al., 1998), Harrington, and Morex (Cho, M.-J. and Jiang, W., unpublished results). Levels of cupric sulfate in the range of 5–1000 times the level in the MS-based culture media were also found to have positive effects on the long-term maintenance and regenerability of the barley cultures.

Morphologically, the green tissues generated by this protocol looked strikingly similar to those cultured from excised shoot apices of barley on media comprising 2,4-D- and BAP-. Molecular analysis using immunolocalization confirmed visual observations. The expression pattern of a gene associated with maintenance of the meristematic state in barley shoots (Zhang et al., 1998), a knotted1 (Vollbrecht et al., 1991) homologue, was studied in tissue derived from the excised shoot apex and from green tissue. The pattern was similar in these two tissues but different from that seen in callus initiated and maintained on auxin alone (2,4-D or dicamba) (Zhang, unpublished results).

The green regenerative tissues generated and maintained on one or two of these media, DBC2 (comprising 2.5 mg/L 2,4-D, 0.1 mg/L BAP and 5.0 µM $CuSO_4$, Cho et al., 1998) or DBC3 (comprising 1.0 mg/L 2,4-D, 0.5 mg/L BAP and 5.0 µM $CuSO_4$, Cho et al., 1998), were used directly as transformation targets. For bombardment, 3 to 4 mm pieces of green tissue of Golden Promise, Galena and Harrington, removed 3 to 4 months after initiation of the original culture, were osmotically treated on DBC2 or DBC3 medium and bombarded the same day with three different selection constructs, ubi-bar/ubi-uidA, ubi-nptII/ubi-uidA and act-hpt/ubi-uidA. The Bio-Rad PDS-1000 He was used at 900 or 1100 psi; rupture pressures for green regenerative tissues was less critical than for IEs since their compact, nodular structure resulted in less damage as evidenced by the ability of these tissues to continue proliferation following bombardment (Cho, M.-J., unpublished results). Sixteen to 18 hr post-bombardment, green tissues were transferred without osmoticum or selective agent to dim light on DBC2 or DBC3 medium for Golden Promise and Harrington or DBC3 for Galena. Selection with all agents started 34 weeks post-bombardment to allow for proliferation of transformed cells in the absence of the cell death resulting from wounding or selection. At that time, tissue was broken into pieces (3–5 mm) and transferred to either DBC2 or DBC3 medium (depending on morphology) with 3 mg/L bialaphos (bar), 20–25 mg/L hygromycin B (hpt) or 30 mg/L G418 (nptII), depending on the construct used. Starting with the third round of selection, levels of selective agent were increased to 45 mg/L bialaphos, 25 mg/L hygromycin B or 40 mg/L G418. Putative transformants, identified by their relatively fast growth on selective medium (FIG. 2D), were transferred to rooting medium (phytohormone-free callus-induction medium) with 2 to 3 mg/L bialaphos (bar) or without selective agent for hpt or nptII transformants.

Selection with hygromycin B or G418 resulted in a tighter selection for green tissues than did bialaphos, based on the relative frequency of escaped tissues. However, frequently albino plants were observed during regeneration of selected tissues, especially from hygromycin B and to a lesser extent those from G418 selection, whereas no albino plants were observed from tissues selected with bialaphos. This implies that hygromycin B and G418 selection might cause more stress on the in vitro-cultured cells. Using this transformation protocol, one Golden Promise (bar) and one Galena (nptII) lines were produced that yielded green plants that were confirmed by PCR and DNA blot hybridization analyses; three transformed Harrington lines from hygromycin B selection have also been confirmed (Table 12). Transformation frequencies (TF=# independent lines/total # explants) of dent transgenic rice lines were obtained from 133 pieces of tissue, giving a 6.8% TF (Table 12). The TF for forage/turf grasses varied amongst the crop species; 7.5%, orchardgrass (Cho et al., 2000); 6.8%, tall fescue (Cho et al., 1999b); 4.5%, red fescue (Cho et al., 1999b); 5.1%, creeping bentgrass; and 2.0%, Kentucky bluegrass (Table 12). Regenerability of the transgenic forage/turf grasses was 60 to 100% (Table 1).

TABLE 12

Summary of transformation experiments for monocrop species using highly regenerative tissues.

| Plant Species | Cultivar | % Transformation frequency (# transgenic events/# bombarded explants) | % Coexpression frequency (# lines with 2$^{nd}$ transgene activity/# total lines) | % Regenerability (# regenerable lines/# total lines) |
|---|---|---|---|---|
| Barley | Golden Promise | 0.9 (1/110) | 0 (0/1) | 100 (1/1) |
|  | Galena | 1.9 (1/53) | 100 (1/1) | 100 (1/1) |
|  | Harrington | 1.7 (3/176) | 67 (2/3) | 67 (2/3) |
| Oat | GAF/Park-1 | 25.7 (84/327) | 70 (59/84) | 100 (84/84) |
| Wheat | Bobwhite | 5.5 (10/183) | n.d.$^a$ | 100 (10/10) |
|  | Anza | 4.9 (4/82) | 50 (2/4) | 100 (4/4) |
|  | Yecora Rojo | 4.6 (3/65) | 67 (2/3) | 100 (3/3) |
|  | Karl | 3.8 (5/135) | n.d. | 100 (5/5) |
| Maize | H99 | 7.1 (5/70) | 60 (3/5) | 80 (4/5) |
|  | B73 | 2.6 (4/155) | n.d. | n.d. |
| Rice | Taipei 309 | 6.8 (9/133) | n.d. | n.d. |
| Orchardgrass | Rapido | 7.5 (11/147) | 45–60 (5/11–6/10)$^b$ | 91 (10/11) |
| Tall fescue | Ky 31 | 6.8 (8/118) | 50–75 (4/8–6/8)$^b$ | 100 (8/8) |
| Red fescue | 43F-93 | 4.5 (11/245) | 55–82 (6/11–9/11)$^b$ | 82 (9/11) |
| Creeping bentgrass | Putter | 5.1 (15/296) | n.d.$^{a, b}$ | 93 (14/15) |
| Kentucky bluegrass | Kenblue | 2.0 (10/507) | 30–40 (3/10–4/10)$^b$ | 60 (6/10) |

$^a$n.d.: not determined.
$^b$Three DNA constructs were bombarded for transformation.

Golden Promise, Galena and Harrington were 0.9 to 1.7%. Functional expression of GUS was assessed by histochemical analysis (Jefferson et al., 1987); strong uidA expression was detected in leaf tissues in transgenic Harrington plants, but not in the negative control.

Application of Novel Transformation Systems to Other Monocot Crops

We applied the in vitro culture system, initially developed for barley and described above, to other monocot crops such as oat, wheat, maize, rice, sorghum and forage/turf grasses. On media comprising auxin, cytokinin and high copper, highly regenerative, green tissues were induced and maintained from, depending on plant species and genotypes, immature embryos, zygotic embryos and/or embryogenic callus derived from mature seed.

Using highly regenerative tissues as transformation targets, we generated a large number of independently transformed lines for several monocot crop species that gave rise to transgenic plants (Table 12). For oat transformation, 84 independent transgenic events were obtained from 327 individual explants, giving a TF of 26% (Table 12) (Cho et al., 1999c); all events (100%) were regenerable. The use of these transformation systems also resulted in successful transformation of a spring wheat cultivar, Bobwhite, with 5.5% ETF (Table 12) (Kim et al., 1999). For the two previously recalcitrant spring wheat cultivars, Anza and Yecora Rojo, TFs were 4.9% and 4.6%; for a recalcitrant winter cultivar, Karl, the TF was 3.8% (Table 12). The TFs for maize cultivars, H99 and B73, a recalcitrant inbred line, were 7.1 and 2.6%, respectively (Table 12). Nine indepen- The transformation of recalcitrant varieties using green regenerative tissue has certain advantages over IEs. First, the use of this tissue does not require a constant source of IEs from plants grown under controlled growth conditions. Second, green regenerative tissues do not require special care during bombardment. Third, these tissues incur negligible losses of regenerability compared to the IE-derived callus during the 2 to 3 months needed for selection of transformed tissue. Fourth, albinism problems rarely occur except following certain stressful selection conditions. Fifth, it is possible that plants deriving from green tissues incur less somaclonal variation than those deriving from tissues cultured with auxin alone (Zhang et al., 1999).

Example 8

Production of Transgenic Tall Fescue and Red Fescue Plants by Particle Bombardment of Mature Seed-Derived Highly Regenerative Tissues In this example, an efficient and reproducible transformation system for tall and red fescues using microprojectile bombardment of highly regenerative, green tissues from mature seed-derived embryogenic callus is described.

Materials and Methods

Plant Material and Culture of Explants

Mature seeds of tall fescue (*Festuca arundinacea* Schreb. cv. Ky 31) and red fescue (*Festuca rubra* L. cv. 43F-93) were surface-sterilized for 20 min in 20% (v/v) bleach (5.25% sodium hypochlorite) followed by 3 washes in sterile water. The seeds were placed on 4 different MS (Murashige and Skoog 1962)-based callus-induction media;

(1) D' medium comprising 9.0 µM 2,4-D and 0.1 µM CuSO$_4$ (Cho et al., 1999), (2) D'BC1 medium comprising 9.0 µM 2,4-D, 0.044 µM BAP and 5.0 µM CuSO$_4$, (3) D'BC2 medium comprising 9.0 µM 2,4-D, 0.44 µM BAP and 5.0 µM CuSO$_4$ (Cho et al., 1999) and (4) DBC3 medium comprising 4.5 µM 2,4-D, 2.2 µM BAP and 5.0 µM CuSO$_4$ (Cho et al., 1998b). Five to 7 d after plating, germinating shoots and roots from the mature seeds were completely removed by manual excision. After three weeks of incubation at 24+IC under dim-light conditions (approximately 10 to 30 µEm$^{-2}$s$^{-1}$, 16 h-light), tissues with shiny, nodular and compact structures were selected and subsequently maintained on DBC2 or DBC3 medium, subculturing at 3- to 4-week intervals, to proliferate highly regenerative, green tissues.

Plasmids

Plasmids, pAct1IHPT-4, pAHC20, pAHC15 and pAct1IsGFP-1, were used for transformation. pAct1IHPT-4 (Cho et al., 1998) contains the hygromycin phosphotransferase (hpt)-coding sequence under control of the rice actin 1 promoter (Act1), its intron (Act1I) and the nos 3' terminator. pAHC20 (Christensen and Quail 1996) contains the phosphinothricin acetyltransferase (bar) gene under control of the maize ubiquitin promoter (Ubi1) and its first intron (Ubi1I) and the nos terminator. pAHC15 (Christensen and Quail 1996) contains the uidA gene under control of the maize ubiqutin promoter, its intron and nos 3'. pAct1IsGFP-1 was made by replacing the cauliflower mosaic virus (CaMV) $^{35}$S promoter with the XhoI/NcoI fragment containing the rice actin1 promoter (Act1) and its intron from the pAGR73 plasmid into pBlueSGFP, which contains the synthetic green fluorescent [sgfp(S65T)] gene (Chiu et al., 1996) and nos.

Stable Transformation

Approximately 4- to 5-month-old highly regenerative cultures maintained on D'BC2 or DBC3 medium were used for bombardment. Tissue pieces (3–4 mm) were transferred for osmotic pretreatment to D'BC2 or DBC3 medium further comprising mannitol and sorbitol (0.2 M each). Four hours after treatment with osmoticum, tissues were bombarded as previously described (Lemaux et al., 1996; Cho et al., 1998). Gold particles (1.0 µm), coated with 25 µg of a mixture of pAct1IHPT-4, pAHC20 and pAHC15 at a molar ratio of 1:1:1 for tall fescue or a similar molar ratio of a mixture of pAct1IHPT-4, pAct1IsGFP-1 and pAHC15 for red fescue, were used for bombardment with a Bio-Rad PDS 11000 He biolistic device (Bio-Rad, Hercules, Calif.) at 900 psi. Sixteen to 18 h after bombardment, tissues were placed on osmoticum-free D'BC2 or DBC3 medium supplemented with 30 mg/L hygromycin B and grown at 24±1° C. under dim light (10–30 µEm$^{-2}$s$^{-1}$). At the second round of selection, tissues were transferred to DBC3 medium further comprising 50 mg/L hygromycin B, and from the third round of selection onward, tissues were subcultured at 3- to 4-week intervals on DBC3 further comprising 100 mg/L hygromycin B. When a sufficient amount (a plate) of the putatively transformed highly regenerative tissue was obtained, it was plated on BCI-DM$^-$ (Wan and Lemaux 1994; Cho et al., 1999) or FHG (Hunter 1988) regeneration medium without selective agent and exposed to higher intensity light (approximately 45–55 µEm$^{-2}$s$^{-1}$). After four weeks, regenerated shoots were transferred to soil.

Functional Assays for GUS, PAT and GFP

Plant tissues from each transgenic line were tested for GUS activity by histochemical staining (Jefferson et al., 1987). To determine herbicide-sensitivity of transgenic plants, a section of leaf blade was painted using a cotton swab soaked in a 0.25% solution (v/v) of Basta™ solution (starting concentration, 200 g/L phophinothricin, Hoechst AG, Frankfurt, Germany) plus 0.1% Tween 20; plants were scored 1 week after herbicide application. For Basta spraying, whole plants were sprayed twice with a 0.25% solution (v/v) of Basta™ solution plus 0.1% Tween 20 at 1-week intervals; plants were scored 1 week after the second spray. GFP expression was monitored at high magnification using a Nikon Microphot-5A fluorescent microscope equipped with a Nikon B-2A filter block containing a 450490 excitation filter and a BA520 emission barrier filter.

Genomic DNA Isolation, Polymerase Chain Reaction (PCR) and DNA Blot Hybridization.

To test for the presence of uidA, bar, sgfp(S65T) and hpt, genomic DNA was isolated from leaf tissues of putative, independently transformed lines, derived from different pieces of bombarded tissue that were tracked during selection. Five hundred ng DNA was used in PCR amplifications using the primer sets for uidA, UIDA1 (5'-agcggccgcaTTFACGTCCTGTAGAAACC-3') (SEQ ID NO: 6) plus UID2R (5'-agagctcTCATTGTTTGCCTCCC TG-3') (SEQ ID NO: 7) (Cho et al., 1998); for bar, BAR5F (5'-CATCGAGACAAGCACGGTCAACTTC-3') (SEQ ID NO: 4) plus BAR1R (5'-ATATCCGAGCGCCTCGTGCATGCG-3') (SEQ ID NO: 5) (Lemaux et al., 1996; Cho et al., 1998); for sgfp(S65T), Act1int1 (5'-TCGTC AGGCTTAGATGTG-3') (SEQ ID NO: 1) plus sGFP4R (5'-agaggtaccTTACTTGTACAGCTCGTC-3') (SEQ ID NO: 2); and for hpt, HPT6F (5'-AAGCCTGAACTCACCGCGACG-3') (SEQ ID NO: 8) plus HPT5R (5'-AAGACCAATGCG GAGCATATAC-3') (SEQ ID NO: 9) (Cho et al, 1998). Amplifications were performed in a 25-µl reaction with Taq DNA polymerase (Promega, Madison, Wis.) as described (Cho et al, 1998).

For DNA hybridization analysis of pAHC15 transformants, 14.2 µg and 10 µg of total genomic DNA from leaf tissues of each line from tall fescue and red fescue were digested with BamHI and EcoRI, separated on a 1.0% agarose gel, transferred to Zeta-Probe GT membrane (Bio-Rad, Hercules, Calif.) and hybridized with a radiolabeled uidA-specific probe following manufacturer's instructions. For pAct1IsGFP-1 transformants, µg of total genomic DNA from leaf tissue of each red fescue line was digested with SacI and hybridized with a radiolabeled sgfp(S65T)-specific probe. Probes for uidA, containing 1.48-kb SnaBI-SacI fragment from pD11-Hor3 (Sϕrensen et al., 1996), and for sgfp(S65T), containing 0.72-kb NcoI-NotI fragment from pAct1IsGFP-1, were purified by QIAEX gel extraction kit (QIAGEN, Chatsworth, Calif.) and labeled with α-$^{32}$P-dCTP using random primers.

Results and Discussion

Establishment of In Vitro Culturing System

Previously, protoplasts or embryogenic cell suspension cultures were used as the only successful transformation targets for tall and red fescues (Ha et al., 1992; Wang et al., 1992; Spangenberg et al., 1994, 1995; Dalton et al., 1995, 1998; Kuai and Morris 1995; Bettany et al, 1998). These approaches involved laborious steps and have been difficult to reproduce in terms of initiation and maintenance of cell suspension cultures, and also in isolation of protoplasts. In the present study, four different media, D', DBC1, D'BC2 and DBC3, were tested to establish an efficient in vitro system for culturing and regenerating tall and red fescue tissue that does not involve suspension cultures or protoplasts. A higher callus-induction frequency and larger numbers of embryogenic structures for both tall and red fescues were observed when initiation was on D' or D'BC1 medium compared to D'BC2 or DBC3. More organized tissues were initiated on D'BC2 than on D'. The use of D'BC2 or DBC3 at the initial callus-induction step resulted in high rates of root and shoot formation and low frequencies of callus-induction (data not shown); however, D'BC2 and DBC3 were more optimal for producing and maintaining highly regenerative, green tissues derived from embryogenic callus initiated on D' and D'BC1 media.

Bombardment and selection of transgenic clones. Four- to 5-month-old highly regenerative, green tissues of tall and red fescues were used as transformation targets. These tissues contain multiple, light-green, shoot meristem-like structures. In barley, highly regenerative tissues had physiological and developmental similarities with shoot meristematic tissues from the excised shoot apices of barley cultured on a medium comprising 2,4-D- and BAP (Lemaux et al, 1999). Immunolocalization analyses using maize KNOTTED1 antibody (Zhang et al., 1998), associated with maintenance of the meristematic state in barley shoots, confirmed the visual observations (Lemaux et al., 1999). The highly regenerative tissues of barley, with a high percentage of totipotent cells capable of sustained cell division and competent for regeneration over long periods, represent a high-quality target tissue for transformation. The highly regenerative tissues of tall and red fescues, similar in morphological features to those of barley, were maintained for more than two years with minimal loss in regenerability; similar results were observed with highly regenerative, green tissues of barley (Cho et al, 1998), oat (Cho et al., 1999) and wheat (Kim et al., 1999).

During the selection period on hygromycin, nontransgenic tissue gradually turned brown; in general, the presence of light-green, hygromycin-resistant tall and red fescue tissue was observed at the third or fourth round of selection. Putative transgenic lines were maintained and proliferated on the same medium, until there was sufficient material for regeneration. There is a possibility of obtaining escapes and chimeric plants using these highly regenerative tissues as transformation targets when bialaphos was used as a selective agent because selection pressure is not tight and nontransgenic tissues can proliferate in the presence of transgenic tissue. The selection pressure with hygromycin is much stronger and hygromycin-sensitive tissue is unable to survive following repeated selection (unpublished results). Strong GFP expression was observed in the highly regenerative tissues of red fescue during the selection period. Transgenic materials were used in regeneration attempts and plantlets were transferred to soil in the greenhouse. Using this transformation protocol, 8 independent transgenic tall fescue lines were obtained from 118 pieces of tissue, giving a 6.8% transformation frequency (Table 13). Eleven red fescue lines were obtained from 245 pieces of tissue, giving a 4.5% transformation frequency. Regenerability of the transgenic lines was very high; 8 of 8 (100%) tall fescue lines and 9 of 11 (82%) red fescue lines were regenerable, giving an effective transformation frequency (Lemaux et al., 1999) of 6.8% for tall fescue and 3.7% for red fescue.

TABLE 13

Analysis of transgenic plants

| Plant species | Plasmids used for bombardment | Transgenic lines | PCR hpt | PCR bar | PCR uidA | Transgene expression Basta resistance | Transgene expression GUS activity |
|---|---|---|---|---|---|---|---|
| Tall fescue | pAct1IHPT-4 + pAHC20 + pAHC15 | TFtrans-1 | + | + | + | + | − |
| | | TFtrans-2 | + | + | + | + | + |
| | | TFtrans-3 | + | + | + | + | + |
| | | TFtrans-4 | + | − | + | − | + |
| | | TFtrans-5 | + | − | + | − | + |
| | | TFtrans-6 | + | + | − | + | − |
| | | TFtrans-7 | + | + | + | + | − |
| | | TFtrans-8 | + | + | + | + | − |
| | | | 8/8 = 100% | 6/8 = 75% | 7/8 = 88% | 6/8 = 75% | 4/8 = 50% |

| | Plasmids used for bombardment | Transgenic lines | PCR hpt | PCR sgfp(S65T) | PCR uidA | Transgene expression GFP expression | Transgene expression GUS activity |
|---|---|---|---|---|---|---|---|
| Red fescue | pAct1IHPT-4 + pAct1IsGFP-1 + pAHC15 | RFtrans-1 | + | + | − | + | − |
| | | RFtrans-3 | + | + | + | + | + |
| | | RFtrans-4 | + | + | − | + | − |
| | | RFtrans-5 | + | − | − | − | − |
| | | RFtrans-6 | + | − | + | − | + |
| | | RFtrans-7 | + | + | − | + | − |
| | | RFtrans-8 | + | + | + | + | + |
| | | RFtrans-9 | + | + | + | + | + |
| | | RFtrans-11 | + | − | + | − | + |
| | | RFtrans-12[a] | + | + | − | + | − |
| | | RFtrans-13[a] | + | − | + | − | + |
| | | | 11/11 = 100% | 9/11 = 82% | 6/11 = 55% | 9/11 = 82% | 6/11 = 55% |

[a]nonregenerable

Analysis of Transgenic Plants

PCR analyses of DNA extracted from transgenic tall fescue leaf tissue indicated that hpt/bar, hpt/uidA or hpt/bar/uidA were present in the 8 independently transformed lines (Table 13). Of the approximately 2–5 plants per line examined in the 8 tall fescue lines 100% contained two transgenes, either hpt/bar or hpt/uidA; cotransformation frequency of all three transgenes (hpt/bar/uidA) was 63%.

Of eleven transgenic red fescue lines, 9 had either hpt/uidA or hpt/sgfp(S65T), giving a 82% cotransformation frequency for two transgenes; cotransformation frequency of all three transgenes (hpt/uidA/sgfp(S65T)] was 27%.

Plants from 6 out of 8 (75%) transgenic tall fescue lines were Basta-resistant (Table 13). GUS expression was assessed in putatively transformed leaf tissue or highly regenerative tissue of tall and red fescues (Table 13). Of the 19 independent hygromycin-resistant lines of the two grass species, 10 were positive for GUS activity, giving a 53% coexpression efficiency, 50% for tall fescue lines and 55% for red fescue lines (Table 13). Expression of the red-shifted synthetic gfp [sgfp(S65T)] with optimal human codon usage was tested by fluorescence microscopy in the transgenic red fescue tissues. Strong GFP expression driven by the rice actin promoter was detected in root and other tissues of the transgenic lines; expression of GFP in the leaves was obscured by chlorophyll fluorescence. Nine out of 11 red fescue lines expressed GFP (82%) (Table 13). Coexpression frequency of all three transgenes (hpt/bar/uidA or hpt/uidA/gfp) in transgenic tall fescue and red fescue plants was 25% and 27%, respectively (Table 13).

The presence of the introduced bar, uidA and sgfp(S65T) genes in genomic DNA of transgenic tall and red fescue plants was confirmed by DNA hybridization and PCR (Table 13) analyses. Integration of the introduced uidA and sgfp (S65T) into the genomic DNA of transgenic tall and red fescue lines was further confirmed by DNA hybridization analysis on uncut DNA samples. Genomic DNA that was obtained from three putative transgenic lines (TFtrans-4, -5, RFtrans-8 and -9), transformed with pAHC15 and that was positive for GUS expression and in PCR analysis, yielded the expected 2.15 kb-uidA fragment after digestion with BamHI and EcoRI. Four transgenic red fescue lines (RFtrans-1, -4, -8 and 9) having GFP activity produced after digestion with SacI, a 1.54-kb sgfp(S65T) fragment, containing the 0.47-kb rice actin1 intron, 0.72-kb sgfp(S65T) and 0.35-kb nos. The copy number of the uidA gene ranged from 2 to more than 10 copies per genome; 2–5 copies were observed for sgfp(S65T). The introduced uidA and sgfp (S65T) genes were present in undigested high molecular weight genomic DNA; nontransformed plants did not contain DNA that hybridized to either uidA or sgfp(S65T).

In conclusion, we established an efficient and reliable in vitro culturing system for tall and red fescues using highly regenerative, green tissues derived from mature seeds. These tissues gave rise to multiple green shoots over long periods of time. The use as transformation targets of these highly regenerative tissues, which appear to contain a high percentage of cells competent for sustained division and of less somaclonal variation, minimizes the problem of regenerability loss and leads to obtaining high-quality independently transformed plants.

Example 9

High-Frequency Transformation of Oat Via Microprojectile Bombardment of Seed-Derived Highly Regenerative Cultures In this example, the development from mature oat seed of similar highly regenerative tissues to be used as transformation targets are described. The generation of a large number of independently transformed lines that give rise to transgenic plants are described.

Materials and Methods

Plant Material and Culture of Exptants

Mature seeds of GAF/Park-1, a spring cultivar of oat (Avena sativa L.), were surface-sterilized for 20 min in 20% (v/v) bleach (5.25% sodium hypochlorite) followed by 3 washes in sterile water. Seeds were placed on 3 different MS (Murashige and Skoog, 1962)-based callus-induction media (CIMs) comprising different combinations of 2,4-dichlorophenoxyacetic acid (2,4-D), 6-benzylaminopurine (BAP) and $CuSO_4$ (Table 14): (1) D'-2.0 mg/L 2,4-D and 0.1 µM $CuSO_4$, (2) D'BC2–2.0 mg/L 2,4-D, 0.1 mg/L BAP and 5.0 µM $CuSO_4$ and (3) DBC3—comprising 1.0 mg/L 2,4-D, 0.5 mg/L BAP and 5.0 µM $CuSO_4$ (Cho et al., 1999b). Five to 7 days after initiation, germinating shoots and roots were completely removed by manual excision. After 3 weeks of incubation at 24±1° C. under dim light (approximately 10 to 30 µE, 16 h-light), high-quality tissues with nodular and embryogenic structures were selected and maintained on each medium, subculturing at 3- to 4-week intervals.

Shoot Regeneration Test

Ten pieces (4 to 6 mm) of 5- and 7-month-old oat tissue, which had been maintained on each medium, were selected and placed on BCI-DM⁻ media (phytohormone-free CIMs) for regeneration at a light intensity of approximately 45 to 55 gE; each treatment had 4 replicates. After four weeks on regeneration medium, the numbers of pieces of highly regenerative tissue producing green sectors and the numbers of shoots per piece of highly regenerative tissue were counted. If more than one leaf" arose from the same tissue base, it was counted as one shoot.

Plasmids

Plasmids, pAct1IHPT-4 and pAHC15, were used for transformation. pAct1IHPT-4 (Cho et al., 2000) contains the hygromycin phosphotransferase (hpt) gene under control of the rice actin1 promoter (Act1), its intron (Act1I) and the nos 3' end. pAHC15 (Christensen and Quail, 1996) contains the uidA gene under control of the maize ubiqutin UbiI promoter and intron (UbiI/Ubi1I) and nos.

Particle Bombardment and Stable Transformation

Approximately four- to five-month-old highly regenerative tissues, induced on D'BC2 medium and maintained on D'BC2 or DBC3 medium, were used as targets for bombardment. Tissues (3 to 4 mm) were transferred for osmotic pretreatment to D'BC2 or DBC3 medium further comprising equimolar amounts of mannitol and sorbitol to give a final concentration of 0.4 M. After 4 h, tissues were bombarded as previously described (Lemaux et al., 1996) with modifications. In summary gold particles (1.0 lm; Analytical Scientific Inc., Alameda, Calif.) were coated with 25 µg of a 1:1 molar ratio of pAct1IHPT-4 and pAHC15 followed by bombardment using a PDS-1000 He biolistic device (Bio-Rad, Inc., Hercules, Calif.) at 900 psi. Sixteen to 18 hr after bombardment, tissues were moved to D'BC2 or DBC3 medium without osmoticum or selective agent and grown at 24±1° C. under dim light.

Following the initial 10- to 14-day culturing period, each tissue was broken into 1 to 3 pieces (3 to 4 mm), depending on initial tissue size, and transferred to D'BC2 or DBC3 medium with 20 mg/L hygromycin B (Boehringer Mannheim, Mannheim, Germany). From the second-round selection onward, tissues were subcultured at 3- to 4-week intervals on the same medium further comprising 20 mg/L hygromycin B. When sufficient rapidly growing material was available, tissues were moved to nonselective BCI-DM⁻ or FHG regeneration medium (Hunter, 1988; *Wan and Lemaux*, 1994) and exposed to higher intensity light (approximately 45–55 µE). After four weeks, regenerated shoots were transferred to Magenta boxes containing BCI-DM⁻ without selective agent. When the shoots reached the top of the box, plantlets were transferred to the soil.

Histochemical GUS Assay

Highly regenerative, transgenic tissue and leaf material from $T_0$ to $T_2$ plants transformed with a mixture of pAct1IHPT-4 and pAHC15 were tested for GUS activity by histochemical staining (Jefferson et al, 1987), using 5-bromo-4-chloro-3-indoyl-β-D-glucuronic acid (X-gluc) (Gold Biotechnology, Inc., St. Louis, Mo.). Samples were incubated overnight at 37° C. in GUS assay buffer before being scored.

Genomic DNA Isolation, Polymerase Chain Reaction (PCR) and DNA Blot Hybridization Total genomic DNA from leaf tissues of putatively transformed plants was purified as described (Dellaporta, 1993). To test for the presence of uidA and hpt in genomic DNA of putatively transformed lines, 500 ng of genomic DNA was amplified by PCR using the primer set, UIDA1 (5'-agcggccgcaTTACGTCCTGTAGAAACC-3') (SEQ ID NO: 6) plus UID2R (5'-agagctcTCATTGTTTGCCTCCCTG-3') (SEQ ID NO: 7) (Lemaux et al., 1996) or HPT6F (5'-AAGCCTGAACTCACCGCGACG-3') (SEQ ID NO: 8) plus HPT5R (5'-AAGACCAATGCGGAGCATATAC-3') (SEQ ID NO: 9) (Cho et al., 1998b), respectively. Amplifications were performed in a 25-µl reaction with Taq DNA polymerase (Promega, Madison, Wis.) according to a protocol described by Cho et al., (Cho et al., 1998b). For DNA hybridization analysis, 10 µg of total genomic DNA from leaf tissue of each line was digested with BamHI and EcoRI, separated on a 1.0% agarose gel, transferred to Zeta-Probe GT membrane (Bio-Rad, Hercules, Calif.) and hybridized with a radiolabeled uidA specific probe following manufacturer's instructions. The uidA containing 1.9-kb BamHI-SacI fragment from pAHC15 was isolated with QIAEX gel extraction kit (QIAGEN, Chatsworth, Calif.) and labeled with α-$^{32}$P-dCTP using random priming according to manufacturer's instructions (Promega, Madison, Wis.).

Results

Establishment of an In Vitro System

To establish a highly efficient in vitro system for culturing and regenerating oat tissue, three different media were tested (Table 14). A higher callus induction frequency and larger numbers of embryogenic structures were observed on D' medium and D'BC2 medium than on DBC3. The use of DBC3 at the initial callus-induction step resulted in high rates of seed germination and low frequencies of callus induction (data not shown); however, DBC3 was optimal for maintaining highly regenerative tissues derived from embryogenic callus initiated on D' or DBC2 medium (Table 14).

The addition of BAP and copper to 2,4-D in D'BC2 and DBC3 medium resulted in the production of greater numbers of shoots per piece of tissue on regeneration medium compared to tissues derived from D' medium (Table 14). The frequency of shoot regeneration was increased 2.3- to 4.1-fold and 1.8- to 4.4-fold with D'BC2 and DBC3 medium, respectively, compared to D' medium. The extent of negative effects of the length of culture time on regenerability varied with the three media tested (Table 14). The tissues on D' medium resulted in a smaller percentage of regenerated shoots at 7 months compared to 4 months than did tissues from the other two media; tissues from DBC3 yielded the highest percentage. Tissues maintained on DBC3 appeared to maintain regenerability better than tissues on the other two media.

TABLE 14

Regenerability of oat tissues grown on different media

| Medium | Composition | | | Tissue age (months) | # tissues with green sectors/ total # pieces of tissue | # shoots/ tissue piece | Tissue age (months) | # shoots/ tissue piece |
| | 2,4-D (mg/L) | BAP (mg/L) | CuSO₄ (µM) | | | | | |
| --- | --- | --- | --- | --- | --- | --- | --- | --- |
| D' | 2.0 | 0 | 0.1 | 5 | 9.5 ± 1.0/10 | 4.6 ± 0.7 | 7 | 1.4 ± 0.8 |
| BC2 | 2.0 | 0.1 | 5.0 | 5 | 10.0 ± 0.0/10 | 10.8 ± 1.0 | 7 | 5.7 ± 1.6 |
| DBC3[a] | 1.0 | 0.5 | 5.0 | 5 | 10.0 ± 0.0/10 | 8.2 ± 0.4 | 7 | 6.1 ± 1.6 |

Ten pieces (4 to 6 mm) of 5- and 7-month-old tissue from each treatment were transferred to regeneration medium; after 4 weeks, the numbers of shoots were counted. Values represent means ± standard deviation of four replicates for each treatment.
[a]Callus was initiated on D'BC2 medium and after 3 weeks tissues were transferred and maintained on DBC3 medium.

Bombardment and Selection of Transgenic Tissues

Four- to 5-month-old highly regenerative tissues, initiated on D'BC2 and maintained on D'BC2 or DBC3 medium, were used for bombardment. During the selection period on hygromycin nontransgenic tissues gradually turned brown; the presence of light-green, hygromycin-resistant tissues was generally observed at the third round of selection. Putative transgenic tissues were maintained and proliferated on the same medium after the 4th round of selection, until sufficient tissue was obtained for regeneration. Using this transformation protocol, 84 independent transgenic lines were obtained from 327 pieces of bombarded tissue, giving a 26% transformation frequency (Table 15). Since all transformed lines were regenerable, this gives an effective transformation frequency [total # lines regenerable/total # lines; 10] of 26%. To date 63% (²⁴/₃₈) of independent $T_0$ lines were fertile (Table 15), but with varying levels of seed set (data not shown).

TABLE 15

Summary of oat transformation experiments

| Tissue age (days after induction) | Maintenance Medium | % Transformation frequency (# independents/ # bombarded explants) | % Coexpression frequency (# lines with GUS activity/ # total lines) | % regenerability (# regenerable lines) | % fertility (# fertile lines/ # lines regenerated |
|---|---|---|---|---|---|
| 112 | D'BC2[a] | 18.6% (21/113) | 66.7% (14/21) | 100% (21) | 58.3% (7/12) |
|  | DBC3[b] | 17.8% (8/45) | 62.5% (5/8) | 100% (8) | 62.5% (5/8) |
| 133 | D'BC2 | 33.0% (34/103) | 73.5% (25/34) | 100% (34) | 50.0% (3/6) |
|  | DBC3 | 31.8% (21/66) | 71.4% (15/21) | 100% (21) | 75.0% (9/12) |
| Total |  | 25.7% (84/327) | 70.2% (59/84) | 100% (84) | 63.2% (24/38) |

[a]D'BC2 medium is callus-induction medium comprising 2.0 mg/L 2,4-D, 0.1 mg/L BAP and 5.0 μM cupric sulfate.
[b]DBC3 medium is callus-induction medium comprising 1.0 mg/L 2,4-D, 0.5 mg/L BAP and 5.0 μM cupric sulfate.

Analysis of $T_0$ Plants and their Progeny

Presence of uidA in genomic DNA of independent to oat lines was confirmed by DNA hybridization analysis. Genomic DNA from to plants of 10 out of 11 lines tested that were transformed with pAHC15 and positive in PCR analysis yielded the expected 2.2-kb uidA fragment. In some cases other fragments were present after digestion with BamHI and EcoRI; line ASGPB'-17 produced only a larger-sized fragment. Copy numbers of uidA ranged from one to more than 10 copies per genome. Histochemical analysis for GUS activity in to plants derived from the putative transgenic lines provided additional evidence of stable transformation. GUS expression was detected in putatively transformed cultured callus tissues, and leaf, anther, ovary and stigma tissues. Out of 84 independent hygromycin-resistant lines examined, 70 lines contained both genes, giving a 83% cotransformation frequency; 59 were positive for GUS expression, giving a 70% coexpression frequency (Table 2).

Segregation of GUS expression was analyzed in $T_1$ progeny of eight fertile transgenic oat lines (ASGPB'-1,4, -8, -10, ASGPC-5, -6, -100 and -105); one of these lines ASGPB'-10 did not express GUS in to plant tissue (Table 16). Of the seven lines that expressed GUS in to plants, GUS expression was detected in $T_1$ progeny from six of these lines (ASGPB'-1, 4, -8, ASGPC-5, -6, -100 and -105); one line (ASGPC-6) did not express GUS in the $T_1$ plants (Table 16). Of the six GUS-expressing lines, only one line (ASGPB'-4) segregated in the expected 3:1 ratio, four lines (ASGPB'-1, -8, ASGPC-100 and -105) at lower than 3:1 and the remaining line (ASGPC-5) at higher than 3:1.

GUS expression and physical transmission of the transgenes, uidA and hpt, were also analyzed in two different $T_1$ segregating populations (ASGPB'-4 and ASGPC-100). Expression of GUS in $T_1$ progeny of ASGPB'4 was consistent with the presence of uidA, as assessed by PCR. From both ASGPB'4 and ASGPC-100 all $T_1$ plants that were PCR-positive for uidA were also PCR positive for hpt. Expression of GUS in ASGPB'-4 was strong, and in ASGPC-100 weak. All seven GUS-positive $T_1$ progeny of ASGPB'-4 produced $T_2$ progeny with strong GUS expression; three putative homozygous progeny (ASGPB'-4-3, -6 and -8) were obtained. Five of six GUS-positive $T_1$ progeny from ASGPC-100 tested had weak GUS expression in $T_2$ progeny (ASGPC-100-1, -2, -3, -4, -5, and -7); ASGPC-100-6 did not express GUS.

TABLE 16

Histochemical GUS activity in $T_0$ and $T_1$ plants

| Transgenic line[a] | GUS activity in $T_0$ leaf tissue | GUS activity in $T_1$ leaf tissue (+:−) |
|---|---|---|
| ASGPB'-1 | + | 2:26 |
| ASGPB'-4 | + | 18:4[b] |
| ASGPB'-8 | + | 15:18 |
| ASGPB'-10 | − | 0:24 |
| ASGPC-5 | + | 25:0 |
| ASGPC-6 | + | 0:33 |
| ASGPC-100 | + | 16:18 |
| ASGPC-105 | + | 4:21 |

[a]ASGPB' lines were initiated, maintained and selected on D'BC2 medium while ASGPC lines were initiated on D'BC2, maintained and selected on DBC3 medium.
[b]Analyses using the $X^2$-test indicated that the segregation ratios of $T_1$ progeny were not significantly different from the expected 3:1 (at α = 0.05).

Discussion

In this example, eight-four transgenic lines of oat were obtained using microprojectile bombardment of 327 pieces of highly regenerative, green tissue derived from embryogenic callus induced from mature seeds. The transformation frequency (the number of independent transformants per total number of explants) was 26%, higher than that reported previously using other target tissues (Somers et al., 1992; Torbert et al., 1995; Torbert et al., 1998a; Torbert et al., 1998b; Zhang et al., 1999b).

One of the main factors responsible for the high transformation frequency reported in this study is likely to be the use of highly regenerative, green tissues as transformation targets. These tissues contain multiple, light-green, shoot meristem-like structures. In oat and barley the expression of a gene associated with maintenance of the meristematic state, a knotted 1 homologue, was studied in shoot meristem cultures derived from the excised shoot apex in oat (Zhang et al., 1999b) and barley (Zhang et al., 1998) and from highly regenerative tissue (barley only) (Lemaux et al., 1999). The pattern was similar in the two tissues, suggesting that they have physiological similarities (Lemaux et al., 1999).

Highly regenerative, green tissues with a high percentage of cells capable of sustained cell division and competent for regeneration over long periods represent a high-quality target tissue for transformation. The highly regenerative tissues of oat could be maintained for more than one and a half years with minimal loss in regenerability; similar results were observed with highly regenerative, green tissues of barley (Cho et al., 1998b). All transgenic lines (100%) in this study produced multiple green shoots and were regenerable. In contrast to this situation, regenerability of transgenic oat lines from immature embryo-derived cultures was 36% (Torbert et al., 1996), from mature embryo-derived cultures, 58% (Torbert et al., 1998a) and from leaf base-derived cultures, 91% (Gless et al., 1998b). Of the transgenic lines derived from cultured axillary meristematic tissue, 100% were regenerable, which is not unexpected given the developmental similarities between the highly regenerative, green tissues and the shoot meristem cultures (Zhang et al., 1999b; Lemaux et al., 1999).

Despite the improvement in the in vitro culture system and regenerability of the transformed cultures in this study, on average only 63% of transgenic lines yielded plants that were fertile; of those varying levels of seed set were observed. Tissues maintained on DBC3 appeared to have a higher level of fertility (70%) versus those maintained on D'BC2 (56%). This might be due to the fact that tissues maintained on DBC3 were more organized than those on D'BC2 (Cho et al., 1998b) and therefore gave rise to more phenotypically normal plants. The phenomenon of reduced fertility or sterility has been observed frequently in transgenic cereals (Cho et al., 1998b; Wan and Lamaux, 1994; Gordon-Kamm et al., 1990; Vasil et al., 19, 1992), especially in oat (Somers et al., 1992; Torbert et al., 1995; Torbert et al., 1998a; Torbert et al., 1998b; Zhang et al., 1999b; Cho et al., 1998c). Previously Somers et al., (1992) reported that 34% (38 of 111) of transgenic lines generated from cell suspension cultures or embryogenic calli derived from immature embryos gave rise to green plants; only one line was fertile. Fertility of transgenic oat plants produced from immature embryo-derived calli, mature seed-derived calli and leaf base segments ranged from 19 to 64% (Torbert et al., 1995, 1998a; Gless et al., 1998b). Recently it was reported that 71% of transgenic lines produced from cultured axillary meristematic tissue were fertile (Zhang et al., 1999b), comparable to the rate of plants maintained on DBC3 in this study. In general, the reduction in fertility in transgenic plants, relative to plants that have not undergone in vitro culture, might be related to the cytological instability that occurs during in vitro culture period associated with transformation or to the physiological changes in the transgenic plants in terms of the synchrony of pollen and egg development.

PCR analyses on DNA extracted from $T_1$ leaf tissue indicated that hpt alone or hpt and uidA were present in all 84 transgenic lines. Seventy lines contained both genes, giving a 83% cotransformation frequency; coexpression frequency was 70%. DNA hybridization analysis confirmed the presence of uidA in the genomic DNA of all 11 transgenic lines analyzed, with copy numbers ranging from one to more than 10 copies, similar to that reported in earlier studies using microprojectile bombardment of (Somers et al., 1992; Pawloski et al., 1998).

Most GUS-positive lines in our study had strong GUS expression uniformly throughout the highly regenerative tissues; however, tissues from some transgenic lines were chimeric with respect to GUS expression (data not shown). This could be due to transgene silencing in certain parts of the tissue, survival of nontransformed tissues under the selection pressure used, or the fact that two or more transgenic lines were present in the same piece of bombarded tissue and one of the lines did not have or express GUS. Expression of GUS was shown to be stably inherited in $T_1$ progeny of 6 out of 7 GUS-expressing $T_0$ plants tested. In general the level of GUS expression observed in $T_0$ plants was stably inherited in their progeny.

$T_0$ lines with a single site of transgene integration should give a segregation ratio for transgene expression of 3:1, but one line (ASGPB'-4) with a single copy did give this expected ratio. The cause of some lines having a lower than 3:1 ratio could be due to several factors. In some earlier reports lower segregation ratios were due to loss or low-rates of physical transmission of the transgene(s) to progeny (Pawlowski et al., 1998; Pawlowski and Somers, 1996; Pawlowski et al., 1994). This is not likely to be the explanation for ASGPC-100 since PCR analysis of DNA from $T_1$ progeny of this line indicated that uidA was present. The more likely explanation for the distorted segregation ratios is transgene silencing, which has been reported to occur in transgneic oat plants (Zhang et al., 1999b; Somers, 1999; Pawlowski et al., 1998; *Pawlowski and Somers,* 1996). Lack of transgene expression in progeny may also be due to mutations, chromosomal changes and methylation changes, which have the potential to exert pleiotropic effects on transgene expression and inheritance (Pawlowski and Somers, 1996).

For skewed expression ratios higher than 3:1, it is possible that the two genes could be integrated into different chromosomes in the transgenic plants, causing them to segregate in the higher ratio. Of the two transgenic lines studied in the $T_2$ generation, expression of GUS was stably transmitted to most $T_2$ plants (strong GUS expression in ASGPB'-4 plants and weak GUS expression in ASGPC-100) plants; putative homozygous plants were obtained from ASGPB'-4. The stability of transgene expression in this event might be due to the fact that it existed as a single copy and that it integrated into a chromosomal location that supported stable expression.

In conclusion, an efficient and reproducible in vitro culturing system for oat using materials derived from mature seeds was established. The highly regenerative, green tissues gave rise to multiple green shoots over long periods of time. The use as transformation targets of these highly regenerative tissues, which appear to contain a high percentage of cells competent for sustained division, minimizes the problem of regenerability loss and leads to a high frequency of obtaining independently transformed events with high fertility.

Example 10

High Frequency of Cytogenetic Aberration in Transgenic Oat (*Avena sativa* L.) Plants In this example, chromosomal aberration in transgenic oat plants produced by microprojectile bombardment of mature seed-derived highly regenerative, green tissues was examined. To evaluate the influence of transformation process compared to the in vitro culture process alone, cytological data was also obtained from nontransgenic oat plants, produced from tissue manipulated in an identical manner.

Materials and Methods

Plant Material and Culture of Explants

Mature seeds of GAF/Park-1, a spring cultivar of oat (*Avena sativa* L.), were used for in vitro culture as previously described (Cho et al., 1999b). Sterilized-seeds were placed on 2 different MS-based (Murashige and Skoog 1962) callus-induction media for initial callus induction: (1) D' comprising 2.0 mg/L 2,4-D and 0.1 µM $CuSO_4$ and (2) D'BC2 comprising 2.0 mg/L 2,4-D, 0.1 mg/L BAP and 5.0 µM $CuSO_4$ (Cho et al., 1999b). Five to 7 days after initiation, germinating shoots and roots were completely removed by manual excision. After 3 weeks of incubation at 24±1° C. under dim light (approximately 10 to 30 µE, 16 h-light), high-quality tissues with nodular, embryogenic structures were selected and maintained on each medium, subculturing at 3- to 4-week intervals. Three different in vitro culturing procedures were used: (1) D' (Cho et al., 1999b) alone for initiation and maintenance, (2) D'BC2 (Cho et al., 1999b) alone for initiation and maintenance, and (3) D'BC2/DBC3; D'BC2 for initiation and DBC3 (comprising 1.0 mg/L 2,4-D, 0.5 mg/L BAP and 5.0 µM CuSO$_4$) (Cho et al., 2000) for maintenance.

Production of Nontransgenic Plants

Seven- to eight-month-old embryogenic calli or highly regenerative tissue were used for regeneration on FHG (Hunter, 1988) or BCI-DM-medium (phytohormone-free callus-induction medium) (Wan and Lemaux, 1994). Regenerated shoots were transferred to Magenta boxes and, when shoots reached the top of the box, plantlets were transferred to soil in the greenhouse.

Production and Analysis of Transgenic Plants

Transgenic plants were obtained via microprojectile bombardment as previously reported (Cho et al., 1999b). Briefly, highly regenerative tissues were initiated from mature seed-derived embryogenic callus on D'BC2 medium and subsequently maintained on either D'BC2 or DBC3 medium. Target tissues, approximately 4 to 5 months old, were osmotically treated and then bombarded with a mixture of 2 plasmids: pAct1IHPT-4 (Cho et al., 2000) comprising the hygromycin phosphotransferase (hpt) gene under the control of the rice actin1 promoter (Act1) and its intron, and pAHC15 (Christensen and Quail, 1996) comprising uidA (β-glucuronidase gene, gus) under control of the maize ubiquitin promoter (Ubi1) and intron (Ubi1I). When sufficient rapidly growing tissues were identified on a medium comprising hygromycin, they were transferred to BCI-DM$^-$ or FHG medium without selection for regeneration. The regenerated shoots were transferred to Magenta boxes containing BCI-DM without selective agent. When the shoots reached the top of the box, plantlets were transferred to soil in the greenhouse.

Transgenic plants were identified by PCR and/or DNA blot hybridization analyses (Cho et al., 1999b). Cytological analysis of to oat plants was performed as previously described (Cho et al., 2000) using healthy root tips collected from young plants grown in the greenhouse. For cytological analysis of T$_1$ plants, T$_1$ seeds of 9 independent transgenic lines were planted in soil and root tips were harvested from individual young plants. After pre-treatment in saturated 1-bromonaphthalene solution overnight at 4° C., root meristems were fixed in 1:3 glacial acetic acid:ethanol and stored at 4° C. Root meristems were hydrolyzed in 1M HCl at 60° C. for 5–7 min, stained in Feulgen solution and squashed on a glass slide in a drop of 1% aceto-carmine. Chromosomes were counted from at least five well-spread cells per plant.

Results

Chromosomal Aberration in Nontransgenic Plants

Chromosome numbers were counted in cells of the root meristem of nontransgenic oat plants regenerated from 7- to 8-month-old calli or highly regenerative tissues, initiated and maintained under each of three different culturing schemes. Calli were initiated and maintained on D' medium and highly regenerative tissues were initiated on D'BC2 medium and maintained on either D'BC2 or switched to DBC3 medium. These tissues were comparable in age to that from which transgenic plants were regenerated. Four plants out of 9 (44%) regenerated from D' medium had chromosomal aberrations, three with aneuploidy (2n=6x=40, 41), and one with a structural variation, 2n=6x=40+1f (Table 17). Two out of 14 (14%) from D'BC2 medium were aneuploid (2n=6x=41) without any structural variation and the remaining 12 plants had a normal chromosome complement with 2n=6x=42. All 18 plants regenerated from D'BC2/DBC3 medium were normal in chromosome number. The overall rate of chromosomal variation in nontransgenic plants from all media was 15% (6 of 41); only 6% (2/32) of the regenerated plants from D'BC2 or D'BC2/DBC3 medium were aneuploid. Fertility of nontransgenic plants regenerated from D', D'BC2 and D'BC2/DBC3 medium was 78%, 93% and 100%, respectively.

TABLE 17

Analysis of chromosomal variation and fertility in nontransgenic oat plants

| Culture medium[a] | # plants analyzed | Chromosome number | | | | % aberration | Fertility |
|---|---|---|---|---|---|---|---|
| | | 40 | 40 + 1f | 41 | 42 | | |
| D' | 9 | 1 | 1 | 2 | 5 | 44.4% (4/9) | 77.8% (7/9) |
| D'BC2 | 14 | 0 | 0 | 2 | 12 | 14.3% (2/14) | 92.9% (13/14) |
| D'BC2/DBC3 | 18 | 0 | 0 | 0 | 18 | 0% (0/18) | 100% (18/18) |

[a]Nontransgenic plants were obtained from 7- to 8-month-old tissues, comparable in age to that from which transgenic plants were regenerated, cultured using 3 different in vitro culturing schemes: (1) D' alone for initiation and maintenance, (2) D'BC2 alone for initiation and maintenance and (3) D'BC2 for initiation and DBC3 for maintenance. D' medium is callus-induction medium comprising 2.0 mg/L 2,4-D and 0.1 µM CuSO$_4$; D'BC2 contains 2.0 mg/L 2,4-D, 0.1 mg/L BAP and 5.0 µM CuSO$_4$ and DBC3 medium contains 1.0 mg/L 2,4-D, 0.5 mg/L BAP and 5.0 µM CuSO$_4$.

Chromosomal Aberration In Transgenic Plants

Chromosomes were analyzed in cells of root meristem of T$_0$ plants regenerated from independently transformed oat lines. Of forty-eight independent transgenic lines examined, all plants regenerated from 20 lines (42% of lines) had the karyotypically normal complement (2n=6x=42) without detectable aberration, while at least one plant regenerated from each of the other 28 lines (58% of lines) was karyotypically abnormal, aneuploid (2n=6x=40 or 41) or aneuploid with structural changes (2n=6x=38+1dl, 39+1 dl, 40+1dl, 41+1dl, 40+1f and 41+1f) (Table 18). Frequent differences in chromosomal status were observed among plants regenerated from same to line (lines ASGPB'-4, -8, -10, -14, -18, -30, -52, -76, -79, -87, ASGPC-102, -105, -108, -115 and -122); these 15 T$_0$ lines had both cytologically normal and abnormal plants. There was no change in ploidy level of the transgenic oat plants.

No significant difference in frequency of cytological variation was observed between plants regenerated from lines from the two different culturing systems used for transformation; 57% (16 of 28) for plants from lines maintained solely on D'BC2 medium and 60% (12 of 20) for plants from lines initiated on D'BC2 and switched to DBC3 (D'BC2/DBC3) (Table 18). The overall rate of chromosomal variation in transgenic plants from the two media was 58%; plants from 28 of 48 lines had chromosomal abnomalities. From the 48 independent lines shown in Table 18, a total of 112 different plants were analyzed (Table 19). Of the total number of transgenic plants, fifty-two percent (58 of 112) had a normal chromosome complement (2n=6x=42), but the remaining 54 plants (48%) had chromosomal aberrations, such as aneuploidy (2n=6x=41, 40), deletion (2n=6x=38+1dl, 39+1dl, 40+1dl, 41+1dl) and acentric fragments (2n=6x=40+1f, 41+1f).

Fertility of transgenic plants regenerated from D'BC2 and D'BC2/DBC3 medium was 46% and 60%, respectively (Table 18). Of the twenty independent transgenic lines with a normal chromosomal complement (2n=6x=42), however, plants regenerated from 15 lines (75%) were fertile (Table 18). Of transgenic oat lines with chromosomal abnormalities, only 36% ($^{10}/_{28}$) of the plants from these lines were fertile (Table 18), but they had low seed set (data not shown).

Chromosomal Aberration in Transgenic Progeny

Chromosomes were also analyzed in $T_1$ plants of 9 independent transgenic lines (Table 20). All $T_1$ plants derived from 6 cytologically normal $T_0$ lines (ASGPB'-4, -8, -66, ASGPC-6, -100, -105) had normal chromosomal numbers (2n=6x=42). In contrast, chromosomal variation was frequent in $T_1$ plants derived from the remaining 3 $T_0$ lines that had abnormal chromosomal numbers of 2n=6x=40 or 41 (i.e. ASGPB'-10, ASGPC-3, and ASGPC-118). Some karyotypically normal $T_1$ plants with 2n=6x=42 were produced from one cytologically abnormal $T_0$ line (ASGPC-3, 2n=6x=41).

TABLE 18

Analysis of chromosomal variation and fertility in transgenic oat plants

| Transformation scheme[a] | Transgenic lines ($T_0$) | # plants analyzed | chromosome no. (2n) | Fertility |
|---|---|---|---|---|
| D'BC2 | ASGPB'-1 | 3 | 42 | + |
|  | ASGPB'-2 | 1 | 42 | + |
|  | ASGPB'-4 | 3 | 41, 42 | + |
|  | ASGPB'-5 | 1 | 42 | − |
|  | ASGPB'-6 | 1 | 42 | + |
|  | ASGPB'-7 | 3 | 40, 41 | − |
|  | ASGPB'-8 | 5 | 41 + 1dl[b], 42 | + |
|  | ASGPB'-10 | 3 | 41, 42 | + |
|  | ASGPB'-13 | 3 | 42 | − |
|  | ASGPB'-14 | 4 | 41, 42 | − |
|  | ASGPB'-16 | 1 | 42 | + |
|  | ASGPB'-17 | 2 | 40 | − |
|  | ASGPB'-18 | 2 | 40, 42 | − |
|  | ASGPB'-28 | 1 | 42 | − |
|  | ASGPB'-30 | 2 | 39 + 1dl, 42 | − |
|  | ASGPB'-52 | 2 | 41, 42 | − |
|  | ASGPB'-53 | 1 | 41 | − |
|  | ASGPB'-56 | 1 | 42 | + |
|  | ASGPB'-61 | 2 | 42 | + |
|  | ASGPB'-66 | 3 | 40, 40 + 1f[c], 41 | − |
|  | ASGPB'-67 | 1 | 40 | − |
|  | ASGPB'-74 | 4 | 42 | + |
|  | ASGPB'-76 | 3 | 41, 42 | − |
|  | ASGPB'-79 | 3 | 40, 41, 42 | − |
|  | ASGPB'-81 | 1 | 41 | − |
|  | ASGPB'-84 | 2 | 42 | + |
|  | ASGPB'-86 | 4 | 42 | + |
|  | ASGPB'-87 | 2 | 41, 42 | + |
| subtotal | 28 lines | | % aberrant = 57.1% (16/28) | % fertile = 46.4% |
| D'BC2/DBC3 | ASGPC-2 | 2 | 40 | − |
|  | ASGPC-3 | 3 | 41 | + |
|  | ASGPC-5 | 2 | 42 | + |
|  | ASGPC-6 | 4 | 42 | + |
|  | ASGPC-7 | 2 | 42 | − |
|  | ASGPC-9 | 4 | 41 + 1dl | − |
|  | ASGPC-100 | 3 | 41 | + |
|  | ASGPC-102 | 3 | 41 + 1dl, 42 | + |
|  | ASGPC-104 | 2 | 42 | + |
|  | ASGPC-105 | 3 | 41 + 1dl, 42 | + |
|  | ASGPC-107 | 1 | 42 | + |
|  | ASGPC-108 | 3 | 40 + 1dl, 41, 42 | − |
|  | ASGPC-109 | 1 | 42 | + |
|  | ASGPC-110 | 1 | 41 + 1dl | + |
|  | ASGPC-115 | 3 | 40, 42 | − |
|  | ASGPC-116 | 1 | 42 | + |
|  | ASGPC-117 | 2 | 40 + 1f, 41 + 1f | − |

TABLE 18-continued

Analysis of chromosomal variation and fertility in transgenic oat plants

| Transformation scheme[a] | Transgenic lines (T$_0$) | # plants analyzed | chromosome no. (2n) | Fertility |
|---|---|---|---|---|
| | ASGPC-118 | 2 | 40 | + |
| | ASGPC-120 | 3 | 42 | + |
| | ASGPC-122 | 3 | 38 + 1dl, 42 | − |
| subtotal | 20 lines | % aberrant = | 60.0% (12/20) % | fertile = 60.0% |
| Total | 48 lines | 112 | 58.3% (28/48) % | fertile = 52.1% |

[a]Transgenic plants were obtained from tissue cultured using 2 different in vitro culturing procedures; ASGPB' lines were initiated and selected on D'BC2 medium while ASGPC lines were initiated on D'BC2, and subsequently maintained and selected on DBC3 medium. D'BC2 medium is callus-induction medium comprising 2.0 mg/L 2,4-D, 0.1 mg/L BAP and 5.0 μM CuSO$_4$ and DBC3 contains 1.0 mg/L 2,4-D, 0.5 mg/L BAP and 5.0 μM CuSO$_4$.
[b]Deletion of chromosome segment.
[c]Small acentric fragment.

TABLE 19

Summary of variation in chromosome number in transgenic oat plants

| # plants analyzed[a] | Chromosome number | | | | | | | | | | % aberration[b] |
|---|---|---|---|---|---|---|---|---|---|---|---|
| | 38 + 1dl[c] | 39 + 1dl | 40 | 40 + 1f[d] | 40 + 1dl | 41 | 41 + 1f | 41 + 1dl | 42 | | |
| 112 | 2 | 1 | 12 | 2 | 1 | 26 | 1 | 9 | 58 | | 48.2% (54/112) |

[a]Differing numbers of T$_0$ plants derived from each of a total of 48 independent lines.
[b]% aberration = # aberrant plants/total # plants analyzed.
[c]Deletion of chromosome segment.
[d]Small acentric fragment.

TABLE 20

Analysis of chromosome number in T$_1$ plants

| Transgenic line (T$_0$) | # plants analyzed | Chromosome # in T$_0$ plants | Chromosome # in T$_1$ plants[a] |
|---|---|---|---|
| ASGPB'-4 | 3 | 42 | 42 (3)[a] |
| ASGPB'-8 | 3 | 42 | 42 (3) |
| ASGPB'-10 | 5 | 41 | 40 (4), 41 (1) |
| ASGPB'-66 | 4 | 42 | 42 (4) |
| ASGPC-3 | 5 | 41 | 41 (3), 42 (2) |
| ASGPC-6 | 4 | 42 | 42 (4) |
| ASGPC-100 | 4 | 42 | 42 (4) |
| ASGPC-105 | 5 | 42 | 42 (5) |
| ASGPC-118 | 8 | 40 | 40 (8) |

[a]Values in parentheses are the numbers of transgenic plants observed at that chromosome number.

Discussion

Genomic instability, as reflected by gross differences in numbers and structure of chromosomes, has been studied in allohexaploid oat plants derived from nontransgenic in vitro cultures. In the present study, only 2 of 32 (6%) of nontransgenic, regenerated plants from 7- to 8-month-old highly regenerative tissues cultured on D'BC2 or D'BC2/DBC3 media for initiation and maintenance were cytologically abnormal. In several other studies the meiotic chromosomes of nontransgenic oat plants were analyzed (Cummings et al., 1996; McCoy et al., 1982; Johnson et al., 1987B, 1987C). McCoy et al., (1982) described many types of chromosomal alterations, monosomy, trisomy, heteromorphic pairs, fragments, deletion, inversions and interchanges in the meiotic cells of regenerated plants from two oat cultivars. Consistent with the observations in the present study, however, no change in ploidy level was observed in their regenerated oat plants. In another hexaploid species, wheat (2n=6x=42), 29% of regenerated plants were aneuploid (2n=38 to 45) and, as in oat no change in ploidy level (Karp et al., 1984). Johnson et al., (1987c) reported that the most frequent chromosomal alteration in oat was loss of chromosome arms by chromosomal breakage resulting in a heteromorphic pair at diakinesis. This was believed to be caused by late-replication of heterochromatic regions during in vitro culture and further analysis of progeny showed that telocentric-like chromosomes were associated with abnormal behavior during meiosis (Johnson et al., 1987c). In the present study, chromosomal analysis during somatic metaphase revealed only deleted chromosomes or fragments; no other visible structural alterations were found. Cytological variation has also been studied in regenerated plants of diploid monocot species. Over 97% of nontransgenic, regenerated barley plants were diploid (2n=2x=14); however, changes in ploidy level were observed (2n=4x=28) [27, 34, 35]. In pearl millet (2n=2x=14), 99% of regenerated plants ($^{100}/_{101}$) were diploid and the remainder was tetraploid Swedlund and Vasil, 1985). Cytogenetic studies by meitotic analysis McCoy and Phillips, 1982) showed that 96% of regenerated maize plants ($^{119}/_{124}$) were cytologically normal (2n=2x=20). Therefore, in contrast to hexaploid species like oat and wheat the most frequent aberration in diploid species in the nontransgenic regenerated plants appears to be changes in ploidy.

In the case of oat plants regenerated from nontransgenic tissue, there was a difference in frequency of chromosomal aberration among the three different in vitro culturing procedures. These three schemes differed in the media used for culture initiation and maintenance. The first scheme (D') involved the use of D' medium containing 2,4-D alone for the entire culture initiation and maintenance periods. Tissue derived from this scheme likely remained in the embryogenic state. The second scheme (D'BC2) involved the use of D'BC2 medium for initiation and maintenance. It was noted in earlier studies that the addition of the cytokinin BAP and higher copper levels to the 2,4-D in D'BC2 medium leads to the production of more highly regenerative, meristem-like tissues (Cho et al., 1998b). That is, cultures were intiated as embryogenic and with continued culturing in the presence of low levels of BAP were converted to a more meristem-like state. The third scheme (D'BC2/DBC3) involved the use of D'BC2 medium for culture initiation, followed by an maintenance step on DBC3 medium containing higher BAP and lower 2,4-D levels than D'BC2. More regenerable and organized tissues are produced using the D'BC2/DBC3 scheme than using D'BC2 medium alone (Cho et al., 1998c).

Chromosome numbers were compared among nontransgenic oat plants regenerated from 7- to 8-month-old tissues initiated and grown under each of the three schemes. Of the $R_0$ regenerated plants from D' medium 44% (4/9) had chromosomal aberrations, three with aneuploidy (2n=6x=40, 41) and one with a structural variation (2n=6x=40+1f); from D'BC2 medium 14% (2/14) of plants were aneuploid (2n=6x=41). In contrast, all 18 plants regenerated from tissue manipulated using the D'BC2/DBC3 scheme were normal in chromosome number. Thus, as the tissues from which plants were regenerated become and are maintained in a more organized, and meristematic-like states, the plants regenerated from them were less likely to have chromosomal variation. This is consistent with the results of genomic DNA methylation analyses by (Zhang et al., 1999a) which showed barley plants regenerated from the highly regenerative tissues incurred fewer methylation polymorphisms and showed better agronomic performance than those from embryogenic callus tissues, initiated and maintained on 2,4-D alone.

Highly regenerative tissues, produced from D'BC2 or D'BC2/DBC3, were used for transformation. Despite the apparent increase in regenerability and the lower incidence of chromosomal aberration in nontransgenic tissues developed using these improved in vitro culturing methods, frequent chromosomal aberration was observed in transgenic plants. Of 48 independent transgenic lines examined, 42% gave rise to plants, all of which were karyotypically normal (2n=6x=42); 58% gave rise to plants, at least some of which showed chromosomal variation. The frequency of chromosomal abnormalities in the plants from transgenic lines obtained from culturing on D'BC2/DBC3 medium (57%) was not significantly different from those obtained from culturing on D'BC2 medium alone (60%). Given that different chromosome numbers were frequently observed among the plants regenerated from the same $T_0$ line, it is likely that more chromosomal variation occurred than reported here since only 1 or 2 plant(s) from some transgenic lines were analyzed. All six transgenic lines that produced $T_0$ plants with a normal chromosome complement gave rise to $T_1$ progeny that were cytologically normal. In contrast, chromosomal variation was frequent in $T_1$ plants derived from 3 other lines that had chromosomal aberration in $T_0$ plants. One cytologically abnormal $T_0$ line (ASGPC-3, 2n=6x=41) produced some karyotyically normal $T_1$ plants (2n=2x=42). This indicates that plants with a karyotypically normal complement (2n=6x=42) were recovered from karyotypically abnormal plants with 41 chromosomes by fertilization of pollen and egg cells with normal chromosome numbers (n=3x=21) after meiosis.

The most common chromosomal aberration in transgenic oat plants was aneuploidy (2n=6x=40, 41), followed by chromosomal deletion(s) and structural changes with acentric fragments; a number of plants had small telocentric-like chromosomes created by deletion. These observations are in contrast to those recently reported for transgenic diploid barley plants where there was also a high frequency of chromosomal variation (46%); but, all plants underwent a change in ploidy level before other abnormalities were observed. Unlike the transgenic barley plants, no changes in ploidy level were observed in transgenic oat plants. We have also observed frequent aneuploidy without a change in ploidy level in transgenic plants from a hexaploid tall fescue species (*Festuca arundinacea*) (2n=6x=42) (data not shown). Cytological variation has been studied in transgenic plants of a diploid variety of soybean where, in contrast to the results in barley, aneuploid plants around the diploid level (2n=38+3d, 39+1d, 41), were observed in addition to tetraploid plants (2n=4x=80) (Singh et al., 1998). That variation occurs around a diploid number in soybean might be explained by the fact that soybean is considered an ancient allotetraploid with much of its genome duplicated (Shoemaker et al., 1996). In tetraploid tobacco (2n=4x=48), aneuploid plants (2n=4x=49, 50) were observed in progeny of transgenic plants (Matzke et al., 1994). Thus, the nature of chromosomal aberration appears to be dependent upon the particular plant species and its fundamental genomic state.

There was a high correlation between increased fertility and decreased chromosomal variation. Fertility of nontransgenic plants regenerated from D', D'BC2 and D'BC2/DBC3 medium was 78%, 93% and 100%, respectively. The use of D'BC2/DBC3, which maintains tissue in a more developmentally advanced state, leads to more plants that are karyotypically normal and maintain fertility.

In transgenic plants, however, overall fertility was dramatically reduced by the transformation process (52%). Fertility in transgenic oat plants regenerated from tissues maintained on D'BC2/DBC3 medium was higher (60%) than those from D'BC2 (46%). The phenomenon of reduced fertility or sterility has also been observed frequently in other transgenic cereals (Cho et al., 1998b; Hunter, 1988; Gordon-Kam et al., 1992; Vasil et al., 1992), and especially in oat (Somers et al., 1992 and 1996; Torbert et al., 1995 and 1998a; Gless et al., 1998b; Zhang et al., 1999b; Cho et al., 1998b). Previously Somers et al., (Somers et al., 1992) reported that only one out of 111 transgenic lines, generated from cell suspension cultures or embryogenic calli dervied from immature embryos, was fertile. Fertility of transgenic oat plants produced from immature embryo-derived calli, mature seed-derived calli and leaf base segments ranged from 19 to 64%. Recently Zhang et al., (1999b) reported that 71% of transgenic lines produced from cultured axillary meristematic tissue were fertile. In this study, out of twenty independent transgenic lines with normal chromosome numbers, plants regenerated from 15 lines (75%) were fertile. The plants from the remaining 5 lines were sterile, possibly due to undetectable changes in chromosomal fidelity. Most transgenic oat lines with chromosomal abnomalities had no or low seed set; only 36% (10/28) were fertile. Our previous results (Choi et al., 2000) showed that 81% (26/32) of to barley lines with a normal diploid chromosome number had high fertility; in contrast, only 25% of tetraploid or near-tetraploid $T_0$ lines had high fertility. Thus, sterility and low fertility in abnormal plants are likely related to chromosomal damage or instability of chromosome number during abnormal meiosis.

The degree of the in vitro stress incurred by a culture is known to affect chromosomal stability (Constantin et al., 1981; Karp, 1991). In our study it is likely that the additional stresses imposed by the transformation process itself exacerbated the stresses of in vitro growth causing increased chromosomal variation in transgenic oat plants. The DNA introduction process itself is potentially stressful since it involves osmotic treatment, exposure of cells to vacuum, cellular damage due to microprojectile impact and potential loss of cell turgor following particle impact. In addition culturing under selection is necessary to identify transformed tissue (Somers et al., 1992 and 1996; Torbert et al., 1995 and 1998a; Gless et al., 1998b; Zhang et al., 1999b; Cho et al., 1998b; Pawlowski et al., 1998) and, during selection, transformed tissue grows in the presence of dead or dying tissue for prolonged periods, likely resulting in additional cellular stress. That the transformation process causes additional impact on the integrity of the chromosome is consistent with the results reported in this study as well as conclusions from earlier studies showing increased cytological variation in transgenic, compared to regenerated, non-transgenic barley plants (Choi et al., 2000) and a greater negative impact on agronomic performance in transgenic (Bregitzer et al., 1998) versus nontransgenic (Bregitzer and Poulson, 1995) barley plants.

In this study the changes observed in chromosomal number and integrity only permit quantitation of gross changes in chromosomal integrity. It is also likely that other less visible changes in chromosomal fidelity occur e.g., mutation, methylation polymorphism (Phillips et al., 1994; Zhang et al., 1999a); these changes likely also impair the ability of the transgenic plants to grow and reproduce in a manner identical to the nontransgenic parental plants. Therefore, identifying and reducing the stresses associated with the transformation process will likely lead to the development of methods of generating transgenic plants that are more genetically and agronomically identical to the parental plants, a key goal for the manipulation of crop plants through genetic engineering. If this goal is not achieved, additional time-comsuming backcrossing to parental germplasm will have to be undertaken in order to eliminate undesirable induced mutation, a process that will slow the ability to generate transgenic plants that are agronomically identical to the parental germplasm.

Example 11

Transgenic Orchardgrass (*Dactylis glomerata* L.) Plants Produced from Highly Regenerative Tissues Derived from Mature Seeds In this example, an efficient transformation system for orchardgrass via microprojectile bombardment of the highly regenerative tissues derived from mature seed-derived embryogenic callus is described. Chromosomal variation in transgenic orchardgrass plants compared to nontransgenic plants produced from the in vitro culture process alone is discussed.

Materials and Methods

Plant Material and Culture of Explants

Mature seeds of orchardgrass (*Dactylis glomerata* L. cv. Rapido, 2n=4x=28), were surface-sterilized for 20 min in 20% (v/v) bleach (5.25% sodium hypochlorite) followed by 3 washes in sterile water. The seeds were placed on 4 different callus-induction media: (1) D' medium comprising 9.0 μM 2,4-D and 0.1 μM copper (Cho et al., 1999b), (2) D'BC1 medium comprising 9.0 μM 2,4-D, 0.044 μM BAP and 5.0 μM copper (Cho et al., 2000), (3) D'BC2 medium comprising 4.5 μM 2,4-D, 0.44 μM BAP and 5.0 μM copper (Cho et al., 1999b) and (4) DBC3 medium comprising 9.0 μM 2,4-D, 2.2 μM BAP and 5.0 μM copper (Cho et al., 1998b). Five to 7 days after initiation, germinating shoots and roots from mature seeds of Rapido were completely removed by manual excision. After three weeks of incubation at 24±1° C. under dim light conditions (approximately 10 to 30 μE, 16 h-light), the highest-quality tissues with shiny, nodular and compact structures were selected and subsequently subcultured at 3- to 4-week intervals on each medium. D'BC2 or DBC3 medium was used to proliferate highly regenerative, green tissues.

Plasmids

Plasmids, pAct1IHPT-4, pAHC20 and pAHC15, were used for transformation. pAct1IHPT-4 (Cho et al., 1998b) contains the hygromycin phosphotransferase (hpt)-coding sequence under control of the rice actin1 promoter (Act1), its intron (Act1I) and the nos 3' terminator. pAHC20 and pAHC15 (Christensen and Quail 1996) contain phosphinothricin acetyltransferase (bar) and B-glucuronidase (uidA, gus) genes, respectively, each under control of the maize ubiqutin promoter (UbiI) and its intron (Ubi1I) and nos.

Particle Bombardment and Stable Transformation

Approximately 4- to 5-month-old highly regenerative tissue (approximately 30 pieces, 3–4 mm) was transferred for osmotic pre-treatment to D'BC2 or DBC3 medium further comprising mannitol and sorbitol (0.2 M each). Four hours after treatment with the osmoticum, the tissues were bombarded as previously described (Wan and Lemaux, 1994; Lemaux et al., 1996). Gold particles (1.0 μm) were coated with 25 μg of a mixture of pAct1IHPT-4, pAHC20 and pAHC15 at a molar ratio of 1:1:1 followed by bombardment using a PDS-1000 He biolistic device (Bio-Rad, Hercules, Calif.) at 900 psi. Sixteen to 18 hr after bombardment, tissues were placed on D'BC2 or DBC3 medium without osmoticum but supplemented with 30 mg/L hygromycin B and grown at 24±1° C. under dim light (10–30 μE). From the second round selection onward, tissues, subcultured at 3- to 4-week intervals, were maintained on DBC3 medium further comprising 50 mg/L hygromycin B. Following the generation of adequate quantities of highly regenerative tissues on each medium, tissues were plated on FHG medium (Hunter, 1988) comprising 1 mg/L BAP or phytohormone-free BCI-DM⁻ medium (Wan and Lemaux, 1994) without selective agent and exposed to higher-intensity light (approximately 45–55 μE). After four weeks, the regenerated shoots were transferred to the soil and grown in the greenhouse.

Histochemical GUS Assay and Herbicide Application

Plant tissues from each transgenic line were tested for GUS activity by histochemical staining (Jefferson et al., 1987). To determine herbicide sensitivity of transgenic plants, a section of leaf blade was painted using a cotton swab with a 0.25% solution (v/v) of Basta™ solution (starting concentration, 200 g/L phophinothricin, Hoechst AG, Frankfurt, Germany) plus 0.1% Tween 20. Plants were scored 1 week after herbicide application.

Genomic DNA Isolation, Polymerase Chain Reaction (PCR) and DNA Blot Hybridization To test for the presence of uidA, bar and hpt in genomic DNA of putative, independently transformed lines, 500 ng of genomic DNA, isolated from leaf tissues, was amplified by PCR using the primer sets, UIDA1 (5'-agcggccgcaTTACGTCCTGTAGAAACC-3') (SEQ ID NO: 6) plus UIDA2R (5'-agagctcTCATTGTTTGCCTCCCTG-3') (SEQ ID NO: 7) (Cho et al., 1998b), BAR5F (5'-CATCGAGACAAGCACGGTCAACTTC-3') (SEQ ID NO: 4) plus BAR1R (5'-ATATCCGAGCGCCTCGTGCATGCG-3') (SEQ ID NO: 5) (Lemaux et al., 1996), and HPT6F (5'-AAGCCTGAACTCACCGCGACG-3') (SEQ ID NO: 8) plus HPT5R (5'-AAGACCAATGCGGAGCATATAC-3') (SEQ ID NO: 9) (Cho et al., 1998b), respectively. Amplifications were performed in a 25-μl reaction with Taq DNA polymerase (Promega, Madison, Wis.) as described (Cho et al., 1998).

For DNA hybridization analysis, 10 μg of total genomic DNA from leaf tissue of each line was digested with BamHI and EcoRI for detection of uidA and bar from pAHC15 and pAHC20 transformants, respectively, separated on a 1.0% agarose gel, transferred to Zeta-Probe GT membrane (Bio-Rad, Hercules, Calif.) and hybridized with a radiolabeled uidA- or bar-specific probe following manufacturer's instructions. The uidA-containing 1.48-kb SnaBI/SacI fragment and the bar-containing 0.5-kb BamHI/SphI fragment from pAHC25 were purified using a QIAEX gel extraction kit (QIAGEN, Chatsworth, Calif.) and labeled with $\alpha$-$^{32}$P-dCTP using random primers.

Cytological Analysis

Cytological analysis of transgenic orchardgrass plants was performed as described (Choi et al., 2000) using healthy root tips collected from young plants grown in the greenhouse. Chromosomes were counted from at least five well-spread cells per plant.

Results and discussion

Establishment of In Vitro Culturing System

To establish a highly efficient in vitro system for culturing orchardgrass tissue, four different media, D', D'BC1, D'BC2 and DBC3, were tested for callus induction. The use of DBC3 at the initial callus-induction step resulted in high rates of root and shoot formation and low frequencies of callus induction (data not shown). A higher frequency and larger numbers of embryogenic structures were observed on D'BC1 or D'BC2 medium than on DBC3; nonregenerable callus tissues were produced in many cases on D' medium. D'BC2 or DBC3 was optimal for maintaining highly regenerative, green tissues derived from embryogenic callus initiated on D', D'BC1 or D'BC2 medium.

Bombardment and Selection of Transgenic Clones

Four- to 5-month-old highly regenerative tissues containing multiple, light-green, shoot meristem-like structures were used for bombardment. In barley, the expression of a gene associated with maintenance of the meristematic state in barley shoots, a knotted 1 homologue, was studied in tissue derived from the excised shoot apex and from highly regenerative tissues. The pattern was similar in these two tissues (Zhang et al., 1998), suggesting that they bad physiological and developmental similarities (Lemaux et al., 1999). These highly regenerative tissues are believed to have a high percentage of cells capable of sustained cell division and could be maintained for more than two years with minimal loss in regenerability. Similar results were obtained with highly regenerative, green tissues of barley (Cho et al., 1998b), oat (Cho et al., 1999b) and tall and red fescues (Cho et al., 2000). Genomic DNA methylation analyses (Zhang et al, 1999a) showed that barley plants regenerated from the highly regenerative tissues are less variable with regard to those regenerated from embryogenic callus tissues in methylation pattern polymorphism and agronomic performance.

During selection on hygromycin, nontransgenic tissues gradually turned brown and, in general, green, hygromycin-resistant tissues were observed at the third-round selection. Putative transgenic lines were proliferated on the same medium until there was sufficient material for regeneration. Transgenic materials were used for regeneration on FHG or BCI-DM⁻ and plantlets were transferred to soil and grown in the greenhouse. Using this transformation protocol, 11 independent transgenic lines were obtained from 147 pieces of tissues, giving a 7.5% transformation frequency (Table 21). Of eleven transformed lines, a high percentage, 91% (10/11), were regenerable, as was observed with transgenic oat (100%) (Cho et al, 1999) and tall (100%) and red fescue (82%) plants (Cho et al., 2000) obtained from highly regenerative tissues.

TABLE 21

Analysis of transgenic orchardgrass plants

| Transgenic lines | PCR | | | Transgene expression | | Chromosome |
| --- | --- | --- | --- | --- | --- | --- |
| | hpt | bar | uidA | Basta resistance | GUS activity | number (2n) |
| OGTrans-1 | + | + | − | + | − | 56 |
| OGTrans-2 | + | − | − | − | − | 28 |
| OGTrans-3 | + | + | − | + | − | 28 |
| OGTrans-4 | + | − | + | − | + | 56 |
| OGTrans-5 | + | + | − | + | − | 56 |
| OGTrans-6 | + | − | + | − | + | 56 |
| OGTrans-7 | + | − | − | − | − | 56 |
| OGTrans-8 | + | + | − | (+) | − | 56 |
| OGTrans-9 | + | + | + | + | + | 28 |
| OGTrans-10* | + | + | + | n.d.** | + | n.d. |
| OGTrans-11 | + | + | + | + | + | 56 |

*nonregenerable
**not determined

Analysis of Transgenic Plants

GUS expression was detected in putative transgenic leaf tissues (FIG. 1E) and other tissues. Of the eleven independent hygromycin-resistant lines, 5 were positive for GUS activity, giving a 45% coexpression efficiency (Table 21). Strong uidA expression was detected in leaf tissue in OGTrans-4, -6, -9 and -11; GUS expression was not observed in the negative control. Six out of 10 transgenic lines tested were Basta-resistant, giving 60% coexpression efficiency with hygromycin resistance (Table 21); OGTrans-10 was not included because it was not regenerable. Coexpression frequency of the three transgenes (hpt/bar/uidA) was 20%.

Integration and presence of the introduced uidA and bar genes in genomic DNA of $T_0$ plants were confirmed by DNA PCR (Table 1) and DNA blot hybridization analyses. Of the eleven transgenic lines, the presence of a 1.9-kb uidA fragment in five transgenic lines, OGTrans-4, -6, -9, -10 and -11, was confirmed by PCR amplification; a 0.34-kb fragment in seven transgenic lines, OGTrans-1, -3, -5, -8, -9, -10 and -11, confirmed the presence of bar. Integration of uidA and bar into genomic DNA was further confirmed by DNA hybridization analysis. The introduced uidA and bar genes were present in undigested high molecular weight genomic DNA. In addition genomic DNA from OGTrans-4, -6 and -9, transformed with pAHC15, positive for GUS activity and by PCR, produced the expected 1.9 kb-uidA fragment after digestion with BamHI and EcoRI. All three transgenic lines (OGTrans-3, -5, and 9) having Basta resistance produced the 0.5-kb bar fragment after digestion with BamHI and EcoRI. The copy number of the uidA gene ranged from 1 to more than 10 copies per genome; 1–7 copies for bar. Nontransformed plants did not contain DNA which hybridized to either uidA or bar.

Cytological and Phenotypic Variations in Transgenic Plants

Plants from in vitro culture can exhibit somaclonal variation, two characteristics of which are structural rearrangements and variation in chromosome number. Chromosome numbers were counted in cells of the root tips of nontransgenic orchardgrass plants regenerated from 7- to 8-month-old calli initiated on D'BC2 and maintained on DBC3 (Table 22). These tissues were comparable in age to that from which transgenic plants were regenerated. None of 15 tissue culture-derived or 20 seed-derived nontransgenic plants had abnormal ploidy.

Chromosome numbers were also counted in cells of root tips of independently transformed orchardgrass plants. Analysis of this data revealed much greater variation in ploidy in transgenic compared to nontransgenic plants. Two distinct classes of ploidy level were observed in transgenic plants, tetraploid and octaploid (Tables 1 and 2). Of ten independent transgenic lines examined, plants from 3 lines (30%) had the normal octaploid chromosome complement (2n=4x=28) and plants from the remaining 7 lines (70%) were tetraploid (2n=8x=56).

These results are consistent with our earlier results in barley (2n=2x=14) (Choi et al., 2000a). A high frequency of cytological aberration was observed in regenerated, transgenic barley plants; plants from 46% of the independently transformed lines had an altered ploidy level, either tetraploid (2n=4x=28) or aneuploid around the tetraploid level. Nontransgenic barley plants regenerated after in vitro culture alone had a much lower percentage of tetraploids (0 to 4.3%). Similar results were observed in oat (2n=6x=42); a high frequency (60%) of plants with chromosomal aberrations was observed in transgenic lines compared to a low percentage (0 to 14%) in nontransgenic oat plants (Choi et al., 2000b). In the transgenic oat plants, the most common cytogenetic aberration was aneuploidy, followed by deletion of chromosomal segments; no change in ploidy level was observed. In the case of soybean (2n=2x=40), cytological variation, both tetraploidy and aneuploidy around the diploid and tetraploid levels was reported in transgenic soybean plants (Singh et al., 1998). However, soybean is considered an ancient autotetraploid with much of its genome duplicated and hence "diploid" soybean (2n=40) may be more tolerant of aneuploidy or ploidy change than a true diploid (Shoemaker et al., 1996). Thus, the particular type of chromosomal aberration, e.g., ploidy level changes versus aneuploidy and the tolerance for aneuploidy around the original ploid number of chromosomes, appears to be dependent upon the particular plant species and possibly its inherent ploidy level.

In addition to chromosomal abnormalities, certain phenotypic variation was observed in regenerated transgenic plants and these changes were correlated with changes in ploidy level. Octaploid orchardgrass plants had abnormal morphological features, such as narrower, thicker and more upright leaves when compared to tetraploid plants. Similar phenotypic abnormalities were reported in regenerated, tetraploid transgenic barley plants when compared to diploid plants (Choi et al., 2000a).

In conclusion, we established an efficient and reproducible system for orchardgrass (cv. Rapido) transformation using highly regenerative, green tissues derived from mature seed-derived embryogenic callus. We also observed a significantly higher frequency of regenerated, transgenic plants with increased ploidy changes (70%) than in regenerated, nontransgenic plants (0%). The frequency with which chromosomal abnormalities are seen in the transgenic plants might reflect the generalized trend toward chromosomal abnormality mediated by the increased stresses of the transformation process.

TABLE 22

Chromosomal variation in nontransgenic and transgenic orchardgrass plants

| Source of plants | # plants analyzed | Chromosome # 28 | Chromosome # 56 | % aberration |
|---|---|---|---|---|
| Nontransgenic (seed-derived) | 20 | 20 | 0 | 0% (0/20) |
| Nontransgenic (tissue culture-derived) | 14 | 14 | 0 | 0% (0/14) |
| Transgenic | 10 | 3 | 7 | 70.0% (7/10) |

Example 12

Stable Transformation of a of Recalcitrant Kentucky Bluegrass (*Poa Pratensis* L.) Cultivar Using Mature Seed-Derived Highly Regenerative Tissues In this study, media supplemented with three different combinations of the auxin, 2,4-D, the cytokinin, BAP, and cupric sulfate (Cho et al., 1999b) were tested for their ability to sustain in vitro cultures from which plants of Kenblue, a previously recalcitrant cultivar Kentucky bluegrass (*Poa pratensis* L.), could be regenerated for extended periods. The first successful protocol for the genetic transformation of Kentucky bluegrass via microprojectile bombardment is reported here.

Materials and Methods

Culture preparation. Mature seeds of Kentucky bluegrass (*Poa pratensis* L. cv. Kenblue) were rinsed with 70% ethanol for 5 minutes, washed with distilled water for 15 minutes, and then surface-sterilized for 20 minutes in 20% (v/v) commercial bleach (5.25% sodium hypochlorite). Three additional 15-minute washes in sterile water were used to remove residual bleach from seeds. Seeds (15 per plate) were placed on three different MS-based callus induction media: (1) D' medium containing 9.0 μM 2,4-D and 0.1 μM $CuSO_4$ (Cho et al., 1999b), (2) D'BC2 medium containing 9.0 μM 2,4-D, 0.44 μm BAP and 5.0 μM $CuSO_4$ (Cho et al., 1999b) and (3) DBC3 medium containing 4.5 μM 2,4-D, 2.2 μM BAP, and 5.0 μM $CuSO_4$ (Cho et al., 1998b). After five- to 7-d incubation in the dark at 24±1° C., seeds were completely separated from germinating shoots and roots and transferred to plates containing the fresh media and placed under dim light (10 to 30 $\mu Em^{-2}s^{-1}$, 16-h light) at 24±1° C. after four weeks of incubation, tissues with shiny, nodular, and compact structures were selected and subsequently subcultured at 3- to 4week intervals. DBC3 was used to proliferate and maintain highly regenerative, green tissues using tissues initiated on D'BC2.

Shoot regenerability test. Ten to 17 pieces (approximately 5–7 mm diameter) of 10- or 26-month-old tissue from each medium were transferred to FHG regeneration medium (Hunter, 1988) under higher light intensity (45–55 $\mu Em^{-2}s^{-}$₁); six plates were used for each treatment. After 30 d on regeneration medium, the numbers of shoots per tissue piece were obtained. A tissue base that generated more than one leaf was counted as one shoot.

Plasmids for Transformation. Three plasmids, pAct1IHPT-4, pAct1IsGFP-1, and pAHC15, were used for transformation. Plasmid pAct1IHPT-4 (Cho et al., 1998b) contains the hygromycin phosphotransferase (hpt)-coding sequence under control of the rice actin1 promoter (Act1), the actin intron (ActII), and the nos 3' terminator. pAct1IsGFP-1 (Cho et al., 2000) contains the synthetic green fluorescent gene [sfgp(S65T)] (Chiu et al., 1996) under control of the rice actin1 promoter (Act1) and its intron and nos. pAHC15 (Christensen and Quail, 1996) contains the β-glucuronidase (uidA, gus) gene under control of the maize ubiquitin promoter, its intron and nos. Stable Transformation. Ten-month-old highly regenerative callus tissues (3–4 mm in diameter) generated on D'BC2 medium and maintained on DBC3 medium were osmotically treated on DBC3 medium containing mannitol and sorbitol (0.2 M each). Four hours after osmotic pretreatment began, bombardment was conducted as previously described (Lemaux et al., 1996). Twenty-five micrograms of an equimolar mixture of pAct1HPT-4, pAct1IsGFP-1 and pAHC15 were coated on 1.0-μm gold particles (Analytical Scientific Instruments, Alameda, Calif.) and bombarded into the callus tissues using Bio-Rad PDS-1000 He biolistic device (Bio-Rad, Hercules, Calif.) at 900 psi. Sixteen to 18 hrs after bombardment, tissues were transferred to osmoticum-free DBC3 medium without selective pressure under dim light ($10$–$30$ $\mu m^{-2} s^{-1}$). On day 4, they were transferred to DBC3 medium supplemented with 100 mg $l^{-1}$ hygromycin B. After a 2- to 3-wk selection period at 100 mg $l^{-1}$ hygromycin B, tissues were subcultured at 3- to 4-week intervals on DBC3 medium containing 30-mg $l^{-1}$ hygromycin B. When approximately one full plate of putatively transformed, highly regenerative tissues were obtained, tissue pieces (5–7 mm in diameter) were placed on phytohormone-free BCI-DM⁻ (Wan and Lemaux 1994; Cho et al. 1999b) or FHG medium (Hunter, 1988) containing 1 mg $l^{-1}$ BAP without hygromycin B for 4 weeks under higher light intensity ($45$–$55$ $\mu Em^{-2} s^{-1}$). Regenerated plantlets were transferred to Magenta boxes containing BCI-DM⁻ without selective agent for 4–5 weeks to enhance shoot and root formations and then transferred to soil when they were vigorous enough. Functional analyses for GUS and GFP. Plant tissues were tested for GUS activity by histochemical staining (Jefferson et al., 1987) using 5-bromo-4-chloro-3-indoyl-13-D-glucuronic acid (X-gluc) (Gold Biotechnology, Inc., St. Louis, Mo.); samples were incubated overnight at 37° C. in GUS assay buffer before scoring. GFP expression was monitored at high magnification using a Nikon Microphot-5A fluorescent microscope equipped with a Nikon B-2A filter block containing a 450–490 excitation filter and a BA520 emission barrier filter (Cho et al., 2000).

Genomic DNA isolation, polymerase chain reaction (PCR) and DNA blot hybridization analysis. To determine the presence of hpt, sgfp(S65T), and uidA genes in genomic DNA of putative, independently transformed lines, 500 ng of genomic DNA isolated from leaf tissues (Dellapora, 1991) was used in 25-μl PCR reactions with Taq DNA polymerase (Promega, Madison, Wis.) as previously described (Cho et al., 1998b). The individual 2 to 5 plants per line were tested for PCR reactions. The primers sets for hpt were HPT6F (5'-AAGCCTGAACTCACCGCGACG-3') (SEQ ID NO: 8) and HPT5R (5'-AAGACCAATGCGGAGCATATAC-3') (SEQ ID NO: 9) (Cho et al., 1998b); for sgfp(S65T), Act1int1 (5'-TCGTCAGGCTTAGATGTG-3') (SEQ ID NO: 1) and sGFP4R (5'-agaggtaccTTACTTGTACAGCTCGTC-3') (SEQ ID NO: 2) (Cho et al., 2000); for uidA, UIDA1 (5'-agcggccgcaTTACGTCCTGTAGAAACC-3') (SEQ ID NO: 6) and UID2R (5'-agagctcTCATTGTTTGCCTCCCTG-3') (SEQ ID NO: 7) (Cho et al., 1998b).

For DNA blot analysis, 10 μg of total genomic DNA from leaf tissue of each line was digested with SacI for detection of sgfp(S65T) from pAct1IsGFP-1 transformants; 20 μg was digested with XbaI and SacI for detection of uidA from pAHC15 transformants. DNA was electrophoresed on a 0.8% agarose gel at 2.5 V cm⁻¹ for 12 to 15 h, transferred to Duralon-UV™ membrane (Stratagene, Woodinville, Wash.), and hybridized with radiolabeled sgfp(S65T)- or uidA-specific probe at 40% formamide (Stubbs et al., 1990). Probes for sgfp(S65T) utilized a 0.72-kb NcoI-NotI fragment from pAct1IsGFP-1 and for uidA, a 1.48-kb SnaBI-BamHI fragment from pD11-Hor3 (Sørensen et al. 1996); they were purified using a QIAEX gel extraction kit (QIAGEN, Chatsworth, Calif.) and labeled with $\alpha$-³²P-dCTP using random primers. The hybridized blots were washed for 30 minutes at room temperature and 45 minutes at 65° C. with 2×SSC+1% SDS solution (Stubbs et al., 1990).

Results and Discussion

Optimization of an in vitro tissue culture system for Kenblue. Turfgrasses, as with major cereal crops such as maize, wheat, rice, barley, and oat, are generally recalcitrant to in vitro tissue culture methods (Lee, 1996). One such turfgrass, Kentucky bluegrass has proven to be particularly recalcitrant with its various cultivars responding differently in various tissue culture systems and (Boyd and Dale, 1986; Van der Valk, 1989; Griffin and Dibble, 1995). Previously, immature inflorescences of cv. Fylking were used as explants to produce an efficient tissue culture system for Kentucky bluegrass with a 79% regeneration frequency of green plants (Van der Valk, 1989); however, like all previously described culturing methods for Kentucky bluegrass, albino plants were regenerated using this system. Boyd and Dale (1986) reported failure in attempting to generate callus from mature embryos of Kenblue. A decade later, Griffin and Dibble (1995) were able to regenerate shoots from only 4% of seed-derived calli of Kenblue. Of all 12 cultivars tested, cv. Kenblue responds most poorly to tissue culture. With these poorly responding cultures, it would have been extremely difficult, if not impossible, to transform Kenblue.

In the present study, three different media, DBC3, D'BC2, and D' (Cho et al., 1999b), were tested in order to establish an optimal in vitro system for culturing and regenerating Kenblue tissues without albinism. As a general observation, a higher callus-induction frequency, higher callus growth rate, and larger number of embryogenic structures of Kenblue tissue were obtained when callus initiation was on D' medium compared with DBC3 or D'BC2. The use of DBC3 as the primary callus-inducing media resulted in high rates of shoot and root formation directly from seeds, and low frequencies of callus-induction (data not shown). However, DBC3 medium was optimal for development and maintenance of highly regenerative green tissues, once initiated on D' or D'BC2 medium. These tissues contained multiple, light-green, shoot meristem-like structures (not shown); the regenerability of which lasted for 26 months without the occurrence of albino plants (Table 23).

In previous study, the expression of a knotted 1 homologue, gene associated with the maintenance of shoot meristems, was analyzed in barley in cultured meristematic tissue derived from excised shoot apices (Zhang et al., 1998) and from the shoot meristem-like structures of highly regenerative tissues obtained from the same culture methods described here (Lemaux et al., 1999). The expression patterns of this gene were similar, although not identical, in both types of tissues (Lemaux et al., 1999). Therefore, cultured shoot meristem and shoot meristem-like structures of regenerative tissues in our study might share certain physiological and developmental similarities, although their etiology is different. The highly regenerative tissues of Kentucky bluegrass, with what appears to be a high percentage of totipotent cells capable of sustained cell division and competent for regeneration over long periods, represent a target tissue with a high probability for successful transformation.

Bombardment and Selection of Transgenic Lines. The occurrence of albinism and the rapid loss of regenerability during the in vitro tissue culture of Kentucky bluegrass has hindered efforts at improving this species by genetic transformation or by selection for somaclonal variation through tissue culture. In fact, the only attempt to transform Kentucky bluegrass (cv. Touchdown) resulted in only 3.7% of the regenerants from putatively transformed tissue when assayed for GUS assay. However, most transformants were either albino or variegated plants composed of both albino and green tissues (Ke et al., 1996); no further information was reported.

In the present study, ten-month-old highly regenerative, green tissues of Kenblue were used as targets for bombardment. During the selection period on 100 mg $l^{-1}$ hygromycin B, bombarded tissue gradually turned brown, showing no sign of growth. The development of light-green, hygromycin-resistant tissues was not observed until the 3rd to the 6th selection period on 30 mg $l^{-1}$. A transgenic line was defined as tissue deriving from a single bombarded piece of Kenblue tissue; the small clump of green tissue grew slowly at first, sometimes taking up to four weeks to develop from 1 mm to 3 mm in diameter. However, as it reached the size of roughly 5 mm in diameter, the growth rate increased, doubling its size every 10 days. The strategy of starting with high selection pressure and then decreasing it during later selection might help eliminate the early growth of non-transgenic cells, which could escape low selection pressure. During selection, the expression of GFP was easily visible in some transgenic, highly regenerative tissue. When one plate of tissue was obtained per event, regeneration attempts were made on the putatively transformed tissue. Small green plantlets were placed in Magenta boxes for root developments before being transferred to soil in the greenhouse. Our transformation protocol produced 10 independent transgenic lines out of 463 pieces of green tissue, yielding a 2.2% transformation frequency; of these 10 transgenic events, 70% (7/10) were regenerable. No albino plants were observed from any of the transgenic lines. Three non-regenerable transgenic lines gave rise to white, soft, watery tissue during the selection process.

Plants from all regenerable transgenic lines except for Kytrans-4 appeared to have normal phenotypes. KYtrans-4 showed the unusual characteristic of slow growth and partially pale leaf color, possibly due to somaclonal variation or epigenetic effects. Analysis of transgenic lines. PCR analyses of genomic DNA isolated from leaf tissues of regenerated plants or from tissues of non-regenerable lines showed the presence of hpt in all ten transgenic events. Forty and 30 percent of these ten transgenic lines contained gfp and uidA, respectively (Table 24); cotransformation of all three genes (hpt/uidA/gfp) was 20% (2/10).

Expression of the synthetic gfp gene [sgfp(S65T)], which was optimized for human codon usage and driven by the rice actin promoter, was easily observed by fluorescence micros copy in transgenic tissues or in fresh root tips of transgenic plants. Observation of the expression of GFP in transgenic leaves was obscured by chlorophyll fluorescence. Expression of GUS was detected in highly regenerative tissues or leaves from transgenic lines. Coexpression frequency for hpt/sgfp(S65T) was 40% (4/10) and for hpt/uidA it was 30% (3/10). Coexpression frequency for all three transgenes [hpt/sgfp(S65T)/uidA] was 20% (Table 24).

Integration of the introduced sgfp(S65T) and uidA genes into the genomic DNA of transgenic Kenblue lines was confirmed by DNA blot hybridization analyses of undigested genomic DNA samples isolated from young leaf tissues of transgenic plants. The introduced sgfp(S65T) and uidA genes were present in undigested high molecular weight genomic DNA; nontransformed plants did not hybridize to either uidA or sgfp(S65T) probe. Digestion with SacI, was also carried out on genomic DNA isolated from three transgenic lines (KYtrans-1, -2, and -5), which were PCR-positive for sgfp(S65T) and expressed GFP; digestions yielded the expected 1.54-kb sgfp(S65T) band containing the 0.47-kb rice actin 1 intron, 0.72-kb sgfp(S65T), and 0.35-kb nos. Similarly, genomic DNA from two transgenic lines (KYtrans-2 and -3), which were positive for uidA in PCR analyses and expressed GUS, generated a 1.90-kb band containing the coding region for GUS after digestion with XbaI and SacI.

Conclusions

An efficient in vitro culturing system that makes possible the regeneration of plants from one of the most recalcitrant cultivars of Kentucky bluegrass (*Poa pratensis* L. cv. Kenblue) has been established. Use of this system produces highly regenerative, green tissues of Kenblue, which were maintained for 26 months without the occurrence of albinism and with minimal loss in regenerability. The first success in producing transgenic plants of Kentucky bluegrass are also reported. This protocol can be used to improve desired traits in this species through recombinant technologies, making such an approach feasible for basic and applied purposes.

TABLE 23

Regenerability of Kentucky bluegrass tissues on three different media

| Culture medium | Ingredients | | | Regenerability on FHG[a] (No. of shoots/tissue piece) | |
|---|---|---|---|---|---|
| | 2,4-D (μM) | BAP (μM) | CuSO$_4$ (μM) | 10-month-old tissues | 26-month-old tissues |
| DBC3[b] | 4.5 | 2.2 | 5.0 | 3.2 + 0.8 | 3.1 + 1.0 |
| D'BC2 | 9.0 | 0.4 | 5.0 | 0.3 + 0.5 | 0.0 + 0.0[c] |
| D' | 9.0 | 0.0 | 0.1 | 0.0 + 0.0 | 0.0 + 0.0[c] |

[a]Ten to 17 pieces of tissue (~5 to 7 mm in diameter) from each treatment were transferred to FHG regeneration medium and shoots were counted after 30 days. Values represent means ± SD of six replicates of each treatment
[b]D'BC2 for initiation and DBC3 for maintenance
[c]Tissues on D'BC2 and D' were not viable at 26 months

TABLE 24

Analysis of transgenic Kentucky bluegrass callus and plants

| Plasmids used for transformation | Transgenic lines | PCR | | | Transgene Expression | |
|---|---|---|---|---|---|---|
| | | hpt | gfp | uidA | GFP | GUS |
| pAct1IHPT-4 + pAHC15 + pAct1IsGFP-1 | KYtrans-1 | + | + | − | + | − |
| | KYtrans-2 | + | + | + | + | + |
| | KYtrans-3 | + | − | + | − | + |
| | KYtrans-4 | + | − | − | − | − |
| | KYtrans-5 | + | + | − | + | − |
| | KYtrans-6[a] | + | + | + | + | + |
| | KYtrans-7 | + | − | − | − | − |
| | KYtrans-8 | + | − | − | − | − |
| | KYtrans-9[a] | + | − | − | − | − |
| | KYtrans-10[a] | + | − | − | − | − |
| | 10/463 = 2.2%[b] | 10/10 = 100% | 4/10 = 40% | 3/10 = 30% | 4/10 = 40% | 3/10 = 30% |

[a]Nonregenerable lines
[b]Transformation frequency: 10 independent transgenic lines were obtained from bombardment of 463 callus pieces Example 13

Effect of Different Auxin Types and Copper Concentrations on Callus Quality and its Regenerability in Barley To examine the effects of different types of auxins and concentrations of copper on callus quality and regenerability in barley, twelve different media were tested, using methods essentially as described in Example 2 above. All six types of auxins (2,4-D, NAA, dicamba, picloram, IAA and 2,4,5-T) tested induced callus tissues from immature embryos, but IAA produced poorer callus quality than the other auxins and induced root formation from callus tissues. In general, the increased copper level (5.0 μM) over that in basal MS (0.1 μM) improved the callus quality with all types of auxins except for NAA. The frequency of shoot regeneration for calli was dependent upon the types of auxins. Neither IAA nor NAA was optimal for induction of calli which regenerated green plants. In contrast, other 4 auxins, 2,4-D, dicamba, picloram, and 2,4,5-T, produced calli which regenerated 0.8 to 1.3 plants per callus piece (5 to 7 mm in diameter); green shoot production also increased with the addition of copper level to callus-induction media containing these 4 auxins.

TABLE 25

Callus quality and regenerability from calli of Golden Promise grown on twelve different callus-induction media

| | Composition | | | | Regenerability |
|---|---|---|---|---|---|
| Medium | Auxin source | Auxin conc. (mg/L) | $CuSO_4$ (μM) | Callus quality | (# shoots/ callus piece) |
| D | 2,4-D | 2.5 | 0.1 | +++(+) | 1.33 ± 0.33 |
| DC | 2,4-D | 2.5 | 5.0 | ++++ | 2.76 ± 0.33 |
| N | NAA | 2.5 | 0.1 | +++(+) | 0 ± 0 |
| NC | NAA | 2.5 | 5.0 | +++ | 0 ± 0 |
| DM | Dicamba | 2.5 | 0.1 | +++ | 0.81 ± 0.17 |
| DMC | Dicamba | 2.5 | 5.0 | ++++ | 3.71 ± 0.52 |
| P | Picloram | 2.5 | 0.1 | +++ | 1.19 ± 0.22 |
| PC | Picloram | 2.5 | 5.0 | +++(+) | 1.71 ± 0.25 |
| I | IAA | 2.5 | 0.1 | ++ | 0 ± 0 |
| IC | IAA | 2.5 | 5.0 | +++ | 0 ± 0 |

TABLE 25-continued

Callus quality and regenerability from calli of Golden Promise grown on twelve different callus-induction media

| | Composition | | | | Regenerability |
|---|---|---|---|---|---|
| Medium | Auxin source | Auxin conc. (mg/L) | $CuSO_4$ (μM) | Callus quality | (# shoots/ callus piece) |
| T | 2,4,5-T | 2.5 | 0.1 | +++ | 0.52 ± 0.08 |
| TC | 2,4,5-T | 2.5 | 5.0 | +++(+) | 1.52 ± 0.33 |

Calli were induced from immature embryos and maintained on 12 different callus-induction media (CIMs). Each CIM contains different combinations of auxins and copper. Seven 49-day-old-calli were transferred onto FHG regeneration medium. Values for regenerability were measured 25 days after incubation on FHG and represent mean ± standard deviation of three replicates for each treatment. Callus quality was assessed microscopically and scored on a scale with "++++" being the highest quality and "+" being the lowest.

REFERENCES

Ausubel et al. eds. (1992, with periodic updates) *Current Protocols in Molecular Biology*, Greene Publishing and Wiley-Interscience, New York.
Baillie et al. (1993) *Can. J. Plant Sci.* 73:171–174.
Besse et al. (1996) *Proc Natl Acad Sci USA* 93:3169–3175.
Bettany et al. (1998) *J Exp Botany* 49:1797–1804.
Bhaskaran and Smith (1990) *Crop Sci.* 30:1328–1336.
Boyd et al. (1986) *Plant Breeding* 97:246–254.
Brandt et al. (1985) *Carlsberg Res Commun* 50:333–345.
Bregitzer (1992) *Crop Sci.* 32:1108–1112.
Bregitzer and Poulson (1995) *Crop Sci.* 35:1144–1148.
Bregitzer et al (1995) *Plant Cell Tiss. Org. Cult.* 43:229–235.
Bregitzer et al. (1998) *Theor. Appl Genet.* 96:421–425.
Breimann (1985) *Plan Cell Rep.* 4:161–163.
Buchanan et al. (1997) *Proc Natl Acad Sci USA* 94:5372–5377.
Chiu et al. (1996) *Current Biol* 6:325–330.
Cho and Lemaux (1997) *Mol Biotechnol* 8:13–16.
Cho and Lemaux (1999) *Congress In Vitro Biol*, New Orleans, La. 5–9 June, 1999.
Cho et al. (1998a) *Congress In Vitro Biol*, Las Vegas, Nev., 30 May–3 June, 1998.
Cho et al (1998b) *Plant Sci* 138:229–244.
Cho et al. (1998c) *In Vitro Cell. Dev. Biol.* 34 vol. 4 SP-1012.
Cho et al. (1999a) *Theor Appl Genet* 98:1253–1262.

Cho et al. (1999b) *Plant Sci* 148:9–17.
Cho et al. (1999c) *Proc. Natl. Acad. Sci USA* 96:14641–46.
Cho et al. (2000) *Plant Cell Rep* (accepted).
Choi et al. (2000a) *Crop Sci.* 40:524–533.
Choi et al. (2000b) *Plant Sci.* (in press).
Christensen and Quail (1996) *Transgenic Res.* 5:1–6.
Constantin (1981) *Environ. Exp. Bot.* 21:359–368.
Cummings et al. (1976) *Crop Sci.* 16:465–470.
Dahleen (1996) *Plant Cell Tiss. Org. Cult.* 43:267–269.
Dale and Dambrogio (1979) *Z. Pflanzenphysiol.* 94:65–77.
Dalton et al. (1995) *Plant Sci* 108:63–70.
Dalton et al. (1998) *Plant Sci* 132:31–43.
De Block et al. (1987) *EMBO J.* 6:2513–2518.
del Val et al. (1999) *J Allergy Clinical Immunol* 103:690–697.
Delagrave et al. (1995) *Bio/Technology* 13:151–154.
Dellaporta (1993) *Maize Handbook*, pp. 522–525.
Denchev et al. (1997) *Plant Cell Rep* 16:813–819.
Dmitrieva (1985) "Hormones, Dedifferentiation and Control of Proliferation in Cell and Protoplast Cultures," in: Butenko, ed., *Plant Cell Culture*, Biology Series, MIR Publishers, Moscow, pp. 35–50.
Fiedler and Conrad (1995) *Bio/Technology* 13:1090–1093.
Fletcher (1969) *Planta* 89:1–8.
Foroughi-Wehr et al. (1982) *Theor. Appl. Genet.* 62:233–239.
Fromm et al. (1986) *Nature* 319:791–793.
Fromm et al. (1989) *Plant Cell* 1:977.
Funatuski et al. (1995) *Theor. Appl. Genet.* 91:707–712.
Gaponenko et al. (1988) *Theor. Appl. Genet.* 75:905–911.
Gasser and Fraley (1989) *Science* 244:1293–1299.
Gautier et al. (1998) *Eur J Biochem* 252:314–324.
Gelvin et al. (1990) *Plant Molecular Biology Manual*, Kluwer Academic Publishers.
Ghaemi et al. (1994) *Plant Cell Tiss. Org. Cult.* 36:355–359.
Gless et al. (1998a) Plant Cell Rep. 17:441–445.
Gless et al. (1998b) J. Plant Physiol. 152:151–157.
Goldenstein and Kronstadt (1986) *Theor. Appl. Genet.* 71:631–636.
Gordon-Kamm et al. (1990) *Plant Cell* 2:603–618.
Griffin and Dibble (1995) *Plant Cell Rep.* 14:721–724.
Ha et al. (1992) *Plant Cell Rep* 11:601–604.
Hagio et al. (1995) *Plant Cell Rep.* 14:329–334.
Handel et al. (995) Crop Sci. 25:27–31.
Heim et al. (1995) *Nature* 373:663–664.
Holtorf et al. (1995) *Proc. Natl. Acad. Sci. USA* 92:3254–3258.
Horn et al. (1988) *Plant Cell Rep* 7:469–472.
Hughes and Qoronfleh (1991) *BioPharm* 4:18–26.
Hunter (1988) "Plant regeneration from microspores of barley, *Hordeum vulgare*," PhD thesis, Wye College, University of London, Ashford, Kent, England.
Jähne et al. (1991) *Plant Cell. Rep.* 10: 1–6.
Jähne et al. (1994) *Theor. Appl. Genet.* 89:525–533.
Jefferson et al. (1987) *EMBO J.* 6:3901–3907.
Jiang et al. (1998) *Plant Biotechnology* 15:63–69.
Johnson et al. (1987a) Plant Physiol 85:446–451.
Johnson et al. (1987b) *Genome* 29:431–438.
Johnson et al. (1987c) *Genome* 29:439–446.
Kao et al. (1991) *Plant Cell Rep.* 9:595–601.
Karp (1991) *Surveys of Plant Mol and Cell Biol.* Oxford University Press, pp. 1–58.
Karp (1995) *Euphytica* 85:295–302.
Karp and Maddock (1984) *Theor. Appl. Genet.* 67:249–255.
Karp et al. (1987) *Genome* 29:405–412.
Kasha et al. (1990) "Haploids in cereal improvement: Anther and microspore culture," in: *Gene manipulation in plant improvement II*, ed., Gustafson, Plenum, New York, pp. 213–235.
Kim et al. (1999) *Congress In Vitro Biol*, New Orleans, La. 5–9 Jun., 1999.
Kobrehel et al. (1991) *J Biol Chem* 266:16135–16140.
Kobrehel et al. (1992) *Plant Physiol* 99:919–924.
Koprek et al. (1999) *Proc 9th Australian Barley Technical Symposium*, Melboubne, Victoria, Australia, 12–16 Sep., 1999, pp. 2.3.1–2.3.8.
Koprek et al. (1996) *Plant Sci.* 119:79–91.
Kott and Kasha (1984) *Can. J. Bot.* 62:1245–1249.
Krebbers et al. (1992) *Plant Protein Engineering* (Shewry PR and Gutteridge S eds.) University Press, Cambridge, pp. 315–325.
Kuai and Morris (1995) *Plant Sci* 110:235–247.
Larkin and Scowcroft (1981) *Theor. Appl. Genet.* 60:197–214.
Lee and Phillips (1987) *Genome* 29:122–128.
Lee and Phillips (1988) *Ann. Rev. Plant Physiol. Plant Mol. Biol.* 39:413–437.
Lemaux et al. (1996) *Bombardment-mediated transformation methods for barley*, Bio-Rad US/EG Bulletin 2007.
Lemaux et al. (1999) *Molecular Improvement of Cereal Crops* (IK Vasil ed.) Kluwer Academic Publ, UK, pp 255–316.
Lewin (1994) Genes V, Oxford University Press: New York.
Liu (1994) *Analysis of ABA-Regulated Expression of the Maize GLB1 Gene in Tobacco Seeds and Maize Cells*, Ph.D. thesis, University of Illinois at Urbana-Champaign.
Lozano et al. (1996) *Planta* 200:100–106.
Lürz and Lörz (1987) *Theor. Appl. Genet.* 75: 16–25.
Marris et al. (1988) *Plant Mol Biol* 10:359–366.
Matzke et al. (1994) *Mol. Gen. Genet.* 245:471–485.
McCoy and Phillips (1982) *Can. J Genet. Cytol.* 24:559–565.
McCoy et al. (1982) *Can. J. Genet. Cyto.* 24:37–50.
Miller (1984) *Forage Crops*, McGraw-Hill, NY, pp. 396–409.
Murakami et al. (1986) *Mol. Gen. Genet.* 205:42–50.
Murashige and Skoog (1962) *Physiol. Plant.* 15:473–497.
Pawlowski and Somers (1996) *Molecular Biotechnol.* 6:17–30.
Pawlowski and Somers (1998) *Proc. Natl. Acad. Sci. USA* 95:12106–12110.
Pawlowski et al. (1998) *Plant Mol. Biol.* 38:597–607.
Pen and Sijmons (1993) *Transgenic Plants-Fundamentals and Applications* (Hiatt A ed.) Dekker, New York, pp 238–251.
Phillips et al. (1994) *Proc. Natl. Acad. Sci. USA* 91:5222–5226.
Pouwels et al. (1985, supp. 1987) *Cloning Vectors: a Laboratory Manual*.
Prasher et al. (1992) *Gene* 111:229–233.
Purnhauser (1991) *Cereal Res. Comm.* 19:419–423.
Rhagaran (1986) *Embryogenesis in Angiosperms*, Cambridge Univ. Press: Cambridge, p. 303.
Rieger et al. (1991) *Glossary of Genetics: Classical and Molecular*, 5th edition, Springer-Verlag: New York.
Roshal et al. (1987) *EMBO J.* 6:1155.
Salmenkallio-Marttila et al. (1995) *Plant Cell Rep.* 15:301–304.
Sambrook et al. (eds.) (1989), *Molecular Cloning: a Laboratory Manual*, 2nd ed., vol. 1–3, Cold Spring Harbor Laboratory Press: Cold Spring Harbor, N.Y.
Shoemaker et al. (1996) *Genetics* 144:329–338.
Singh et al. (1998) *Theor. Appl. Genet.* 96:319–324.
Somers et al. (1992) *Bio/Technology* 10:1589–1594.
Somers et al. (1996) *Biotechnology in Agriculture and Forestry Vol.* 38, Springer, pp. 178–190.

Somers (1999) *Molecular Improvement of Cereal Crops*, Kluwer, Drodrecht, pp. 317–339.
Somers et al. (1994) *Improvement of Cereal Quality by Genetic Engineering*, Plenum Press, New York, pp. 37–46.
Sørensen et al. (1996) *Mol Gen Genet* 250:750–760.
Spangenberg et al. (1994) *Plant Sci* 97:83–94.
Spangenberg et al. (1995) *J Plant Physiol* 145:693–701.
Stubbs et al. (1990) *Genomics* 6:645–650.
Swedlund and Vasil (1985) *Theor. Appl. Genet.* 69:575–581.
Thomas and Scott (1985) *Plant Cell Rep.* 15:301–304.
Thompson et al. (1987) *EMBO J.* 6:2519–2523.
Tisserat (1985) "Embryogenesis, Organogenesis and Plant Regeneration," in: Dixon, ed., *Plant Cell Culture: a Practical Approach*, Practical Approach Series, IRL Press, Oxford, Washington, D.C., pp. 79–105.
Torbet et al. (1995) *Plant Cell Rep.* 14:635–640.
Torbet et al. (1998) *Plant Cell Rep.* 17:284–287.
Torbet et al. (1998 a) *Crop Sci.* 38:226–231.
Torbet et al. (1998b) *Crop Sci.* 38:1685–1687.
Vandekerckchove et al. (1989) *Bio/Technology* 7:929–932.
Van der Valk et al. (1989) *Plant Cell Rep.* 7:644–647.
Vasil (1984) *Cell Culture and Somatic Cell Genetics of Plants*, Vols. I–III, *Laboratory Procedures and their Applications*, Academic Press: New York.
Vasil (1994) *Plant Mol. Biol.* 25:925–937.
Vasil et al. (1992) *Bio/Technology* 10:667–674.
Vollbrecht et. al. (1991) *Nature* 350:241–243.
Wan and Lemaux (1994) *Plant Physiol.* 104:37–48.
Wang et al. (1992) *Bio/Technology* 10:691–696.
Weissbach and Weissbach (1989) *Methods for Plant Molecular Biology*, Academic Press: New York.
Wetmur and Davidson (1968) *J Mol. Biol.* 31:349–370.
Wong et al. (1993) *Cereal Chemistry* 70:113–114.
Zhang et al. (1996) *J. Plant Physiol.* 148:667–671.
Zhang et al. (1998) *Planta.* 204:542–549.
Zhang et al. (1999a) *Plant Biotechnology and In Vitro Biology in the 21 $^{st}$ Century* (A. Altman ed.) Kluwer Academic Publishers, the Netherlands, pp. 263–267.
Zhang et al. (1999b) Plant Cell Rep. 18:959–966.
Zhong et al. (1991) *Plant Cell Rep.* 10:435–456.
Zhong et al. (1992) *Planta* 187:483–489.
Ziauddin and Kasha (1990) *Euphytica* 48:171–176.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for, purposes of clarity of understanding, it will be obvious that certain changes and modifications may be practiced within the scope of the appended claims.

What is claimed is:

1. A method for producing a transformed monocot plant, comprising:

(a) providing a monocot plant embryo;

(b) introducing a nucleic acid into a monocot plant cell from the monocot plant embryo to produce a transformed plant cell;

(c) culturing the transformed plant cell under dim light of approximately 10 to 30 µE on an incubation medium comprising an auxin and a cytokinin for about 5 to 20 days to produce a transformed plant tissue that is green, shiny, nodular and compact as compared to monocot plant callus tissue; and (d) culturing the transformed plant tissue on a regeneration medium to produce the transformed monocot plant.

2. The method of claim 1 wherein the auxin is selected from the group consisting of 2,4-dichlorophenoxyacetic acid, dicamba, naphthaleneacetic acid, indoleacetic acid, picloram, 2,4,5-trichlorophenoxyacetic acid and mixtures thereof.

3. The method of claim 1 wherein the cytokinin is selected from the group consisting of 6-benzylaminopurine, zeatin, zeatin riboside, kinetin, 2iP, and mixtures thereof.

4. The method of claim 1 wherein the auxin is at a concentration of about 0.1 mg/L to about 5 mg/L.

5. The method of claim 1 wherein the cytokinin is at a concentration of about 0.01 mg/L to about 5 mg/L.

6. The method of claim 1 wherein the incubation medium further comprises copper at a concentration of about 0.1 µM to about 50 µM.

7. The method of claim 1 wherein the incubation medium further comprises a carbon source.

8. The method of claim 1, wherein the auxin is at a concentration of about 0.1 mg/L to about 5 mg/L and the cytokinin is at a concentration of about 0.1 mg/L to about 5 mg/L; and the incubation medium further comprises copper at a concentration of about 0.1 µM to about 50 µM, and maltose.

9. The method of claim 1 further comprising selecting for the transformed plant cell by incubating the plant cell on a growth medium comprising a selective agent.

10. The method of claim 1 wherein the step of introducing the nucleic acid comprises bombardment of the plant cell with microprojectiles coated with the nucleic acid.

11. The method of claim 10 wherein bombardment is performed at below 1300 psi.

12. The method of claim 11 wherein bombardment is performed at about 900 to about 1100 psi.

13. The method of claim 1 wherein the monocot plant is selected from the group consisting of barley, oat, wheat, maize, rice, sorghum, orchardgrass, tall fescue, red fescue, creeping bentgrass and Kentucky bluegrass.

14. The method of claim 13 wherein the barley is selected from the group consisting of Golden Promise, Galena, Harrington, Morex, Moravian III, and Salome.

15. The method of claim 13 wherein the wheat is selected from the group consisting of Bobwhite, Anza, Yecora Rojo and Karl.

16. The method of claim 13 wherein the maize is H99 or B73.

17. The method of claim 13 wherein the rice is Taipei 309.

18. The method of claim 13 wherein the orchardgrass is Rapido.

19. The method of claim 13 wherein the tall fescue is Ky 31.

20. The method of claim 13 wherein the red fescue is 43F-93.

21. The method of claim 13 wherein the creeping bentgrass is Putter.

22. The method of claim 13 wherein the Kentucky bluegrass is Kenblue.

\* \* \* \* \*

UNITED STATES PATENT AND TRADEMARK OFFICE
CERTIFICATE OF CORRECTION

| | | |
|---|---|---|
| PATENT NO. | : 7,102,056 B1 | Page 1 of 1 |
| APPLICATION NO. | : 09/552252 | |
| DATED | : September 5, 2006 | |
| INVENTOR(S) | : Peggy G. Lemaux et al. | |

It is certified that error appears in the above-identified patent and that said Letters Patent is hereby corrected as shown below:

At column 1, preceding line 5, please insert the following statement:

--The research underlying this invention was supported with funds from USDA Grant No. CSRS 93-37500-9586. The U.S. Government may have certain rights.--

Signed and Sealed this

Tenth Day of July, 2007

JON W. DUDAS
*Director of the United States Patent and Trademark Office*